United States Patent
Rockrohr

(10) Patent No.: US 11,618,171 B2
(45) Date of Patent: *Apr. 4, 2023

(54) WRIST AND JAW ASSEMBLIES FOR ROBOTIC SURGICAL SYSTEMS

(71) Applicant: Covidien LP, Mansfield, MA (US)

(72) Inventor: Brian Rockrohr, Guilford, CT (US)

(73) Assignee: COVIDIEN LP, Mansfield, MA (US)

(*) Notice: Subject to any disclaimer, the term of this patent is extended or adjusted under 35 U.S.C. 154(b) by 992 days.

This patent is subject to a terminal disclaimer.

(21) Appl. No.: 16/246,753

(22) Filed: Jan. 14, 2019

(65) Prior Publication Data

US 2019/0143535 A1 May 16, 2019

Related U.S. Application Data

(63) Continuation of application No. 15/921,093, filed on Mar. 14, 2018, now Pat. No. 10,179,413, which is a (Continued)

(51) Int. Cl.
*A61B 34/00* (2016.01)
*A61B 34/30* (2016.01)
(Continued)

(52) U.S. Cl.
CPC ..... *B25J 15/0226* (2013.01); *A61B 17/00234* (2013.01); *A61B 34/30* (2016.02);
(Continued)

(58) Field of Classification Search
CPC ... B25J 15/0226; B25J 15/0233; A61B 34/77; A61B 2017/2934; A61B 17/00234;
(Continued)

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

CA 2451558 A1 1/2003
CN 1547454 A 11/2004
(Continued)

OTHER PUBLICATIONS

Chinese Office Action for application No. 201910322870.3 dated Jul. 2, 2021 with English translation.
(Continued)

*Primary Examiner* — Melanie R Tyson
*Assistant Examiner* — Bridget E. Rabaglia
(74) *Attorney, Agent, or Firm* — Carter, DeLuca & Farrell LLP

(57) ABSTRACT

An end effector for use and connection to a robot arm of a robotic surgical system, wherein the end effector is controlled and/or articulated by at least one cable extending from a respective motor of a control device of the robot surgical system, is provided. The end effector includes a wrist assembly, and a jaw assembly. The jaw assembly includes a cam pulley rotatably supported on at least one support plate of the jaw assembly, wherein the cam pulley is operatively connected to a proximal end of each of the jaws of the jaw assembly such that rotation of the cam pulley results in one of an opening and closing of the jaw assembly.

16 Claims, 36 Drawing Sheets

Related U.S. Application Data continuation of application No. 15/102,081, filed as application No. PCT/US2014/061329 on Oct. 20, 2014, now Pat. No. 9,937,626.

(60) Provisional application No. 61/914,632, filed on Dec. 11, 2013.

(51) Int. Cl.
*A61B 17/00* (2006.01)
*A61B 17/29* (2006.01)
*B25J 15/02* (2006.01)

(52) U.S. Cl.
CPC ............ *A61B 34/71* (2016.02); *B25J 15/0233* (2013.01); *A61B 34/77* (2016.02); *A61B 2017/00323* (2013.01); *A61B 2017/2934* (2013.01); *A61B 2017/2936* (2013.01); *A61B 2034/305* (2016.02)

(58) Field of Classification Search
CPC ............... A61B 34/30; A61B 34/71; A61B 2017/00323; A61B 2017/2936; A61B 2034/305
USPC ....... 294/116, 110.2, 118, 104; 606/205, 207
See application file for complete search history.

(56) References Cited

U.S. PATENT DOCUMENTS

| | | |
|---|---|---|
| 3,111,328 A | 11/1963 | Di Rito et al. |
| 3,695,058 A | 10/1972 | Keith, Jr. |
| 3,734,515 A | 5/1973 | Dudek |
| 3,759,336 A | 9/1973 | Marcovitz et al. |
| 4,162,399 A | 7/1979 | Hudson |
| 4,606,343 A | 8/1986 | Conta et al. |
| 4,705,038 A | 11/1987 | Sjostrom et al. |
| 4,722,685 A | 2/1988 | de Estrada et al. |
| 4,823,807 A | 4/1989 | Russell et al. |
| 4,874,181 A | 10/1989 | Hsu |
| 5,129,118 A | 7/1992 | Walmesley |
| 5,129,570 A | 7/1992 | Schulze et al. |
| 5,152,744 A | 10/1992 | Krause et al. |
| 5,301,061 A | 4/1994 | Nakada et al. |
| 5,312,023 A | 5/1994 | Green et al. |
| 5,326,013 A | 7/1994 | Green et al. |
| 5,350,355 A | 9/1994 | Sklar |
| 5,383,874 A | 1/1995 | Jackson et al. |
| 5,383,880 A | 1/1995 | Hooven |
| 5,389,098 A | 2/1995 | Tsuruta et al. |
| 5,395,033 A | 3/1995 | Byrne et al. |
| 5,400,267 A | 3/1995 | Denen et al. |
| 5,411,508 A | 5/1995 | Bessler et al. |
| 5,413,267 A | 5/1995 | Solyntjes et al. |
| 5,427,087 A | 6/1995 | Ito et al. |
| 5,433,721 A | 7/1995 | Hooven et al. |
| 5,467,911 A | 11/1995 | Tsuruta et al. |
| 5,476,379 A | 12/1995 | Disel |
| 5,487,499 A | 1/1996 | Sorrentino et al. |
| 5,518,163 A | 5/1996 | Hooven |
| 5,518,164 A | 5/1996 | Hooven |
| 5,526,822 A | 6/1996 | Burbank et al. |
| 5,529,235 A | 6/1996 | Boiarski et al. |
| 5,535,934 A | 7/1996 | Boiarski et al. |
| 5,535,937 A | 7/1996 | Boiarski et al. |
| 5,540,375 A | 7/1996 | Bolanos et al. |
| 5,540,706 A | 7/1996 | Aust et al. |
| 5,542,594 A | 8/1996 | McKean et al. |
| 5,549,637 A | 8/1996 | Crainich |
| 5,553,675 A | 9/1996 | Pitzen et al. |
| 5,562,239 A | 10/1996 | Boiarski et al. |
| 5,564,615 A | 10/1996 | Bishop et al. |
| 5,609,560 A | 3/1997 | Ichikawa et al. |
| 5,626,587 A | 5/1997 | Bishop et al. |
| 5,632,432 A | 5/1997 | Schulze et al. |
| 5,645,209 A | 7/1997 | Green et al. |
| 5,647,526 A | 7/1997 | Green et al. |
| 5,653,374 A | 8/1997 | Young et al. |
| 5,658,300 A | 8/1997 | Bito et al. |
| 5,662,662 A | 9/1997 | Bishop et al. |
| 5,667,517 A | 9/1997 | Hooven |
| 5,693,042 A | 12/1997 | Boiarski et al. |
| 5,704,534 A | 1/1998 | Huitema et al. |
| 5,713,505 A | 2/1998 | Huitema |
| 5,752,973 A | 5/1998 | Kieturakis |
| 5,762,603 A | 6/1998 | Thompson |
| 5,779,130 A | 7/1998 | Alesi et al. |
| 5,782,396 A | 7/1998 | Mastri et al. |
| 5,782,397 A | 7/1998 | Koukline |
| 5,792,573 A | 8/1998 | Pitzen et al. |
| 5,797,536 A | 8/1998 | Smith et al. |
| 5,820,009 A | 10/1998 | Melling et al. |
| 5,863,159 A | 1/1999 | Lasko |
| 5,908,427 A | 6/1999 | McKean et al. |
| 5,954,259 A | 9/1999 | Viola et al. |
| 5,964,774 A | 10/1999 | McKean et al. |
| 5,993,454 A | 11/1999 | Longo |
| 6,010,054 A | 1/2000 | Johnson et al. |
| 6,017,354 A | 1/2000 | Culp et al. |
| 6,032,849 A | 3/2000 | Mastri et al. |
| 6,045,560 A | 4/2000 | McKean et al. |
| 6,090,123 A | 7/2000 | Culp et al. |
| 6,126,651 A | 10/2000 | Mayer |
| 6,129,547 A | 10/2000 | Cise et al. |
| 6,132,368 A | 10/2000 | Cooper |
| 6,165,169 A | 12/2000 | Panescu et al. |
| 6,206,903 B1 | 3/2001 | Ramans |
| 6,239,732 B1 | 5/2001 | Cusey |
| 6,241,139 B1 | 6/2001 | Milliman et al. |
| 6,246,200 B1 | 6/2001 | Blumenkranz et al. |
| 6,264,086 B1 | 7/2001 | McGuckin, Jr. |
| 6,264,087 B1 | 7/2001 | Whitman |
| 6,302,311 B1 | 10/2001 | Adams et al. |
| 6,312,435 B1 | 11/2001 | Wallace et al. |
| 6,315,184 B1 | 11/2001 | Whitman |
| 6,321,855 B1 | 11/2001 | Barnes |
| 6,329,778 B1 | 12/2001 | Culp et al. |
| 6,331,181 B1 | 12/2001 | Tierney et al. |
| 6,343,731 B1 | 2/2002 | Adams et al. |
| 6,348,061 B1 | 2/2002 | Whitman |
| 6,368,324 B1 | 4/2002 | Dinger et al. |
| 6,371,909 B1 | 4/2002 | Hoeg et al. |
| 6,394,998 B1 | 5/2002 | Wallace et al. |
| 6,424,885 B1 | 7/2002 | Niemeyer et al. |
| 6,434,507 B1 | 8/2002 | Clayton et al. |
| 6,441,577 B2 | 8/2002 | Blumenkranz et al. |
| 6,443,973 B1 | 9/2002 | Whitman |
| 6,459,926 B1 | 10/2002 | Nowlin et al. |
| 6,461,372 B1 | 10/2002 | Jensen et al. |
| 6,488,197 B1 | 12/2002 | Whitman |
| 6,491,201 B1 | 12/2002 | Whitman |
| 6,491,691 B1 | 12/2002 | Morley et al. |
| 6,491,701 B2 | 12/2002 | Tierney et al. |
| 6,493,608 B1 | 12/2002 | Niemeyer |
| 6,533,157 B1 | 3/2003 | Whitman |
| 6,537,280 B2 | 3/2003 | Dinger et al. |
| 6,565,554 B1 | 5/2003 | Niemeyer |
| 6,610,066 B2 | 8/2003 | Dinger et al. |
| 6,611,793 B1 | 8/2003 | Burnside et al. |
| 6,645,196 B1 | 11/2003 | Nixon et al. |
| 6,645,218 B1 | 11/2003 | Cassidy et al. |
| 6,654,999 B2 | 12/2003 | Stoddard et al. |
| 6,659,939 B2 | 12/2003 | Moll et al. |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,698,643 B2 | 3/2004 | Whitman |
| 6,699,177 B1 | 3/2004 | Wang et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,743,240 B2 | 6/2004 | Smith et al. |
| 6,746,443 B1 | 6/2004 | Morley et al. |

(56) References Cited

U.S. PATENT DOCUMENTS

| | | |
|---|---|---|
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,783,533 B2 | 8/2004 | Green et al. |
| 6,792,390 B1 | 9/2004 | Burnside et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,817,508 B1 | 11/2004 | Racenet et al. |
| 6,830,174 B2 | 12/2004 | Hillstead et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,860,892 B1 | 3/2005 | Tanaka et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,538 B2 | 5/2005 | Matoba |
| 6,899,705 B2 | 5/2005 | Niemeyer |
| 6,902,560 B1 | 6/2005 | Morley et al. |
| 6,905,057 B2 | 6/2005 | Swayze et al. |
| 6,936,042 B2 | 8/2005 | Wallace et al. |
| 6,951,535 B2 | 10/2005 | Ghodoussi et al. |
| 6,959,852 B2 | 11/2005 | Shelton, IV et al. |
| 6,964,363 B2 | 11/2005 | Wales et al. |
| 6,969,385 B2 | 11/2005 | Moreyra |
| 6,974,449 B2 | 12/2005 | Niemeyer |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,708 B2 | 2/2006 | Manzo |
| 7,032,798 B2 | 4/2006 | Whitman et al. |
| 7,048,745 B2 | 5/2006 | Tierney et al. |
| RE39,152 E | 6/2006 | Aust et al. |
| 7,055,731 B2 | 6/2006 | Shelton, IV et al. |
| 7,059,508 B2 | 6/2006 | Shelton, IV et al. |
| 7,066,926 B2 | 6/2006 | Wallace et al. |
| 7,077,856 B2 | 7/2006 | Whitman |
| 7,111,769 B2 | 9/2006 | Wales et al. |
| 7,118,582 B1 | 10/2006 | Wang et al. |
| 7,122,029 B2 | 10/2006 | Koop et al. |
| 7,125,403 B2 | 10/2006 | Julian et al. |
| 7,140,528 B2 | 11/2006 | Shelton, IV |
| 7,141,049 B2 | 11/2006 | Stern et al. |
| 7,143,923 B2 | 12/2006 | Shelton, IV et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,155,315 B2 | 12/2006 | Niemeyer et al. |
| 7,172,104 B2 | 2/2007 | Scirica et al. |
| 7,225,964 B2 | 6/2007 | Mastri et al. |
| 7,238,021 B1 | 7/2007 | Johnson |
| 7,239,940 B2 | 7/2007 | Wang et al. |
| 7,246,734 B2 | 7/2007 | Shelton, IV |
| 7,252,660 B2 | 8/2007 | Kunz |
| 7,306,597 B2 | 12/2007 | Manzo |
| 7,328,828 B2 | 2/2008 | Ortiz et al. |
| 7,357,774 B2 | 4/2008 | Cooper |
| 7,364,061 B2 | 4/2008 | Swayze et al. |
| 7,373,219 B2 | 5/2008 | Nowlin et al. |
| 7,379,790 B2 | 5/2008 | Toth et al. |
| 7,380,695 B2 | 6/2008 | Doll et al. |
| 7,380,696 B2 | 6/2008 | Shelton, IV et al. |
| 7,386,365 B2 | 6/2008 | Nixon |
| 7,391,173 B2 | 6/2008 | Schena |
| 7,398,707 B2 | 7/2008 | Morley et al. |
| 7,404,508 B2 | 7/2008 | Smith et al. |
| 7,407,078 B2 | 8/2008 | Shelton, IV et al. |
| 7,413,565 B2 | 8/2008 | Wang et al. |
| 7,416,101 B2 | 8/2008 | Shelton, IV et al. |
| 7,419,080 B2 | 9/2008 | Smith et al. |
| 7,422,139 B2 | 9/2008 | Shelton, IV et al. |
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,453,227 B2 | 11/2008 | Prisco et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,524,320 B2 | 4/2009 | Tierney et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,574,250 B2 | 8/2009 | Niemeyer |
| 7,575,144 B2 | 8/2009 | Ortiz et al. |
| 7,588,175 B2 | 9/2009 | Timm et al. |
| 7,588,176 B2 | 9/2009 | Timm et al. |
| 7,594,912 B2 | 9/2009 | Cooper et al. |
| 7,607,440 B2 | 10/2009 | Coste-Maniere et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,666,191 B2 | 2/2010 | Orban, III et al. |
| 7,670,334 B2 | 3/2010 | Hueil et al. |
| 7,673,780 B2 | 3/2010 | Shelton, IV et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,835 B2 | 4/2010 | Lee et al. |
| 7,699,855 B2 | 4/2010 | Anderson et al. |
| 7,713,263 B2 | 5/2010 | Niemeyer |
| 7,721,931 B2 | 5/2010 | Shelton, IV et al. |
| 7,725,214 B2 | 5/2010 | Diolaiti |
| 7,727,244 B2 | 6/2010 | Orban, III et al. |
| 7,738,971 B2 | 6/2010 | Swayze et al. |
| 7,740,159 B2 | 6/2010 | Shelton, IV et al. |
| 7,741,802 B2 | 6/2010 | Prisco et al. |
| 7,743,960 B2 | 6/2010 | Whitman et al. |
| 7,756,036 B2 | 7/2010 | Druke et al. |
| 7,757,028 B2 | 7/2010 | Druke et al. |
| 7,758,613 B2 | 7/2010 | Whitman |
| 7,762,825 B2 | 7/2010 | Burbank et al. |
| 7,766,210 B2 | 8/2010 | Shelton, IV et al. |
| 7,770,773 B2 | 8/2010 | Whitman et al. |
| 7,770,775 B2 | 8/2010 | Shelton, IV et al. |
| 7,778,733 B2 | 8/2010 | Nowlin et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,822,458 B2 | 10/2010 | Webster, III et al. |
| 7,824,401 B2 | 11/2010 | Manzo et al. |
| 7,835,823 B2 | 11/2010 | Sillman et al. |
| 7,843,158 B2 | 11/2010 | Prisco |
| 7,845,534 B2 | 12/2010 | Viola et al. |
| 7,845,537 B2 | 12/2010 | Shelton, IV et al. |
| 7,857,185 B2 | 12/2010 | Swayze et al. |
| 7,865,266 B2 | 1/2011 | Moll et al. |
| 7,865,269 B2 | 1/2011 | Prisco et al. |
| 7,870,989 B2 | 1/2011 | Viola et al. |
| 7,886,743 B2 | 2/2011 | Cooper et al. |
| 7,899,578 B2 | 3/2011 | Prisco et al. |
| 7,900,805 B2 | 3/2011 | Shelton, IV et al. |
| 7,905,897 B2 | 3/2011 | Whitman et al. |
| 7,907,166 B2 | 3/2011 | Lamprecht et al. |
| 7,918,230 B2 | 4/2011 | Whitman et al. |
| 7,922,061 B2 | 4/2011 | Shelton, IV et al. |
| 7,922,719 B2 | 4/2011 | Ralph et al. |
| 7,935,130 B2 | 5/2011 | Williams |
| 7,947,034 B2 | 5/2011 | Whitman |

(56) References Cited

U.S. PATENT DOCUMENTS

| | | | |
|---|---|---|---|
| 7,951,071 | B2 | 5/2011 | Whitman et al. |
| 7,954,682 | B2 | 6/2011 | Giordano et al. |
| 7,959,051 | B2 | 6/2011 | Smith et al. |
| 7,963,433 | B2 | 6/2011 | Whitman et al. |
| 7,963,913 | B2 | 6/2011 | Devengenzo et al. |
| 7,967,178 | B2 | 6/2011 | Scirica et al. |
| 7,967,179 | B2 | 6/2011 | Olson et al. |
| 7,983,793 | B2 | 7/2011 | Toth et al. |
| 7,992,758 | B2 | 8/2011 | Whitman et al. |
| 8,002,767 | B2 | 8/2011 | Sanchez et al. |
| 8,004,229 | B2 | 8/2011 | Nowlin et al. |
| 8,011,550 | B2 | 9/2011 | Aranyi et al. |
| 8,012,170 | B2 | 9/2011 | Whitman et al. |
| 8,016,178 | B2 | 9/2011 | Olson et al. |
| 8,016,855 | B2 | 9/2011 | Whitman et al. |
| 8,020,743 | B2 | 9/2011 | Shelton, IV |
| 8,025,199 | B2 | 9/2011 | Whitman et al. |
| 8,035,487 | B2 | 10/2011 | Malackowski |
| 8,052,024 | B2 | 11/2011 | Viola et al. |
| 8,054,752 | B2 | 11/2011 | Druke et al. |
| 8,062,288 | B2 | 11/2011 | Cooper et al. |
| 8,079,950 | B2 | 12/2011 | Stern et al. |
| 8,100,133 | B2 | 1/2012 | Mintz et al. |
| 8,108,072 | B2 | 1/2012 | Zhao et al. |
| 8,114,118 | B2 | 2/2012 | Knodel et al. |
| 8,120,301 | B2 | 2/2012 | Goldberg et al. |
| 8,127,975 | B2 | 3/2012 | Olson et al. |
| 8,132,705 | B2 | 3/2012 | Viola et al. |
| 8,142,447 | B2 | 3/2012 | Cooper et al. |
| 8,147,503 | B2 | 4/2012 | Zhao et al. |
| 8,151,661 | B2 | 4/2012 | Schena et al. |
| 8,152,516 | B2 | 4/2012 | Harvey et al. |
| 8,155,479 | B2 | 4/2012 | Hoffman et al. |
| 8,157,150 | B2 | 4/2012 | Viola et al. |
| 8,157,151 | B2 | 4/2012 | Ingmanson et al. |
| 8,182,469 | B2 | 5/2012 | Anderson et al. |
| 8,182,494 | B1 | 5/2012 | Yencho et al. |
| 8,186,555 | B2 | 5/2012 | Shelton, IV et al. |
| 8,186,587 | B2 | 5/2012 | Zmood et al. |
| 8,202,278 | B2 | 6/2012 | Orban, III et al. |
| 8,206,406 | B2 | 6/2012 | Orban, III |
| 8,210,413 | B2 | 7/2012 | Whitman et al. |
| 8,216,250 | B2 | 7/2012 | Orban, III et al. |
| 8,220,367 | B2 | 7/2012 | Hsu |
| 8,220,468 | B2 | 7/2012 | Cooper et al. |
| 8,235,273 | B2 | 8/2012 | Olson et al. |
| 8,241,322 | B2 | 8/2012 | Whitman et al. |
| 8,256,319 | B2 | 9/2012 | Cooper et al. |
| 8,272,554 | B2 | 9/2012 | Whitman et al. |
| 8,285,517 | B2 | 10/2012 | Sillman et al. |
| 8,292,150 | B2 | 10/2012 | Bryant |
| 8,292,888 | B2 | 10/2012 | Whitman |
| 8,315,720 | B2 | 11/2012 | Mohr et al. |
| 8,335,590 | B2 | 12/2012 | Costa et al. |
| 8,342,379 | B2 | 1/2013 | Whitman et al. |
| 8,347,757 | B2 | 1/2013 | Duval |
| 8,348,130 | B2 | 1/2013 | Shah et al. |
| 8,348,855 | B2 | 1/2013 | Hillely et al. |
| 8,353,440 | B2 | 1/2013 | Whitman et al. |
| 8,357,144 | B2 | 1/2013 | Whitman et al. |
| 8,365,633 | B2 | 2/2013 | Simaan et al. |
| 8,365,972 | B2 | 2/2013 | Aranyi et al. |
| 8,371,492 | B2 | 2/2013 | Aranyi et al. |
| 8,372,057 | B2 | 2/2013 | Cude et al. |
| 8,374,723 | B2 | 2/2013 | Zhao et al. |
| 8,391,957 | B2 | 3/2013 | Carlson et al. |
| 8,403,926 | B2 | 3/2013 | Nobis et al. |
| 8,418,073 | B2 | 4/2013 | Mohr et al. |
| 8,418,904 | B2 | 4/2013 | Wenchell et al. |
| 8,419,717 | B2 | 4/2013 | Diolaiti et al. |
| 8,423,182 | B2 | 4/2013 | Robinson et al. |
| 8,424,739 | B2 | 4/2013 | Racenet et al. |
| 8,452,447 | B2 | 5/2013 | Nixon |
| 8,454,585 | B2 | 6/2013 | Whitman |
| 8,499,992 | B2 | 8/2013 | Whitman et al. |
| 8,505,802 | B2 | 8/2013 | Viola et al. |
| 8,508,173 | B2 | 8/2013 | Goldberg et al. |
| 8,517,241 | B2 | 8/2013 | Nicholas et al. |
| 8,523,043 | B2 | 9/2013 | Ullrich et al. |
| 8,528,440 | B2 | 9/2013 | Morley et al. |
| 8,529,582 | B2 | 9/2013 | Devengenzo et al. |
| 8,540,748 | B2 | 9/2013 | Murphy et al. |
| 8,551,076 | B2 | 10/2013 | Duval et al. |
| 8,551,116 | B2 | 10/2013 | Julian et al. |
| 8,561,871 | B2 | 10/2013 | Rajappa et al. |
| 8,561,874 | B2 | 10/2013 | Scirica |
| 8,562,594 | B2 | 10/2013 | Cooper et al. |
| 8,594,841 | B2 | 11/2013 | Zhao et al. |
| 8,597,182 | B2 | 12/2013 | Stein et al. |
| 8,597,280 | B2 | 12/2013 | Cooper et al. |
| 8,600,551 | B2 | 12/2013 | Itkowitz et al. |
| 8,602,287 | B2 | 12/2013 | Yates et al. |
| 8,608,773 | B2 | 12/2013 | Tierney et al. |
| 8,620,473 | B2 | 12/2013 | Diolaiti et al. |
| 8,623,000 | B2 | 1/2014 | Humayun et al. |
| 8,624,537 | B2 | 1/2014 | Nowlin et al. |
| 8,627,995 | B2 | 1/2014 | Smith et al. |
| 8,632,463 | B2 | 1/2014 | Drinan et al. |
| 8,634,957 | B2 | 1/2014 | Toth et al. |
| 8,636,766 | B2 | 1/2014 | Milliman et al. |
| 8,638,056 | B2 | 1/2014 | Goldberg et al. |
| 8,638,057 | B2 | 1/2014 | Goldberg et al. |
| 8,644,988 | B2 | 2/2014 | Prisco et al. |
| 8,647,258 | B2 | 2/2014 | Aranyi et al. |
| 8,652,121 | B2 | 2/2014 | Quick et al. |
| 8,657,174 | B2 | 2/2014 | Yates et al. |
| 8,657,177 | B2 | 2/2014 | Scirica et al. |
| 8,666,544 | B2 | 3/2014 | Moll et al. |
| 8,668,638 | B2 | 3/2014 | Donhowe et al. |
| 8,672,206 | B2 | 3/2014 | Aranyi et al. |
| 8,696,552 | B2 | 4/2014 | Whitman |
| 8,708,213 | B2 | 4/2014 | Shelton, IV et al. |
| 8,715,306 | B2 | 5/2014 | Faller et al. |
| 8,746,252 | B2 | 6/2014 | McGrogan et al. |
| 8,749,189 | B2 | 6/2014 | Nowlin et al. |
| 8,749,190 | B2 | 6/2014 | Nowlin et al. |
| 8,758,352 | B2 | 6/2014 | Cooper et al. |
| 8,758,391 | B2 | 6/2014 | Swayze et al. |
| 8,761,930 | B2 | 6/2014 | Nixon |
| 8,768,516 | B2 | 7/2014 | Diolaiti et al. |
| 8,786,241 | B2 | 7/2014 | Nowlin et al. |
| 8,790,243 | B2 | 7/2014 | Cooper et al. |
| 8,806,973 | B2 | 8/2014 | Ross et al. |
| 8,808,164 | B2 | 8/2014 | Hoffman et al. |
| 8,808,311 | B2 | 8/2014 | Heinrich et al. |
| 8,816,628 | B2 | 8/2014 | Nowlin et al. |
| 8,820,605 | B2 | 9/2014 | Shelton, IV |
| 8,821,480 | B2 | 9/2014 | Burbank |
| 8,823,308 | B2 | 9/2014 | Nowlin et al. |
| 8,827,989 | B2 | 9/2014 | Niemeyer |
| 8,838,270 | B2 | 9/2014 | Druke et al. |
| 8,851,355 | B2 | 10/2014 | Aranyi et al. |
| 8,852,174 | B2 | 10/2014 | Burbank |
| 8,858,547 | B2 | 10/2014 | Brogna |
| 8,858,571 | B2 | 10/2014 | Shelton, IV et al. |
| 8,862,268 | B2 | 10/2014 | Robinson et al. |
| 8,864,751 | B2 | 10/2014 | Prisco et al. |
| 8,864,752 | B2 | 10/2014 | Diolaiti et al. |
| 8,875,972 | B2 | 11/2014 | Weisenburgh, II et al. |
| 8,888,762 | B2 | 11/2014 | Whitman |
| 8,893,946 | B2 | 11/2014 | Boudreaux et al. |
| 8,899,462 | B2 | 12/2014 | Kostrzewski et al. |
| 8,903,546 | B2 | 12/2014 | Diolaiti et al. |
| 8,903,549 | B2 | 12/2014 | Itkowitz et al. |
| 8,905,289 | B2 | 12/2014 | Patel et al. |
| 8,911,428 | B2 | 12/2014 | Cooper et al. |
| 8,912,746 | B2 | 12/2014 | Reid et al. |
| 8,919,630 | B2 | 12/2014 | Milliman |
| 8,931,680 | B2 | 1/2015 | Milliman |
| 8,939,344 | B2 | 1/2015 | Olson et al. |
| 8,944,070 | B2 | 2/2015 | Guthart et al. |
| 8,950,646 | B2 | 2/2015 | Viola |
| 8,960,519 | B2 | 2/2015 | Whitman et al. |
| 8,961,396 | B2 | 2/2015 | Azarbarzin et al. |

(56) References Cited

U.S. PATENT DOCUMENTS

| | | | |
|---|---|---|---|
| 8,967,443 B2 | 3/2015 | McCuen |
| 8,968,276 B2 | 3/2015 | Zemlok et al. |
| 8,968,337 B2 | 3/2015 | Whitfield et al. |
| 8,989,903 B2 | 3/2015 | Weir et al. |
| 8,992,422 B2 | 3/2015 | Spivey et al. |
| 9,002,518 B2 | 4/2015 | Manzo et al. |
| 9,014,856 B2 | 4/2015 | Manzo et al. |
| 9,016,540 B2 | 4/2015 | Whitman et al. |
| 9,016,545 B2 | 4/2015 | Aranyi et al. |
| 9,019,345 B2 | 4/2015 | Patrick |
| 9,023,014 B2 | 5/2015 | Chowaniec et al. |
| 9,033,868 B2 | 5/2015 | Whitman et al. |
| 9,043,027 B2 | 5/2015 | Durant et al. |
| 9,050,120 B2 | 6/2015 | Swarup et al. |
| 9,055,943 B2 | 6/2015 | Zemlok et al. |
| 9,055,961 B2 | 6/2015 | Manzo et al. |
| 9,064,653 B2 | 6/2015 | Prest et al. |
| 9,068,628 B2 | 6/2015 | Solomon et al. |
| 9,072,515 B2 | 7/2015 | Hall et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,847 B2 | 8/2015 | Whitman et al. |
| 9,113,875 B2 | 8/2015 | Viola et al. |
| 9,113,876 B2 | 8/2015 | Zemlok et al. |
| 9,113,877 B1 | 8/2015 | Whitman et al. |
| 9,113,899 B2 | 8/2015 | Garrison et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,216,013 B2 | 12/2015 | Scirica et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,712 B2 | 1/2016 | Zemlok et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,282,961 B2 | 3/2016 | Whitman et al. |
| 9,282,963 B2 | 3/2016 | Bryant |
| 9,283,049 B2 | 3/2016 | Diolaiti et al. |
| 9,295,522 B2 | 3/2016 | Kostrzewski |
| 9,301,811 B2 | 4/2016 | Goldberg et al. |
| 9,307,986 B2 | 4/2016 | Hall et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti et al. |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,937,626 B2 * | 4/2018 | Rockrohr ............. B25J 15/0226 |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin et al. |
| 10,179,413 B2 | 1/2019 | Rockrohr |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |

(56) References Cited

U.S. PATENT DOCUMENTS

| | | |
|---|---|---|
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2001/0031975 A1 | 10/2001 | Whitman et al. |
| 2002/0049454 A1 | 4/2002 | Whitman et al. |
| 2002/0111621 A1 | 8/2002 | Wallace et al. |
| 2002/0120254 A1* | 8/2002 | Julian ................ A61B 34/76 606/1 |
| 2002/0165541 A1 | 11/2002 | Whitman |
| 2003/0038938 A1 | 2/2003 | Jung et al. |
| 2003/0165794 A1 | 9/2003 | Matoba |
| 2004/0034369 A1 | 2/2004 | Sauer et al. |
| 2004/0111012 A1 | 6/2004 | Whitman |
| 2004/0133189 A1 | 7/2004 | Sakurai |
| 2004/0153124 A1 | 8/2004 | Whitman |
| 2004/0176751 A1 | 9/2004 | Weitzner et al. |
| 2004/0193146 A1* | 9/2004 | Lee .................. A61B 17/062 606/1 |
| 2005/0125027 A1 | 6/2005 | Knodel et al. |
| 2005/0131442 A1 | 6/2005 | Yachia et al. |
| 2006/0074415 A1 | 4/2006 | Scott et al. |
| 2006/0142656 A1 | 6/2006 | Malackowski et al. |
| 2006/0142740 A1 | 6/2006 | Sherman et al. |
| 2006/0142744 A1 | 6/2006 | Boutoussov |
| 2006/0259073 A1 | 11/2006 | Miyamoto et al. |
| 2006/0278680 A1 | 12/2006 | Viola et al. |
| 2006/0284730 A1 | 12/2006 | Schmid et al. |
| 2007/0023476 A1 | 2/2007 | Whitman et al. |
| 2007/0023477 A1 | 2/2007 | Whitman et al. |
| 2007/0029363 A1 | 2/2007 | Popov |
| 2007/0084897 A1 | 4/2007 | Shelton et al. |
| 2007/0102472 A1 | 5/2007 | Shelton |
| 2007/0123855 A1 | 5/2007 | Morley et al. |
| 2007/0152014 A1 | 7/2007 | Gillum et al. |
| 2007/0175947 A1 | 8/2007 | Ortiz et al. |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0175961 A1 | 8/2007 | Shelton et al. |
| 2007/0270784 A1 | 11/2007 | Smith et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0058801 A1 | 3/2008 | Taylor et al. |
| 2008/0108443 A1 | 5/2008 | Jinno et al. |
| 2008/0109012 A1 | 5/2008 | Falco et al. |
| 2008/0110958 A1 | 5/2008 | McKenna et al. |
| 2008/0147089 A1 | 6/2008 | Loh et al. |
| 2008/0167736 A1 | 7/2008 | Swayze et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0237296 A1 | 10/2008 | Boudreaux et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0262654 A1 | 10/2008 | Omori et al. |
| 2008/0308603 A1 | 12/2008 | Shelton et al. |
| 2009/0012533 A1 | 1/2009 | Barbagli et al. |
| 2009/0090763 A1 | 4/2009 | Zemlok et al. |
| 2009/0099876 A1 | 4/2009 | Whitman |
| 2009/0138006 A1 | 5/2009 | Bales et al. |
| 2009/0171147 A1 | 7/2009 | Lee et al. |
| 2009/0182193 A1 | 7/2009 | Whitman et al. |
| 2009/0209946 A1 | 8/2009 | Swayze et al. |
| 2009/0209990 A1 | 8/2009 | Yates et al. |
| 2009/0254094 A1 | 10/2009 | Knapp et al. |
| 2009/0299141 A1 | 12/2009 | Downey et al. |
| 2010/0023022 A1 | 1/2010 | Zeiner et al. |
| 2010/0069942 A1 | 3/2010 | Shelton, IV |
| 2010/0193568 A1 | 8/2010 | Scheib et al. |
| 2010/0211053 A1 | 8/2010 | Ross et al. |
| 2010/0225073 A1 | 9/2010 | Porter et al. |
| 2011/0071508 A1 | 3/2011 | Duval et al. |
| 2011/0077673 A1 | 3/2011 | Grubac et al. |
| 2011/0121049 A1 | 5/2011 | Malinouskas et al. |
| 2011/0125138 A1 | 5/2011 | Malinouskas et al. |
| 2011/0139851 A1 | 6/2011 | McCuen |
| 2011/0155783 A1 | 6/2011 | Rajappa et al. |
| 2011/0155786 A1 | 6/2011 | Shelton, IV |
| 2011/0172648 A1 | 7/2011 | Jeong |
| 2011/0174009 A1 | 7/2011 | Iizuka et al. |
| 2011/0174099 A1 | 7/2011 | Ross et al. |
| 2011/0184245 A1 | 7/2011 | Xia et al. |
| 2011/0204119 A1 | 8/2011 | McCuen |
| 2011/0218522 A1 | 9/2011 | Whitman |
| 2011/0276057 A1 | 11/2011 | Conlon et al. |
| 2011/0290854 A1 | 12/2011 | Timm et al. |
| 2011/0295242 A1 | 12/2011 | Spivey et al. |
| 2011/0295269 A1 | 12/2011 | Swensgard et al. |
| 2011/0301637 A1 | 12/2011 | Kerr et al. |
| 2012/0000962 A1 | 1/2012 | Racenet et al. |
| 2012/0074199 A1 | 3/2012 | Olson et al. |
| 2012/0089131 A1 | 4/2012 | Zemlok et al. |
| 2012/0104071 A1 | 5/2012 | Bryant |
| 2012/0116368 A1 | 5/2012 | Viola |
| 2012/0116416 A1 | 5/2012 | Neff et al. |
| 2012/0143002 A1 | 6/2012 | Aranyi et al. |
| 2012/0158013 A1 | 6/2012 | Stefanchik et al. |

(56) References Cited

U.S. PATENT DOCUMENTS

| | | |
|---|---|---|
| 2012/0172924 A1 | 7/2012 | Allen, IV |
| 2012/0211542 A1 | 8/2012 | Racenet |
| 2012/0223121 A1 | 9/2012 | Viola et al. |
| 2012/0245428 A1 | 9/2012 | Smith et al. |
| 2012/0253329 A1 | 10/2012 | Zemlok et al. |
| 2012/0310220 A1 | 12/2012 | Malkowski et al. |
| 2012/0323226 A1 | 12/2012 | Chowaniec et al. |
| 2012/0330285 A1 | 12/2012 | Hartoumbekis et al. |
| 2012/0330287 A1 | 12/2012 | Yim |
| 2013/0093149 A1 | 4/2013 | Saur et al. |
| 2013/0110131 A1 | 5/2013 | Madhani et al. |
| 2013/0140835 A1* | 6/2013 | Stefanchik ............. A61B 17/29 294/106 |
| 2013/0181035 A1 | 7/2013 | Milliman |
| 2013/0184704 A1 | 7/2013 | Beardsley et al. |
| 2013/0214025 A1 | 8/2013 | Zemlok et al. |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0319706 A1 | 12/2013 | Nicholas et al. |
| 2013/0324978 A1 | 12/2013 | Nicholas et al. |
| 2013/0324979 A1 | 12/2013 | Nicholas et al. |
| 2013/0334281 A1 | 12/2013 | Williams |
| 2014/0012236 A1 | 1/2014 | Williams et al. |
| 2014/0012237 A1 | 1/2014 | Pribanic et al. |
| 2014/0012289 A1 | 1/2014 | Snow et al. |
| 2014/0025046 A1 | 1/2014 | Williams et al. |
| 2014/0110455 A1 | 4/2014 | Ingmanson et al. |
| 2014/0207125 A1 | 7/2014 | Applegate et al. |
| 2014/0207182 A1 | 7/2014 | Zergiebel et al. |
| 2014/0207185 A1 | 7/2014 | Goble et al. |
| 2014/0236174 A1 | 8/2014 | Williams et al. |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0358129 A1 | 12/2014 | Zergiebel et al. |
| 2014/0361068 A1 | 12/2014 | Aranyi et al. |
| 2014/0365235 A1 | 12/2014 | DeBoer et al. |
| 2014/0373652 A1 | 12/2014 | Zergiebel et al. |
| 2015/0014392 A1 | 1/2015 | Williams et al. |
| 2015/0048144 A1 | 2/2015 | Whitman |
| 2015/0076205 A1 | 3/2015 | Zergiebel |
| 2015/0080912 A1 | 3/2015 | Sapre |
| 2015/0112381 A1 | 4/2015 | Richard |
| 2015/0122870 A1 | 5/2015 | Zemlok et al. |
| 2015/0133224 A1 | 5/2015 | Whitman et al. |
| 2015/0150547 A1 | 6/2015 | Ingmanson et al. |
| 2015/0150574 A1 | 6/2015 | Richard et al. |
| 2015/0157320 A1 | 6/2015 | Zergiebel et al. |
| 2015/0157321 A1 | 6/2015 | Zergiebel et al. |
| 2015/0164502 A1 | 6/2015 | Richard et al. |
| 2015/0201931 A1 | 7/2015 | Zergiebel et al. |
| 2015/0209965 A1 | 7/2015 | Low |
| 2015/0272577 A1 | 10/2015 | Zemlok et al. |
| 2015/0297199 A1 | 10/2015 | Nicholas et al. |
| 2015/0303996 A1 | 10/2015 | Calderoni |
| 2015/0320420 A1 | 11/2015 | Penna et al. |
| 2015/0327850 A1 | 11/2015 | Kostrzewski |
| 2015/0342601 A1 | 12/2015 | Williams et al. |
| 2015/0342603 A1 | 12/2015 | Zergiebel et al. |
| 2015/0374366 A1 | 12/2015 | Zergiebel et al. |
| 2015/0374370 A1 | 12/2015 | Zergiebel et al. |
| 2015/0374371 A1 | 12/2015 | Richard et al. |
| 2015/0374372 A1 | 12/2015 | Zergiebel et al. |
| 2015/0374449 A1 | 12/2015 | Chowaniec et al. |
| 2015/0380187 A1 | 12/2015 | Zergiebel et al. |
| 2016/0095585 A1 | 4/2016 | Zergiebel et al. |
| 2016/0095596 A1 | 4/2016 | Scirica et al. |
| 2016/0106406 A1 | 4/2016 | Cabrera et al. |
| 2016/0113648 A1 | 4/2016 | Zergiebel et al. |
| 2016/0113649 A1 | 4/2016 | Zergiebel et al. |
| 2016/0310156 A1 | 10/2016 | Kapadia |
| 2017/0014197 A1 | 1/2017 | McCrea |

FOREIGN PATENT DOCUMENTS

| | | |
|---|---|---|
| CN | 1957854 A | 5/2007 |
| CN | 101495046 A | 7/2009 |
| CN | 101522128 A | 9/2009 |
| CN | 101612053 A | 12/2009 |
| CN | 102247182 A | 11/2011 |
| CN | 103110456 A | 5/2013 |
| DE | 102008053842 A1 | 5/2010 |
| EP | 0705571 A1 | 4/1996 |
| EP | 1563793 A1 | 8/2005 |
| EP | 1769754 A1 | 4/2007 |
| EP | 2316345 A1 | 5/2011 |
| EP | 2668910 A2 | 12/2013 |
| ES | 2333509 A1 | 2/2010 |
| JP | 2005125075 A | 5/2005 |
| KR | 20120022521 A | 3/2012 |
| WO | 2011108840 A2 | 9/2011 |
| WO | 2012040984 A1 | 4/2012 |

OTHER PUBLICATIONS

European Search Report issued in European Application No. 19188190.3 dated Oct. 11, 2019, 7 pages.
Extended European Search Report corresponding to counterpart International Application No. EP 14 18 4882.0 dated May 12, 2015.
Canadian Office Action corresponding to counterpart International Application No. CA 2640399 dated May 7, 2015.
Japanese Office Action corresponding to counterpart International Application No. JP 2011-197365 dated Mar. 23, 2015.
Japanese Office Action corresponding to counterpart International Application No. JP 2011-084092 dated May 20, 2015.
Japanese Office Action corresponding to counterpart International Application No. JP 2014-148482 dated Jun. 2, 2015.
Extended European Search Report corresponding to counterpart International Application No. EP 14 18 9358.6 dated Jul. 8, 2015.
Extended European Search Report corresponding to counterpart International Application No. EP 14 19 6148.2 dated Apr. 23, 2015.
Partial European Search Report corresponding to counterpart International Application No. EP 14 19 6704.2 dated May 11, 2015.
Australian Office Action corresponding to counterpart International Application No. AU 2010241367 dated Aug. 20, 2015.
Partial European Search Report corresponding to counterpart International Application No. EP 14 19 97833 dated Sep. 3, 2015.
Extended European Search Report corresponding to counterpart International Application No. EP 15 16 9962.6 dated Sep. 14, 2015.
Extended European Search Report corresponding to International Application No. EP 15 15 1076.5 dated Apr. 22, 2015.
Japanese Office Action corresponding to International Application No. JP 2011-084092 dated Jan. 14, 2016.
Extended European Search Report corresponding to International Application No. EP 12 19 7970.2 dated Jan. 28, 2016.
Chinese Office Action corresponding to International Application No. CN 201210560638.1 dated Oct. 21, 2015.
European Office Action corresponding to International Application No. EP 14 15 9056.2 dated Oct. 26, 2015.
Australian Examination Report No. 1 corresponding to International Application No. AU 2015200153 dated Dec. 11, 2015.
Australian Examination Report No. 1 corresponding to International Application No. AU 2014204542 dated Jan. 7, 2016.
Chinese Office Action corresponding to International Application No. CN 201310125449.6 dated Feb. 3, 2016.
Extended European Search Report corresponding to International Application No. EP 15 19 0245.9 dated Jan. 28, 2016.
Extended European Search Report corresponding to International Application No. EP 15 16 7793.7 dated Apr. 5, 2016.
European Office Action corresponding to International Application No. EP 14 18 4882.0 dated Apr. 25, 2016.
Extended European Search Report corresponding to International Application No. EP 14 19 6704.2 dated Sep. 24, 2015.
International Search Report and Written Opinion corresponding to Int'l Appln. No. PCT/US2015/051837, dated Dec. 21, 2015.

(56) References Cited

OTHER PUBLICATIONS

Extended European Search Report corresponding to International Application No. EP 14 19 7563.1 dated Aug. 5, 2015.
Partial European Search Report corresponding to International Application No. EP 15 19 0643.5 dated Feb. 26, 2016.
Extended European Search Report corresponding to International Application No. EP 15 16 6899.3 dated Feb. 3, 2016.
Extended European Search Report corresponding to International Application No. EP 14 19 9783.3 dated Dec. 22, 2015.
Extended European Search Report corresponding to International Application No. EP 15 17 3807.7 dated Nov. 24, 2015.
Extended European Search Report corresponding to International Application No. EP 15 19 0760.7 dated Apr. 1, 2016.
Extended European Search Report corresponding to International Application No. EP 15 17 3803.6 dated Nov. 24, 2015.
Extended European Search Report corresponding to International Application No. EP 15 17 3804.4 dated Nov. 24, 2015.
Extended European Search Report corresponding to International Application No. EP 15 18 8539.9 dated Feb. 17, 2016.
Extended European Search Report corresponding to International Application No. EP 15 17 3910.9 dated Nov. 13, 2015.
European Office Action corresponding to International Application No. EP 14 15 2236.7 dated Aug. 11, 2015.
Extended European Search Report corresponding to International Application No. EP 15 18 4915.5 dated Jan. 5, 2016.
Office Action corresponding to counterpart Int'l Appln. No. CN 201310369318.2 dated Jun. 28, 2016.
Chinese Office Action (with English translation), dated Jul. 4, 2016, corresponding to Chinese Patent Application No. 2015101559718; 23 total pages.
International Search Report corresponding to PCT/US2014/061329 dated Jan. 28, 2015.
Extended European Search Report corresponding to European Application No. 14868810.4 dated Jul. 27, 2017.
International Search Report for (PCT/US2014/061329) dated Jan. 28, 2015 (4 pages).
Chinese Office Action issued in Chinese Application No. 2014800677212 dated May 22, 2018.
Extended European Search Report for application No. 21154260 dated May 19, 2021.
Chinese Office Action dated May 11, 2022 for application No. 2019103228793 with English translation.

* cited by examiner

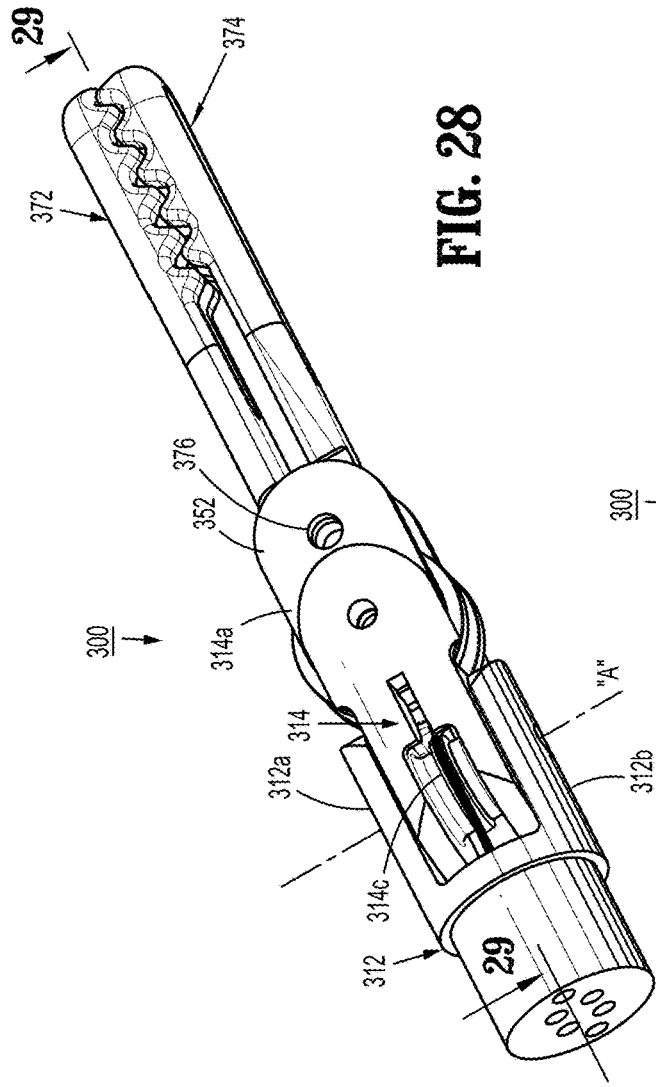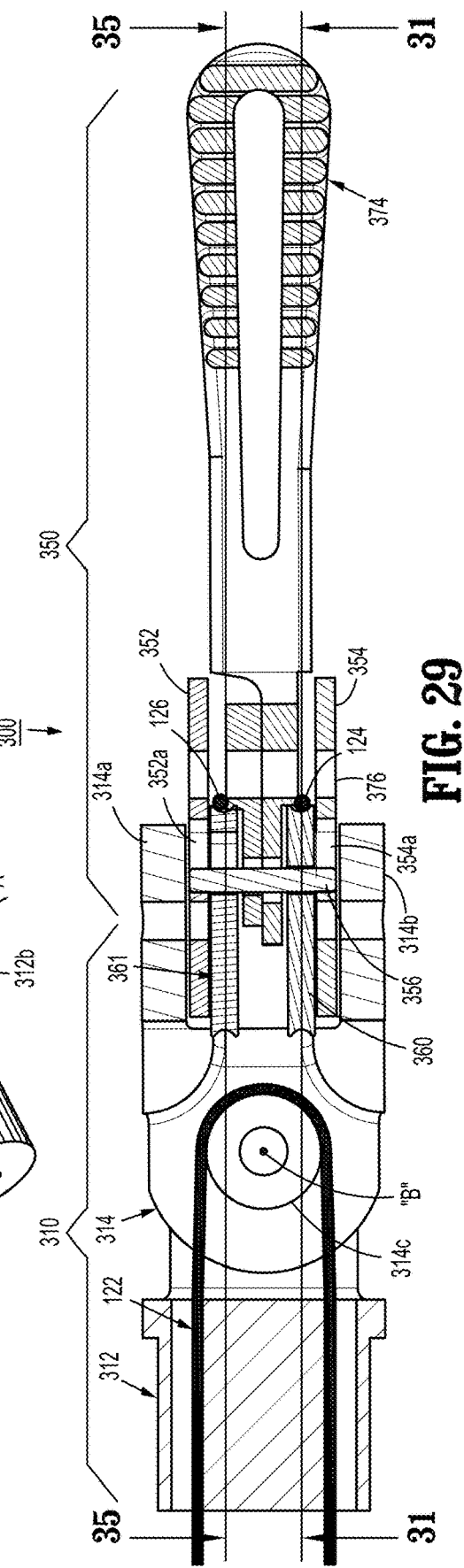

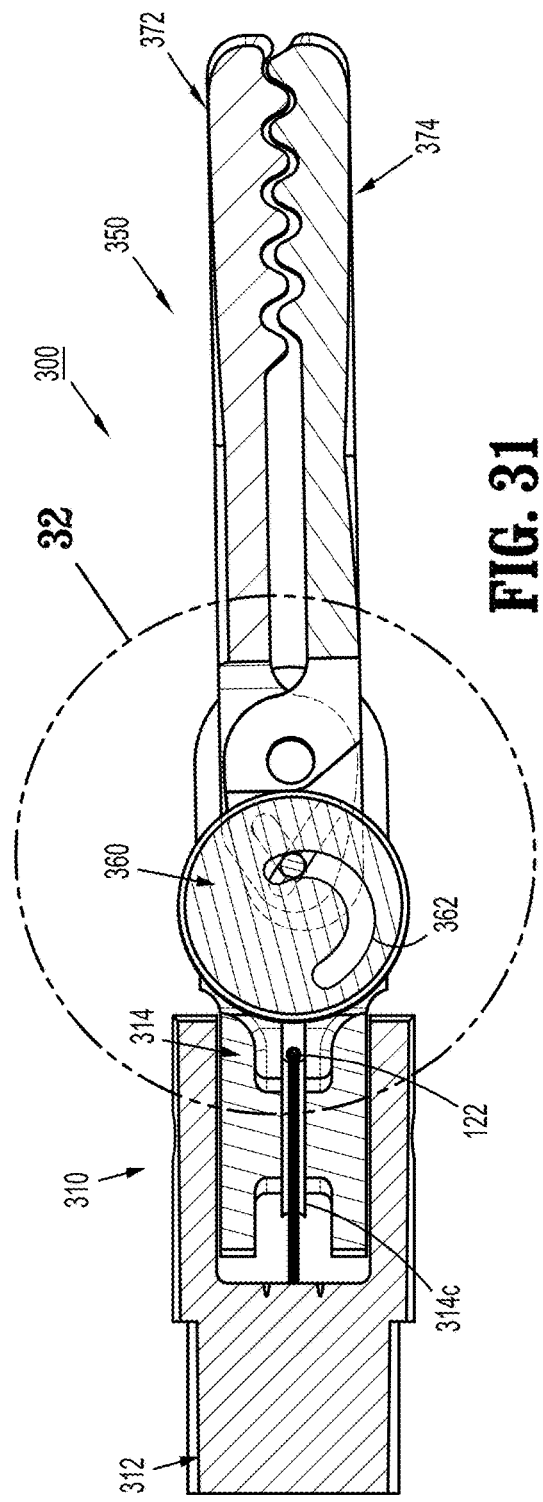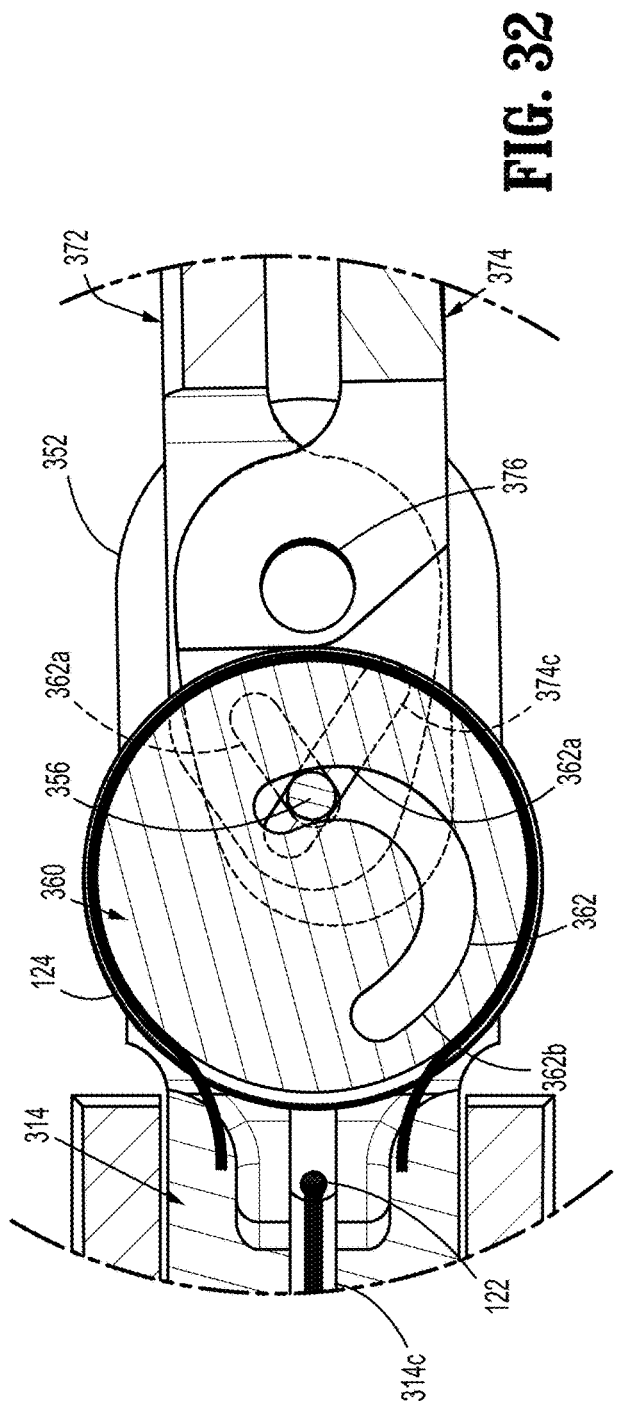

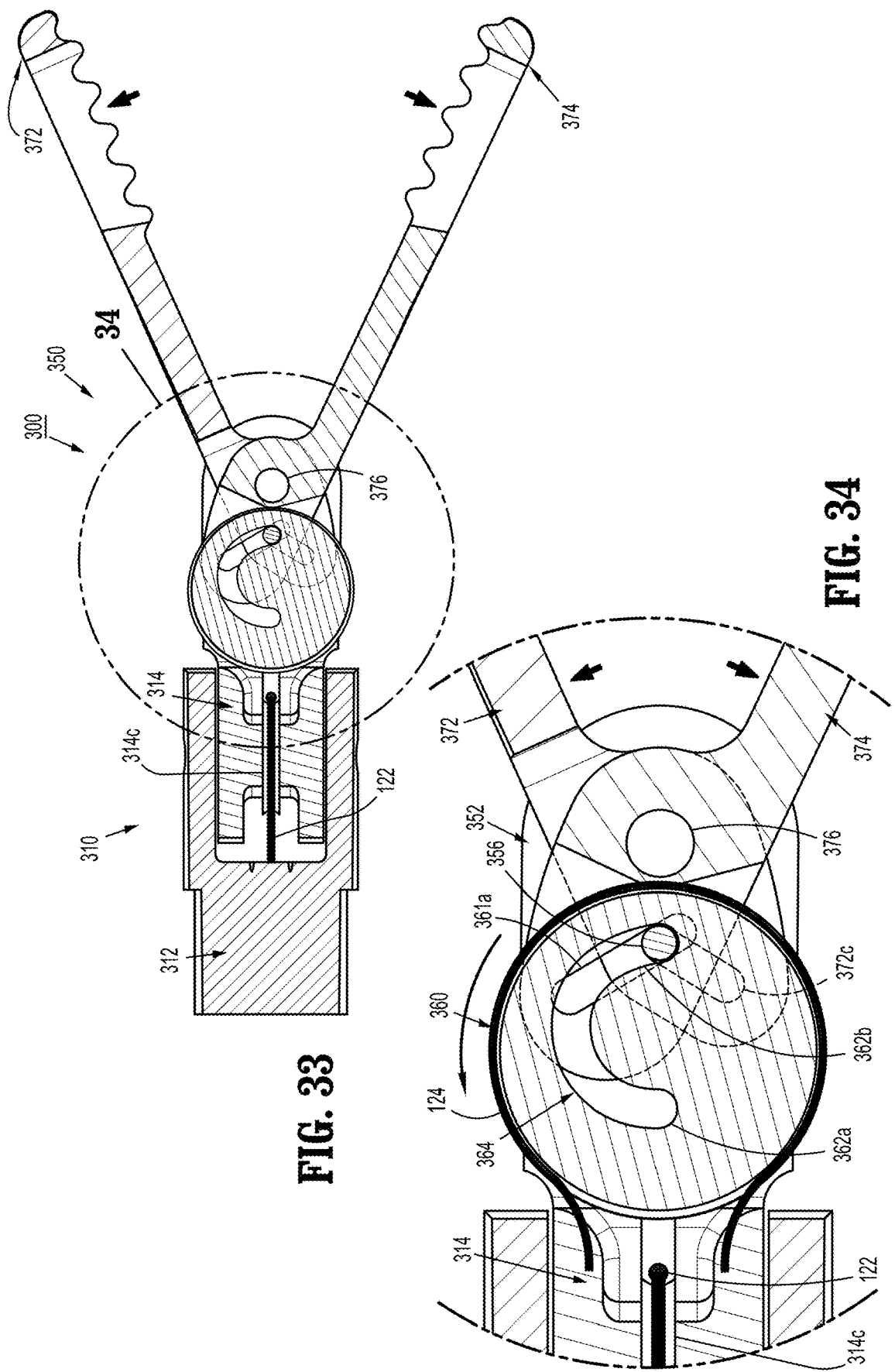

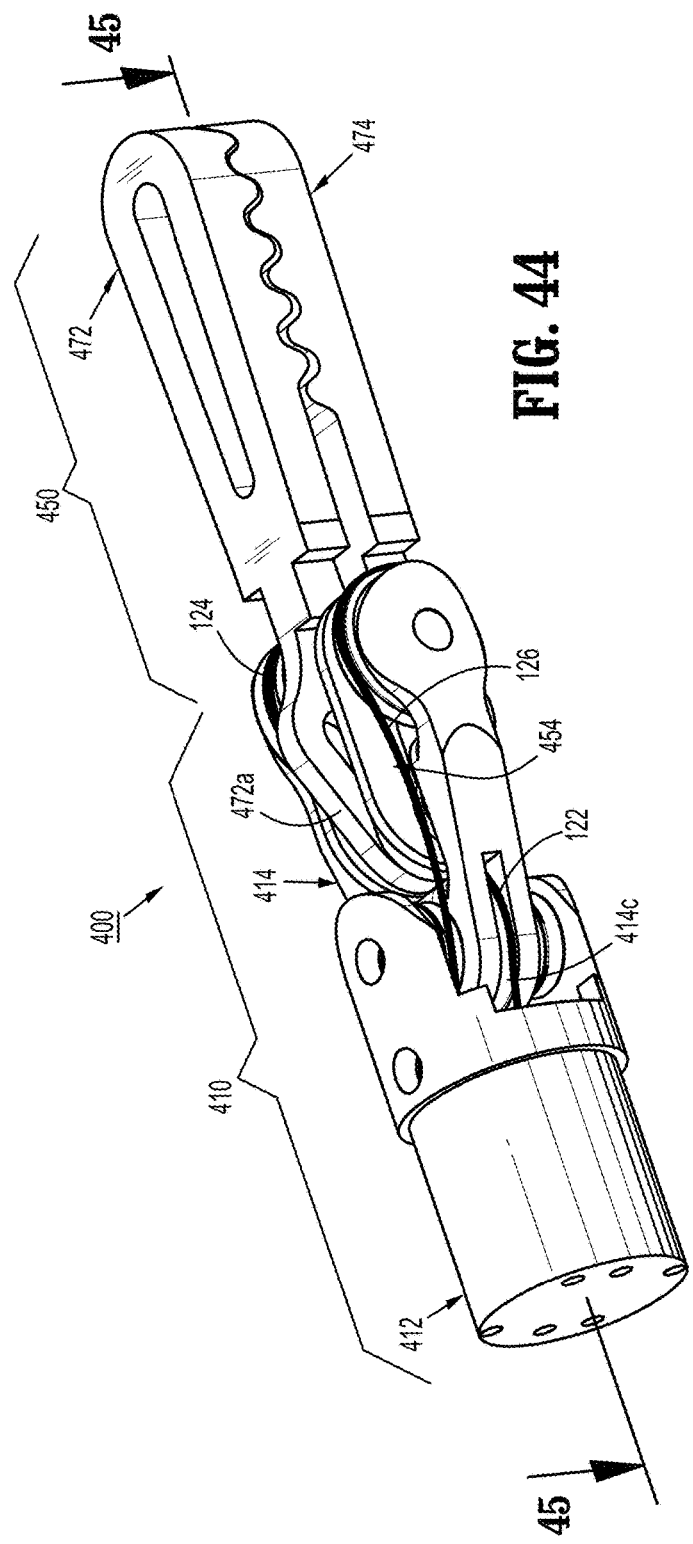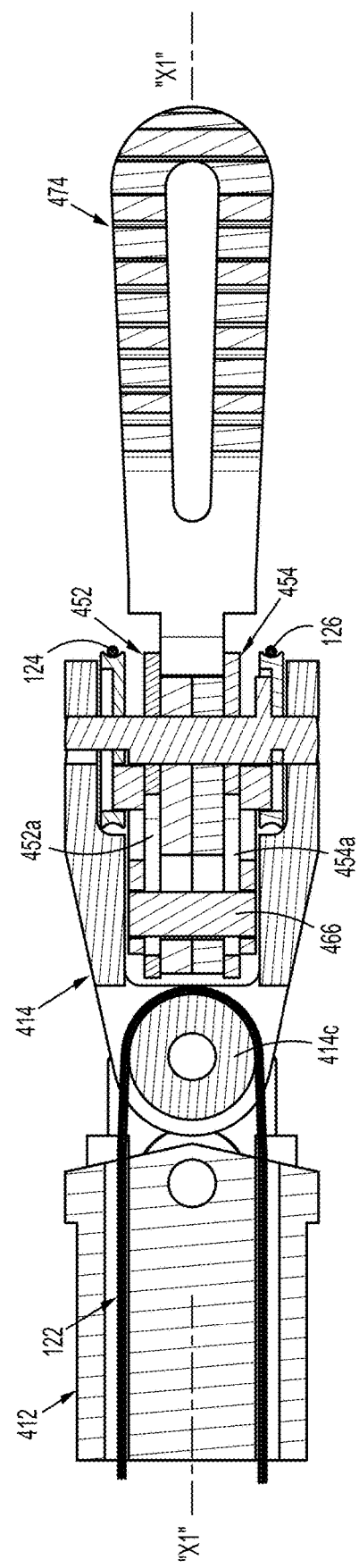

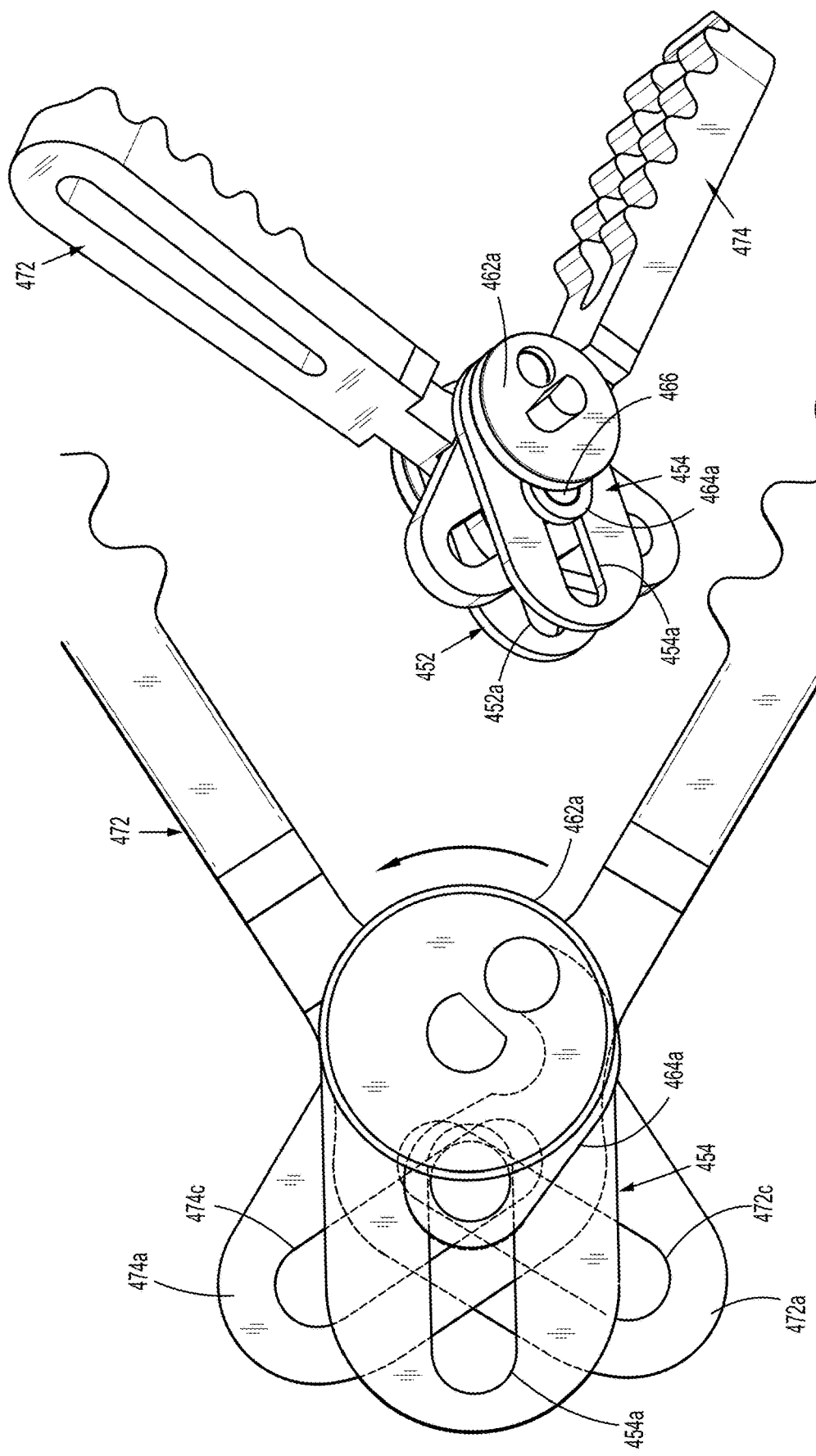

WRIST AND JAW ASSEMBLIES FOR ROBOTIC SURGICAL SYSTEMS

CROSS-REFERENCE TO RELATED APPLICATIONS

This application is a continuation of U.S. patent application Ser. No. 15/921,093, filed Mar. 14, 2018, which is a continuation of U.S. patent application Ser. No. 15/102,081, filed Jun. 6, 2016, which is a U.S. National Stage Application filed under 35 U.S.C. § 371(a) of International Patent Application Serial No. PCT/US2014/061329, filed Oct. 20, 2014, which claims the benefit U.S. Provisional Patent Application Ser. No. 61/914,632, filed Dec. 11, 2013, the entire disclosure of each of which is incorporated by reference herein.

BACKGROUND

Robotic surgical systems have been used in minimally invasive medical procedures. Some robotic surgical systems included a console supporting a robot arm, and at least one end effector such as forceps or a grasping tool that is mounted to the robot arm via a wrist assembly. During a medical procedure, the end effector and the wrist assembly were inserted into a small incision (via a cannula) or a natural orifice of a patient to position the end effector at a work site within the body of the patient.

Cables extended from the robot console, through the robot arm, and connected to the wrist assembly and/or end effector. In some instances, the cables were actuated by means of motors that were controlled by a processing system including a user interface for a surgeon or clinician to be able to control the robotic surgical system including the robot arm, the wrist assembly and/or the end effector.

In some instances, the wrist assembly provided three degrees of freedom for movement of the end effector through the use of three cables or cable pairs, one for each degree of freedom. For example, for grasping or cutting end effectors the wrist assembly provided the three degrees of freedom by allowing changes to a pitch, a yaw, and an opening and closing of the end effector.

As demand for smaller surgical tools increased, device manufacturers developed surgical tools such as grasping and cutting tools having smaller cross-sectional areas. These smaller cross-sectional areas reduced the total force that could be applied between two jaws at the end of the tools. Additionally, the use of three cables or cable pairs to provide three degrees of motion required a minimum cross-sectional area to implement and limit the ability to further reduce the cross sectional area of these tools. Finally, the force that was applied was not customizable to provide varying forces depending on the position of the jaws in relation to each other as the jaws are opened and closed.

There is a need for surgical tools having small cross-sectional areas that are able to provide high forces between end effector jaws, including customizable forces that vary depending on the position of the jaws in relation to each other.

SUMMARY

Jaws at the end of surgical robotics tools, such as forceps or scissor cutting tools, may be driven by a cable and pulley system that includes at least one cam. In some instances, the cable and pulley system may be driven directly so at least one cable controls a pitch, at least one cable controls a yaw, and at least one cable opens and closes the jaws. In other instances, the cable and pulley system may be differentially driven so that the ends of two cables may be used to control the pitch, yaw, and opening and closing of the jaws. Using a differential drive design may eliminate the need for one cable since only two cables are needed to provide three degrees of freedom (pitch, yaw, and opening and closing of the grasper). Eliminating one cable may therefore reduce the overall cross-sectional area of the tool that is needed to accommodate the cables.

In some instances, at least one of the pulleys may include a cam profile offset from a center of rotation of the pulley. A force may be applied to the pulley by a cable wrapped at least partially around the pulley. The applied force may cause the pulley to move and change a position of the cam profile. A pin or follower may pass through the cam profile and may couple both jaws to the cam profile in a way that enables the jaws to open and close in tandem as the cam profile position is changed and the follower traces the cam profile.

Offsetting the cam profile from the center of rotation of the pulley may increase the overall force applied to the jaws when opening and closing the jaws. As the distance from the center of rotation of the pulley increases, the amount of additional force that is applied to the jaws also increases. This allows higher forces to be applied to the jaws without necessitating a substantial increase to the overall cross-sectional area of the tool. Additionally, changing the shape and location of the cam profile may result in varying amounts of force being applied to the jaws depending on the current position of the follower in the cam profile. A user may select the forces applied to the jaws during different stages of opening and closing of the jaws by customizing the cam profile.

End effectors, including wrist assemblies and jaw assemblies, may be used with and actuated by robotic surgical systems. In some instances, an end effector may be controlled and/or articulated by at least one cable extending from a respective motor of a control device of the robot surgical system. The end effector may include a wrist assembly including a proximal hub defining a longitudinal axis. The end effector may also include a distal hub pivotally connected to the proximal hub. The distal hub may define a longitudinal axis, and the proximal hub and the distal hub may be pivotable about a first pivot axis that is oriented transverse to the longitudinal axis of the proximal hub. The end effector may further include a jaw assembly. The jaw assembly may include at least one support plate pivotally connected to the distal hub of the wrist assembly. The at least one support plate may be pivotable about a second pivot axis that is oriented transverse to the longitudinal axis of the distal hub of the wrist assembly. A pair of jaws may be pivotally supported on the at least one support plate. Each jaw may include a pivot point connected to the at least one support plate. A proximal portion of each jaw may extend proximally of the pivot point and a distal portion may extend distally of the pivot point. The jaw assembly may further include a cam pulley rotatably supported on the at least one support plate. The cam pulley may be operatively connected to the proximal end of each of the jaws such that rotation of the cam pulley may result in an opening or closing of the jaw assembly.

The cam pulley may be pivotally supported, on the at least one support plate, at the second pivot axis. The cam pulley may define at least one arcuate slot formed in a surface thereof. Each arcuate slot may include a first end spaced a first radial distance from a pivot axis of the cam pulley; and a second end spaced a second radial distance from the pivot axis of the cam pulley. The proximal portion of each jaw may be in sliding and camming connection with a respective arcuate slot of the cam pulley.

The pair of jaws of the jaw assembly may share a common pivot point.

The pivot point of each of the pair of jaws may be spaced a lateral distance from the second pivot axis.

At least one cable may be connected to the cam pulley at a location off-set a radial distance from the second pivot axis. At least one cable may be connected to the at least one support plate at a location off-set a radial distance from the second pivot axis. At least one cable may be connected to the distal hub of the wrist assembly at a location off-set a radial distance from the first pivot axis.

In an aspect of the present disclosure, at least one cable may be connected to the cam pulley at a location off-set a radial distance from the second pivot axis. At least one cable may be connected to the at least one support plate at a location off-set a radial distance from the second pivot axis. At least one cable may be connected to the distal hub of the wrist assembly at a location off-set a radial distance from the first pivot axis.

In another aspect of the present disclosure, at least one cable may be connected to the cam pulley at a location off-set a radial distance from the second pivot axis. At least one cable may be connected to the at least one support plate at a location off-set a radial distance from the second pivot axis. At least one cable may be connected to the distal hub of the wrist assembly at a location off-set a radial distance from the first pivot axis.

The cam pulley may define a single arcuate slot formed therein. The proximal end of each jaw may define an angled slot formed therein, wherein the angled slots may diverge from one another in a proximal direction. The jaw assembly may include a cam pin slidably disposed within the arcuate slot of the cam pulley and the angled slot of each jaw.

The at least one support plate may define an axially extending slot formed therein, and wherein the cam pin may be slidably disposed within the axially extending slot formed in the at least one support plate.

At least one cable may be connected to the cam pulley at a location off-set a radial distance from the second pivot axis. At least one cable may be connected to the at least one support plate at a location off-set a radial distance from the second pivot axis. At least one cable may be connected to the distal hub of the wrist assembly at a location off-set a radial distance from the first pivot axis.

The cam pulley of the jaw assembly may include at least one cam plate, and wherein the jaw assembly further includes a cam link pivotally connected to a respective one cam plate and a respective one support plate.

The respective one support plate may define a longitudinally extending slot formed therein. The cam link may include a first end pivotally connected to the respective one cam plate, and a second end pivotably and slidably connected to the longitudinally extending slot formed in the respective one support plate.

The proximal end of each jaw may define an angled slot formed therein, wherein the angled slots diverge from one another in a proximal direction. The jaw assembly may include a cam pin slidably disposed within the axial slot of each support plate and the angled slot of each jaw.

At least one cable may be connected to the at least one cam plate at a location off-set a radial distance from the second pivot axis. At least one cable may be connected to the at least one support plate at a location off-set a radial distance from the second pivot axis. At least one cable may be connected to the distal hub of the wrist assembly at a location off-set a radial distance from the first pivot axis.

The cam pulley of the jaw assembly may include at least one cam plate. The jaw assembly may further include at least one cam linkage pivotally connected to a respective one cam plate and a respective proximal portion of a respective jaw of the jaw assembly.

The cam pulley may include a pivot pin disposed along the second pivot axis. The pivot pin may non-rotatably support the cam plate. The at least one cam linkage may include a first cam linkage having a proximal link non-rotatably extending from the pivot pin of the cam pulley, and a distal link pivotably interconnecting the proximal link of the first cam linkage and the proximal portion of a first jaw of the jaw assembly. A second cam linkage may have a proximal link non-rotatably extending from the pivot pin of the cam pulley, and a distal link pivotably interconnecting the proximal link of the second cam linkage and the proximal portion of a second jaw of the jaw assembly. The proximal link of the second cam linkage may be radially offset from the proximal link of the first cam linkage.

At least one cable may be connected to the cam plate at a location off-set a radial distance from the second pivot axis. At least one cable may be connected to the at least one support plate at a location off-set a radial distance from the second pivot axis. At least one cable may be connected to the distal hub of the wrist assembly at a location off-set a radial distance from the first pivot axis.

According to another aspect of the present disclosure, a method of actuating an end effector of a robotic surgical system is provided. The method includes providing a surgical tool including an end effector. The end effector includes a pair of jaws pivotable about a first axis; a first and a second cam pulley rotatable about a second axis parallel to the first axis and coupled to the pair of jaws; and a cam follower coupling the first and the second pulleys to each of the pair of jaws. The method further includes rotating the first cam pulley to open or close the pair of jaws about the first axis; and applying a force to the second cam pulley to rotate the pair of jaws about the second axis.

The first cam pulley may multiply a closure force of the pair of jaws during the rotation thereof.

The pair of jaws may be pivoted about a common first axis.

Each jaw of the pair of jaws may be pivoted about a respective first axis, wherein each first axis may be offset from one another.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIG. 28 is a rear, perspective view of the end effector of FIG. 23 illustrating the jaw assembly thereof in a closed and non-articulated condition, and illustrating the wrist assembly thereof in a non-articulated condition;

FIG. 29 is a cross-sectional view of the end effector of FIG. 28, as taken through section line 29-29 of FIG. 28;

FIG. 31 is a cross-sectional view of the end effector of FIG. 23, as taken through section line 31-31 of FIG. 29, illustrating the jaw assembly in the closed condition;

FIG. 32 is an enlarged view of the indicated area of detail of FIG. 31;

FIG. 33 is a cross-sectional view of the end effector of FIG. 23, as taken through section line 31-31 of FIG. 29, illustrating the jaw assembly in the open condition;

FIG. 34 is an enlarged view of the indicated area of detail of FIG. 33;

FIG. 44 is a rear, perspective view of the end effector of FIG. 39 illustrating the jaw assembly thereof in a closed and non-articulated condition, and illustrating the wrist assembly thereof in a non-articulated condition;

FIG. 45 is a cross-sectional view of the end effector of FIG. 44, as taken through section line 45-45 of FIG. 44;

FIG. 49 is a rear, perspective view of the jaw assembly of the end effector of FIG. 39, illustrating the jaw assembly in the open condition;

FIG. 50 is a side elevational view of the jaw assembly of FIG. 49;

DETAILED DESCRIPTION

Figure 1A:
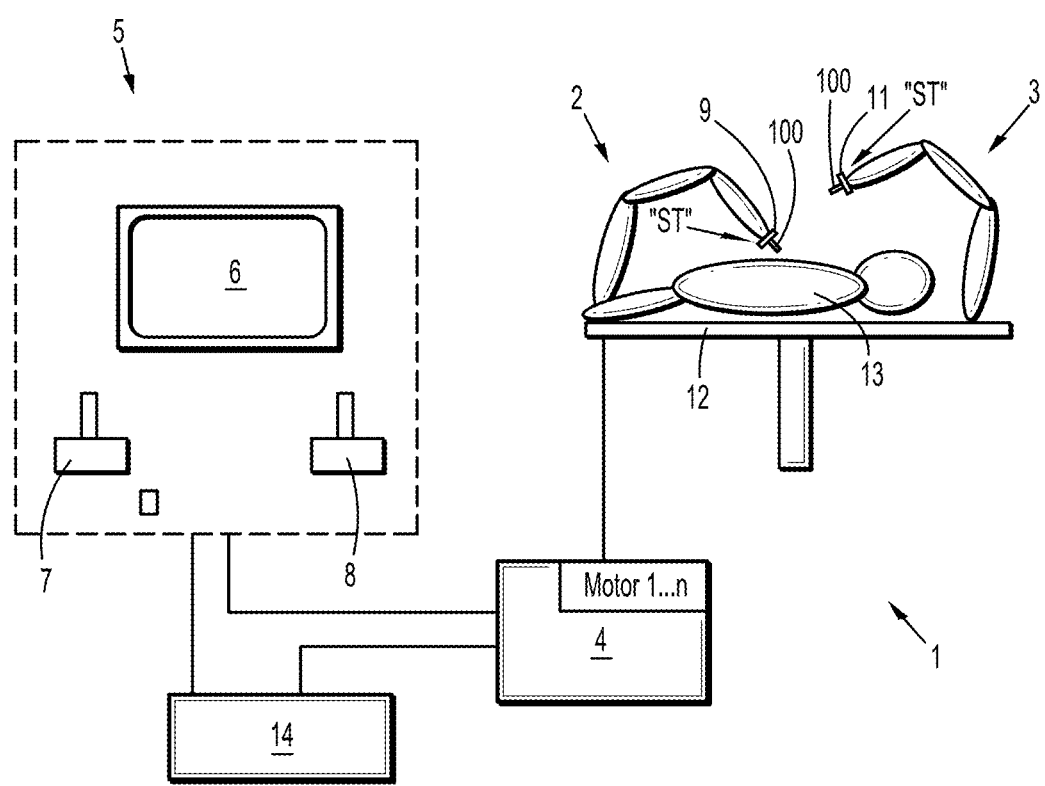
FIG. 1A is a schematic illustration of a medical work station and operating console in accordance with the present disclosure.

Embodiments of the presently disclosed jaw assemblies and/or wrist assemblies are described in detail with reference to the drawings, in which like reference numerals designate identical or corresponding elements in each of the several views. As used herein the term "distal" refers to that portion of the jaw assembly and/or wrist assembly that is farther from the user, while the term "proximal" refers to that portion of the jaw assembly and/or wrist assembly that is closer to the user.

Figure 1B:
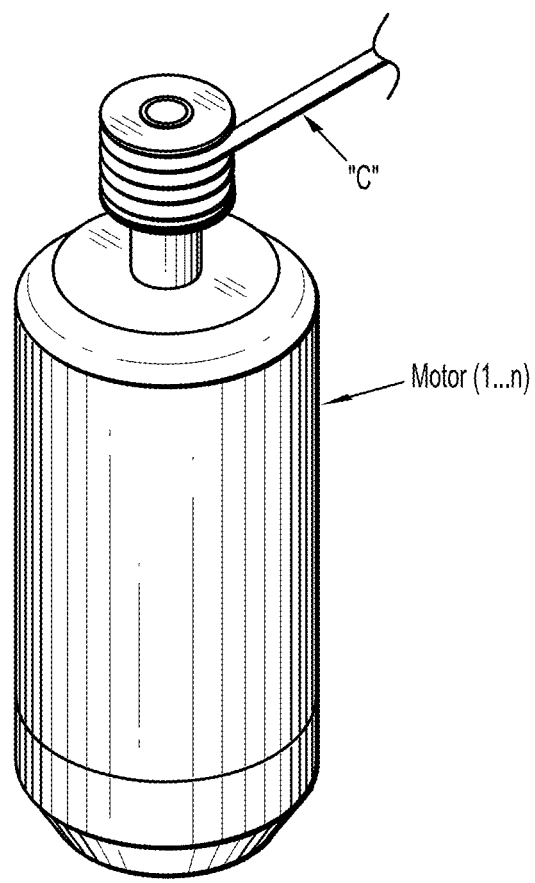
FIG. 1B is a schematic, perspective view of a motor of a control device of the medical work station of FIG. 1A.
Figure 2:
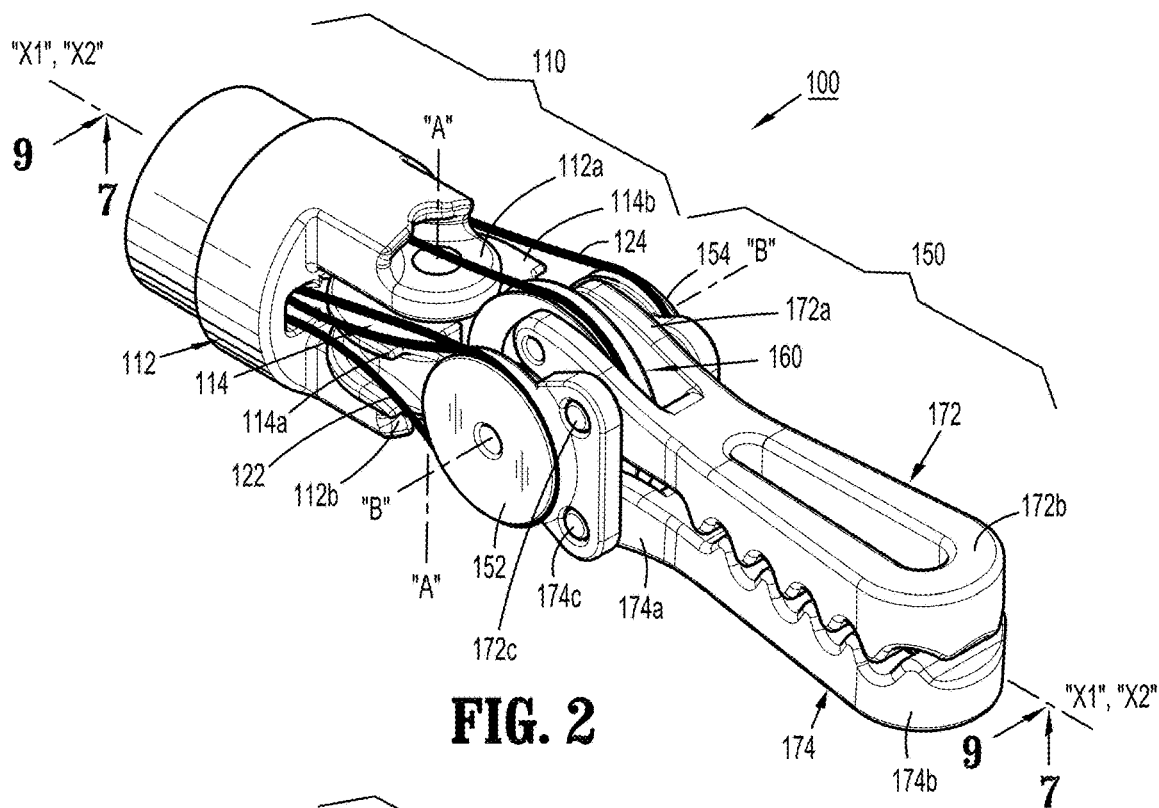
FIG. 2 is a perspective view of an end effector, according to an embodiment of the present disclosure, for use in the medical work station of FIG. 1A, illustrating a jaw assembly thereof in a closed condition.
Figure 3:
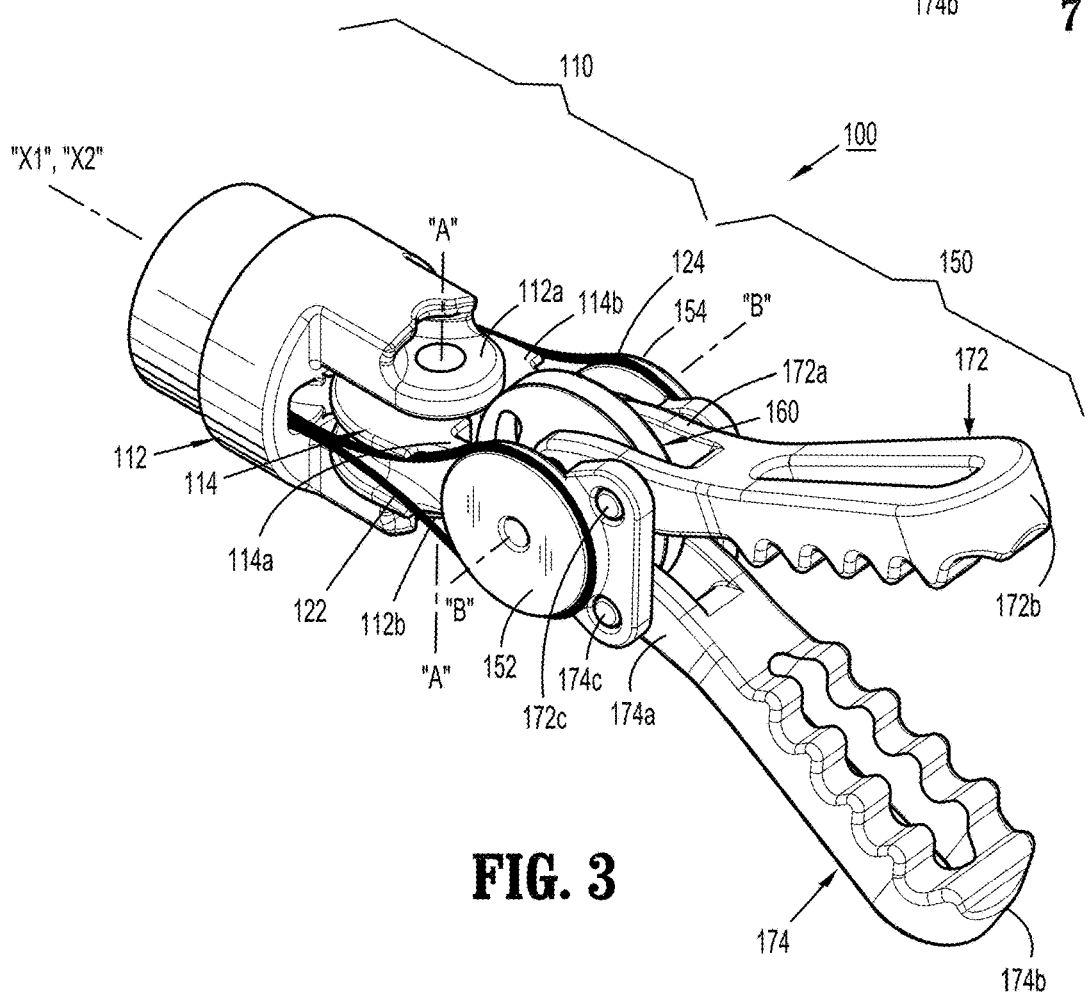
FIG. 3 is a perspective view of the end effector of FIG. 2 illustrating the jaw assembly thereof in an open condition.
Figure 4:
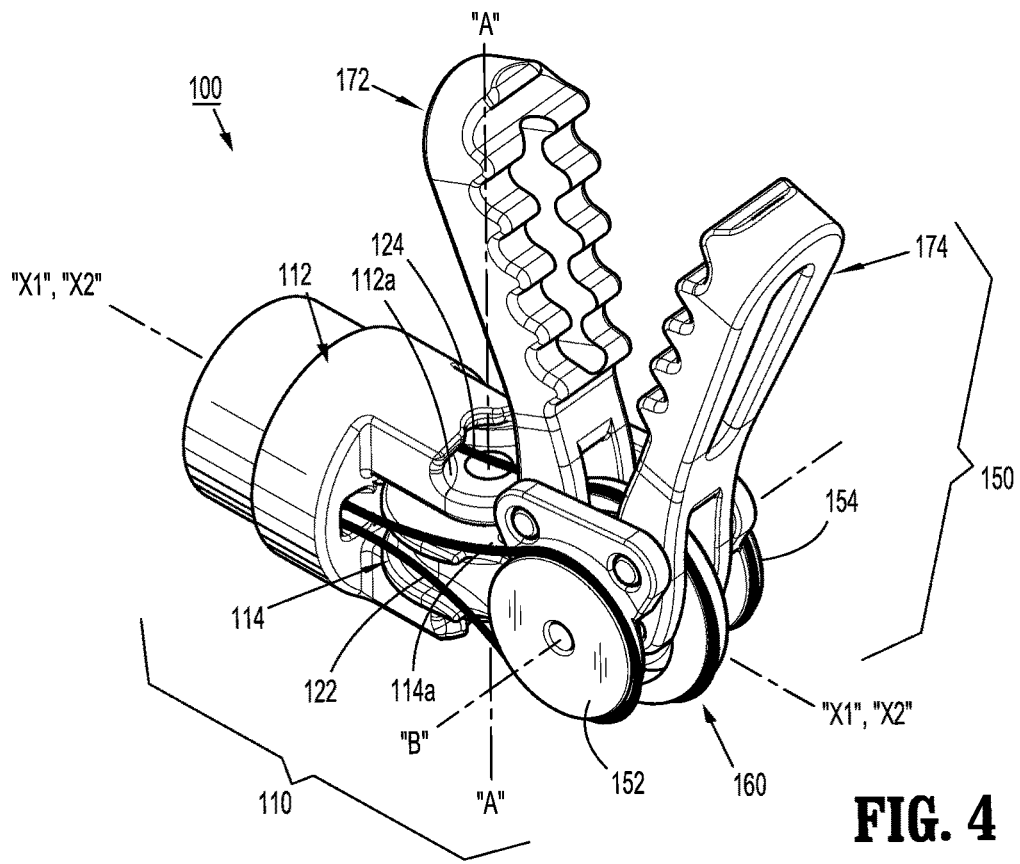
FIG. 4 is a perspective view of the end effector of FIG. 2 illustrating the jaw assembly thereof in an open and articulated condition.
Figure 5:
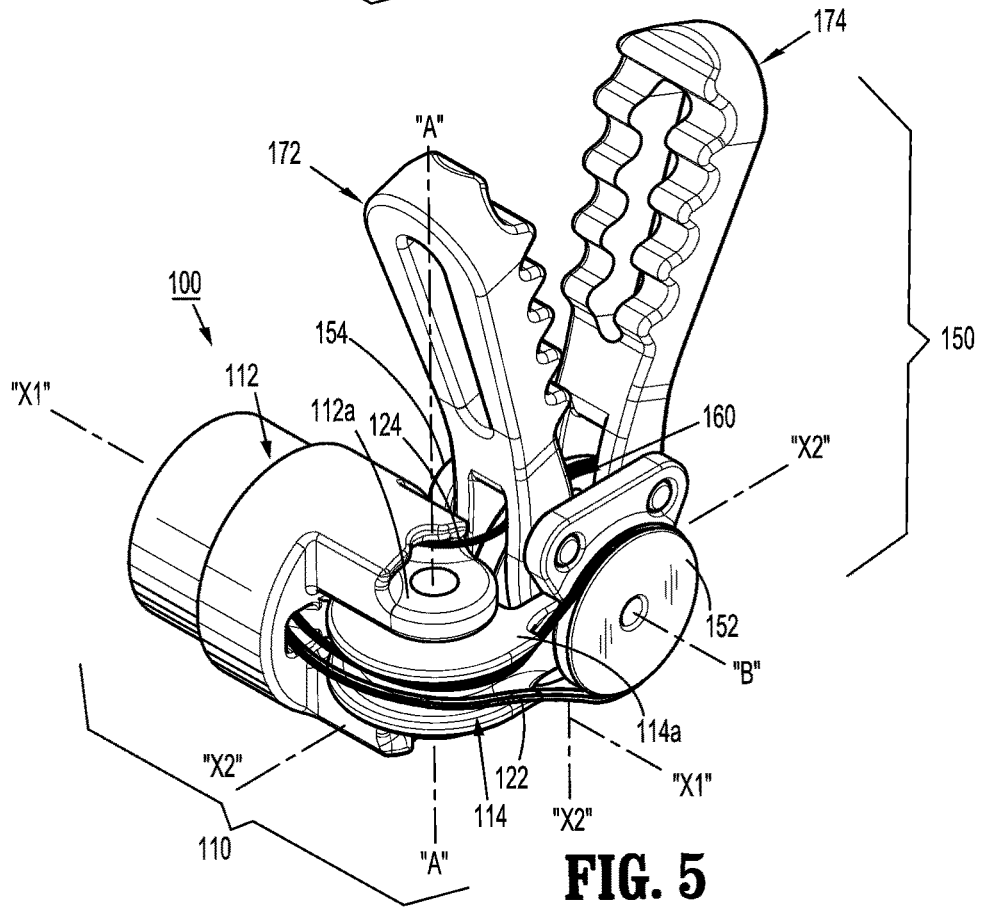
FIG. 5 is a perspective view of the end effector of FIG. 2 illustrating the jaw assembly thereof in an open and articulated condition, and illustrating a wrist assembly thereof in an articulated condition.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 includes a plurality of members, which are connected through joints, and an attaching device 9, 11, to which may be attached, for example, a surgical tool "ST" supporting an end effector 100, in accordance with any one of several embodiments disclosed herein, as will be described in greater detail below.

Robot arms 2, 3 may be driven by electric drives (not shown) that are connected to control device 4. Control device 4 (e.g., a computer) is set up to activate the drives, in particular by means of a computer program, in such a way that robot arms 2, 3, their attaching devices 9, 11 and thus the surgical tool (including end effector 100) execute a desired movement according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in a minimally invasive manner by means of end effector 100. Medical work station 1 may also include more than two robot arms 2, 3, the additional robot arms likewise being connected to control device 4 and being telemanipulatable by means of operating console 5. A medical instrument or surgical tool (including an end effector 100) may also be attached to the additional robot arm.

Reference may be made to U.S. Patent Publication No. 2012/0116416, filed on Nov. 3, 2011, entitled "Medical Workstation," the entire content of which is incorporated herein by reference, for a detailed discussion of the construction and operation of medical work station 1.

Control device 4 may control a plurality of motors (Motor 1 . . . n) with each motor configured to wind-up or let out a length of a cable "C" (FIG. 1B) extending through each robot arm to end effector 100 of the surgical tool. In use, as cables "C" are wound-up and let out, cables "C" effect operation and/or movement of each end effector 100 of the surgical tool. It is contemplated that control device 4 coordinates the activation of the various motors (Motor 1 . . . n) to coordinate a winding-up or letting out a length of a respective cable "C" in order to coordinate an operation and/or movement of a respective end effector. Although FIG. 1B shows a single cable "C" that is wound up or let out by a single motor, in some instances two or more cables or two ends of a single cable may be wound up or let out by a single motor. For example, in some instances, two cables or cable ends may be coupled in opposite directions to a single motor so that as the motor is activated in a first direction, one of the cables winds up while the other cable lets out. Other cable configurations may be used in different embodiments.

Turning now to FIGS. 2-14, an end effector for connection to robot arms 2, 3 and for manipulation by control device 4, is generally designated as 100. End effector 100 includes a wrist assembly 110, and a jaw assembly 150 pivotally connected to wrist assembly 110. Wrist assembly 110 includes a proximal hub 112, in the form of a distally extending clevis, defining a first longitudinal axis "X1-X1." Proximal hub 112 defines a first pivot axis "A-A" that is oriented orthogonal to the first longitudinal axis "X1-X1." In an embodiment, first pivot axis "A-A" may extend through the first longitudinal axis "X1-X1." Proximal hub 112, being in the form of a clevis, includes a pair of spaced apart, opposed upright supports 112a, 112b through which first pivot axis "A-A" extends.

Wrist assembly 110 further includes a distal hub 114 pivotally connected to upright supports 112a, 112b of proximal hub 112. Distal hub 114 may be in the form of a distally extending clevis and defines a second longitudinal axis "X2-X2." Distal hub 114 defines a second pivot axis "B-B" that is oriented orthogonal to the first pivot axis "A-A" and orthogonal to the first longitudinal axis "X1-X1." In an embodiment, when the first longitudinal axis "X1-X1" is parallel with the second longitudinal axis "X2-X2" (i.e., end effector 100 is in an axially aligned orientation), second pivot axis "B-B" may extend through first longitudinal axis "X1-X1." Distal hub 114, being in the form of a clevis, includes a pair of spaced apart, opposed upright supports 114a, 114b through which second pivot axis "B-B" extends.

Turning now back to FIGS. 2-14, end effector 100 includes a jaw assembly 150 having a pair of spaced apart support or cam plates, or cam pulleys 152, 154 pivotally connected to respective upright supports 114a, 114b of distal hub 114 of wrist assembly 110, so as to be pivotable about second pivot axis "B-B."

With reference to FIGS. 2-8, 13 and 14, a single first cable 122 is at least partially wrapped around cam plate 152 and secured to at least one point thereof, or that the single first cable 122 may be wrapped at least once around cam plate 152, in the manner of a capstan. Single first cable 122 may include proximal ends that extend through robot arm 2 or 3 and operatively associated with a respective first motor and second motor (not shown) of control device 4. While a single first cable 122 is shown and described, it is contemplated that a first pair of cables (not shown) including respective distal ends may be secured to opposed sides of cam plate 152, or wrapped at least 180° around cam plate 152 and secured thereto, and including respective proximal ends extending through robot arm 2 or 3 and operatively associated with a respective first motor and second motor (not shown) of control device 4.

A single second cable 124 is at least partially wrapped around cam plate 154 and secured to at least one point thereof, or that the single second cable 124 may be wrapped at least once around cam plate 154, in the manner of a capstan. Single second cable 124 may include proximal ends that extend through robot arm 2 or 3 and operatively associated with a respective first motor and second motor (not shown) of control device 4. While a single second cable 124 is shown and described, it is contemplated that a first pair of cables (not shown) including respective distal ends may be secured to opposed sides of cam plate 154, or wrapped at least 180° around cam plate 154 and secured thereto, and including respective proximal ends extending through robot arm 2 or 3 and operatively associated with a respective first motor and second motor (not shown) of control device 4.

Jaw assembly 150 further includes a cam pulley 160 also pivotally connected to upright supports 114a, 114b of distal hub 114 of wrist assembly 110, specifically, between upright supports 114a, 114b, so as to also be pivotable about second pivot axis "B-B." Cam pulley 160 is substantially disc-shaped and defines a pair of opposed arcuate cam slots 162, 164 formed therein. Each cam slot 162, 164 includes a respective first end 162a, 164a spaced a first radial distance away from second pivot axis "B-B," and a respective second end 162b, 164b spaced a second radial distance away from second pivot axis "B-B," wherein the second radial distance is greater than the first radial distance. A shape or configuration of each cam slot 162, 164 may be modified or selected so as to vary or alter a closing/opening characteristic of jaw assembly 150, such as for example, to increase a clamping force (i.e., act as a force multiplier) of the jaw assembly 150 as the jaw assembly 150 is brought to a fully closed condition.

Jaw assembly 150 also includes a pair of jaws 172, 174 separately and independently pivotally connected to support plates 152, 154. Specifically, each jaw 172, 174 includes a pivot point 172c, 174c about which each jaw 172, 174 pivots. Pivot points 172c, 174c are spaced apart from one another, and spaced an orthogonal distance from first longitudinal axis "X1-X1," when end effector 100 is in an axially aligned orientation (i.e., when the first longitudinal axis "X1-X1" is parallel with the second longitudinal axis "X2-X2"). Each pivot point 172c, 174c defines a pivot axis that is parallel to second pivot axis "B-B" of distal hub 114.

Each jaw 172, 174 includes a respective proximal end 172a, 174a, and a respective distal end 172b, 174b. Each proximal end 172a, 174a extends proximally of respective pivot point 172c, 174c, and each distal end 172b, 174b extends distally of respective pivot point 172c, 174c.

Figure 6:
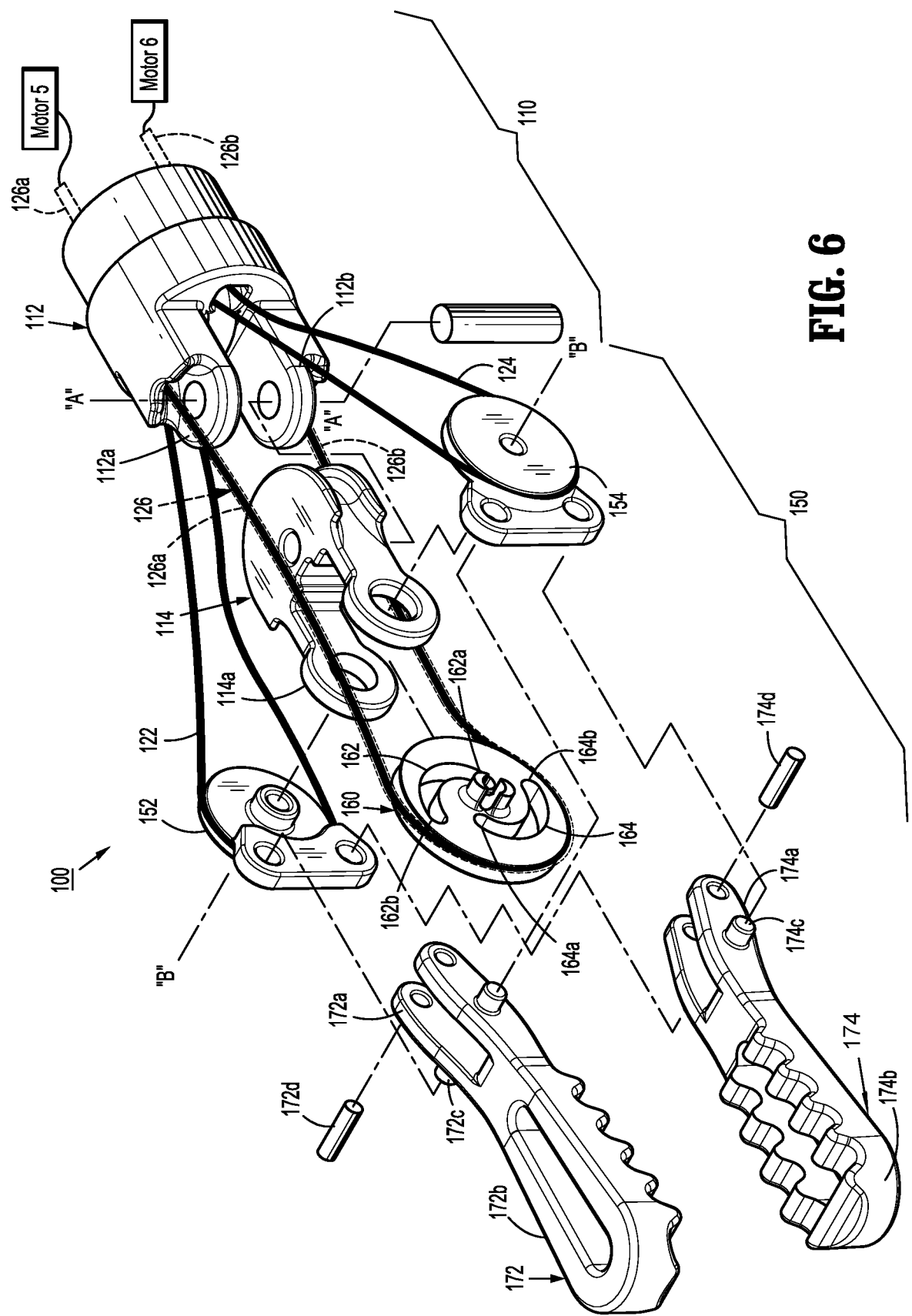
FIG. 6 is a perspective view, with parts separated, of the end effector of FIG. 2.
Figure 10:
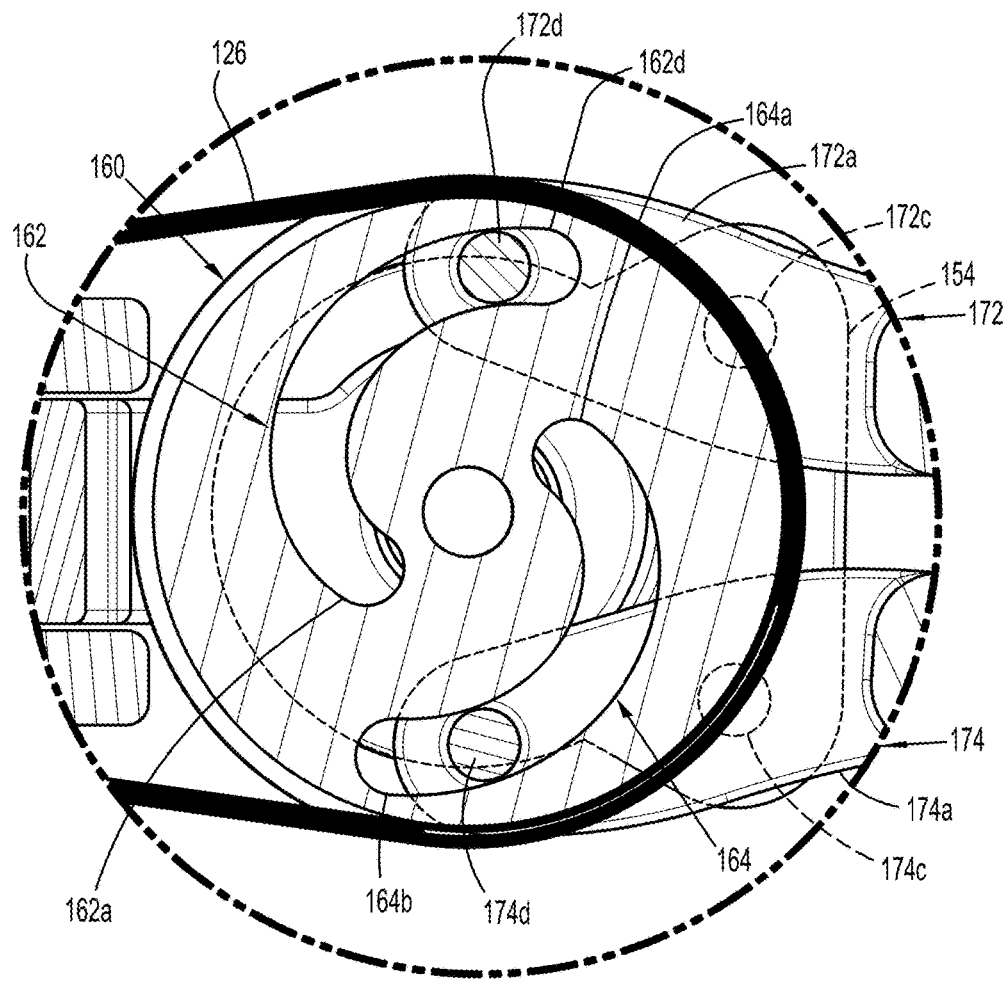
FIG. 10 is an enlarged view of the indicated area of detail of FIG. 9.
Figure 11:
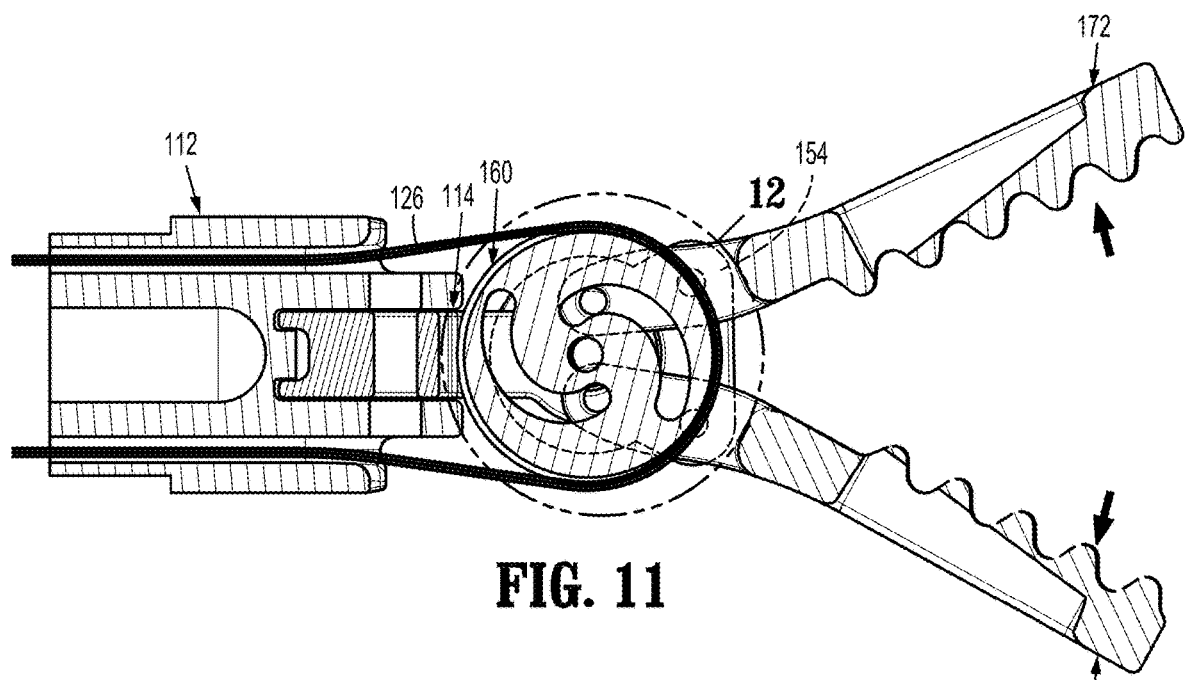
FIG. 11 is a cross-sectional view of the end effector of FIG. 2, as taken through section line 9-9 of FIG. 2, illustrating the jaw assembly in the open condition.
Figure 12:
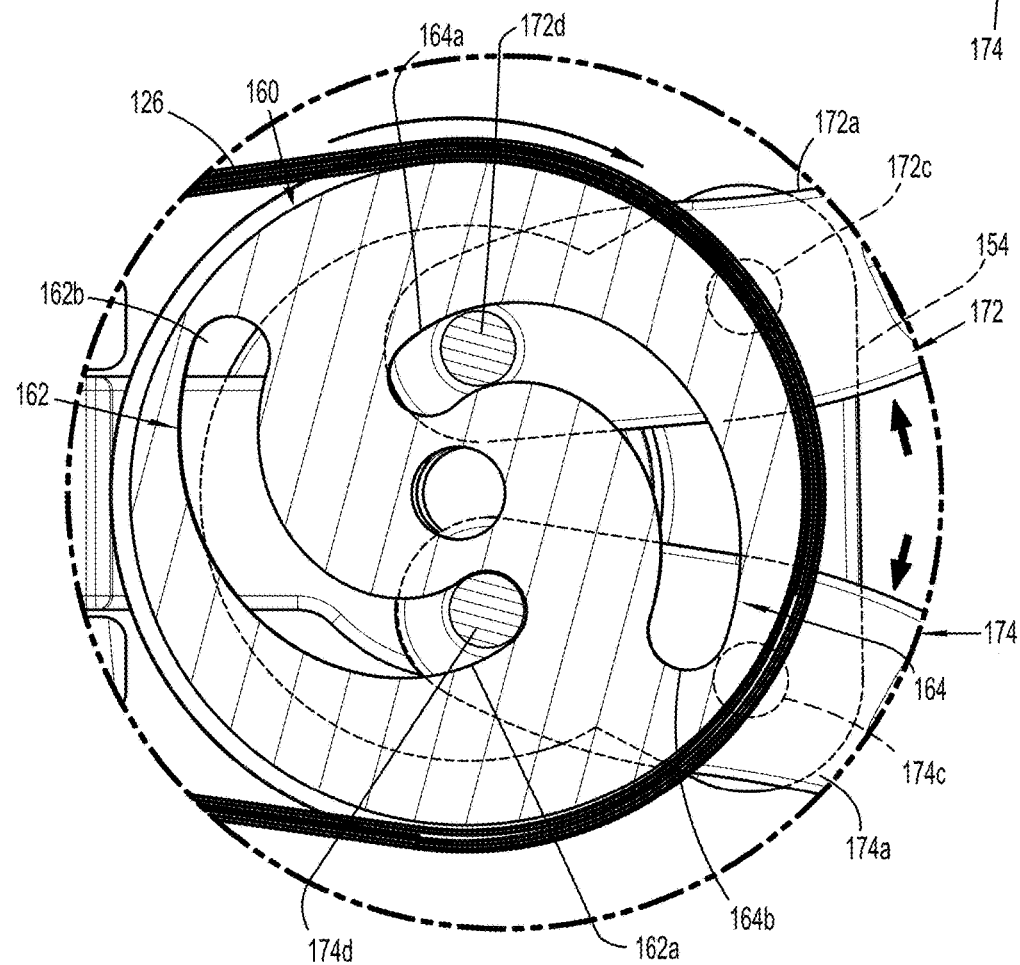
FIG. 12 is an enlarged view of the indicated area of detail of FIG. 11.

As shown in FIGS. 6, 10 and 12, a pin or the like 172d, 174d respectively pivotally and slidably connects each proximal end 172a, 174a of respective jaw 172, 174 to a respective cam slot 162, 164 formed in cam pulley 160. In use, as will be described in greater detail below, as cam pulley 160 is rotated in either a clockwise or counter clockwise direction, jaws 172, 174 will be caused to be opened or closed accordingly.

Each distal end 172b, 174b of jaws 172, 174 defines a grip or toothed portion in juxtaposed relation to one another.

With reference to FIG. 6, a single third cable 126 is at least partially wrapped around cam pulley 160 and secured to at least one point thereof, or that the single third cable 126 may be wrapped at least once around cam pulley 160, in the manner of a capstan. Single third cable 126 may include proximal ends 126a, 126b that extend through robot arm 2 or 3 and operatively associated with a respective fifth motor (Motor 5) and sixth motor (Motor 6) of control device 4. While a single third cable 126 is shown and described, it is contemplated that a third pair of cables (not shown) including respective distal ends may be secured to opposed sides of cam pulley 160, or wrapped at least 180° around cam pulley 160 and secured thereto, and including respective proximal ends extending through robot arm 2 or 3 and operatively associated with a respective fifth motor (Motor 5) and sixth motor (Motor 6) of control device 4.

Figure 7:
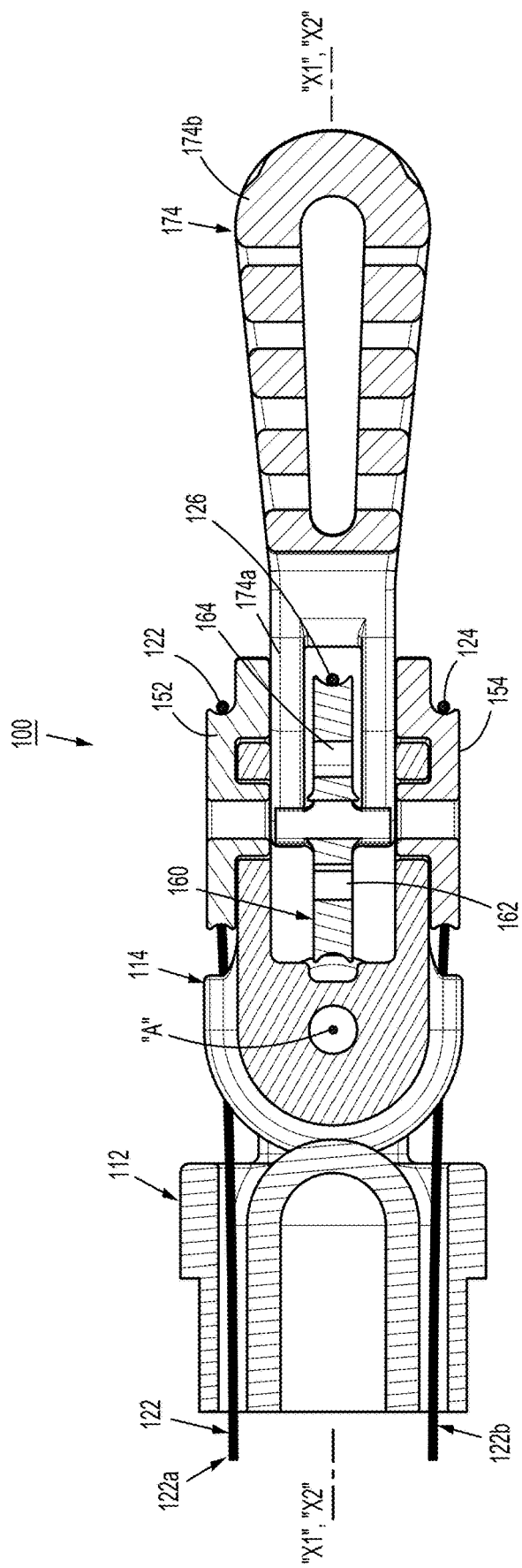
FIG. 7 is a cross-sectional view of the end effector of FIG. 2, as taken through section line 7-7 of FIG. 2.
Figure 8:
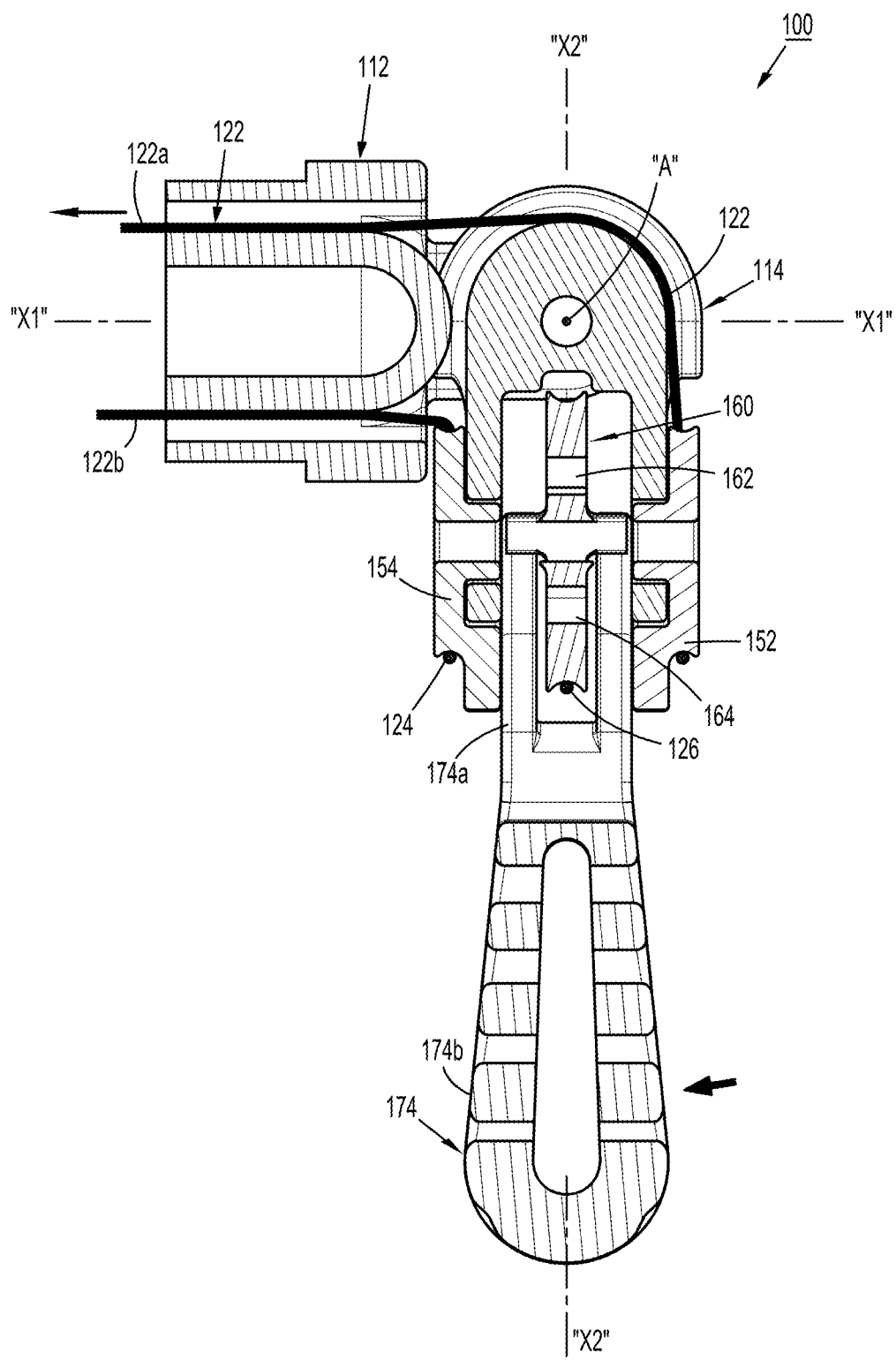
FIG. 8 is a cross-sectional view of the end effector of FIG. 2, as taken through section line 7-7 of FIG. 2, illustrating the jaw assembly in an articulated condition.
Figure 9:
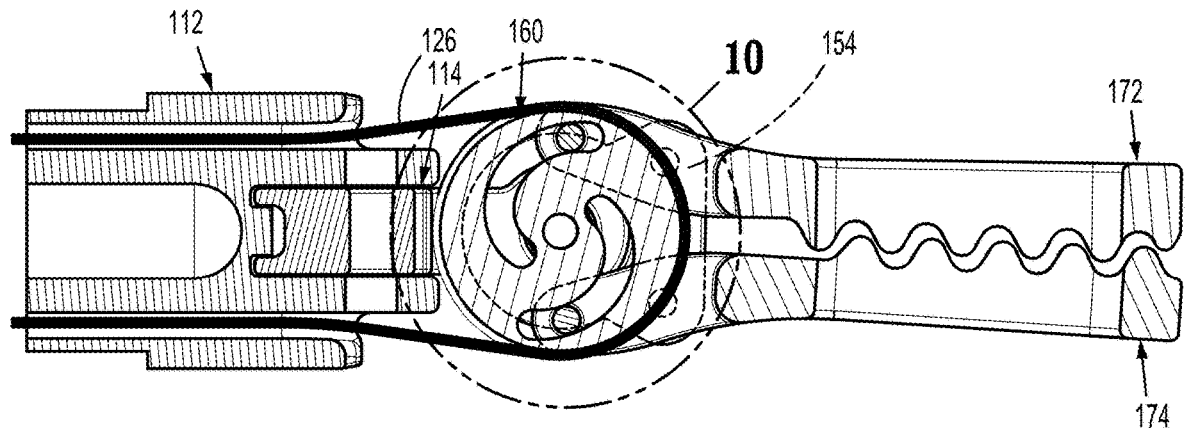
FIG. 9 is a cross-sectional view of the end effector of FIG. 2, as taken through section line 9-9 of FIG. 2, illustrating the jaw assembly in the closed condition.

In operation, as illustrated in FIGS. 7 and 8, in order to pivot end effector 100 about first pivot axis "A-A" of wrist assembly 110, it is contemplated that the proximal ends of first cable 122 are drawn in a proximal direction as a result of an input from control device 4 to activate a first motor (not shown), and optionally activate a second motor (not shown) to let out the proximal ends of second cable 124, or vice versa. Depending on which proximal ends of first cable 122 or second cable 124 are drawn in a proximal direction will determine which direction of pivot, about first pivot axis "A-A," is achieved.

Figure 13:
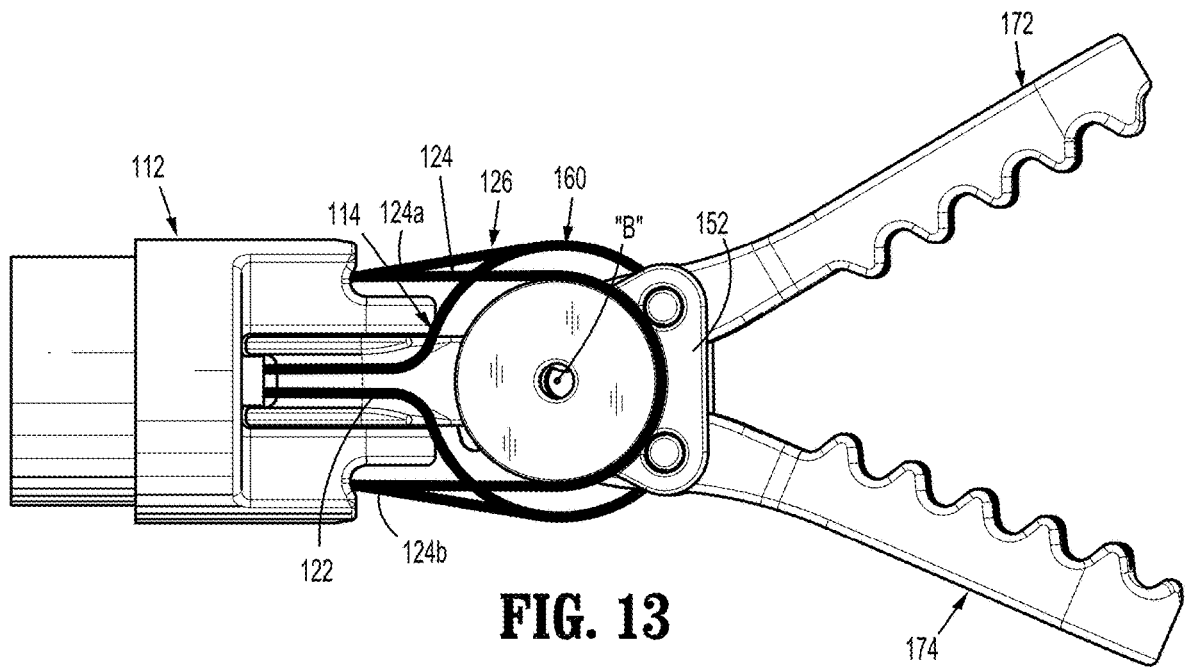
FIG. 13 is a plan view of the end effector of FIG. 2, illustrating the jaw assembly in a non-articulated and open condition.
Figure 14:
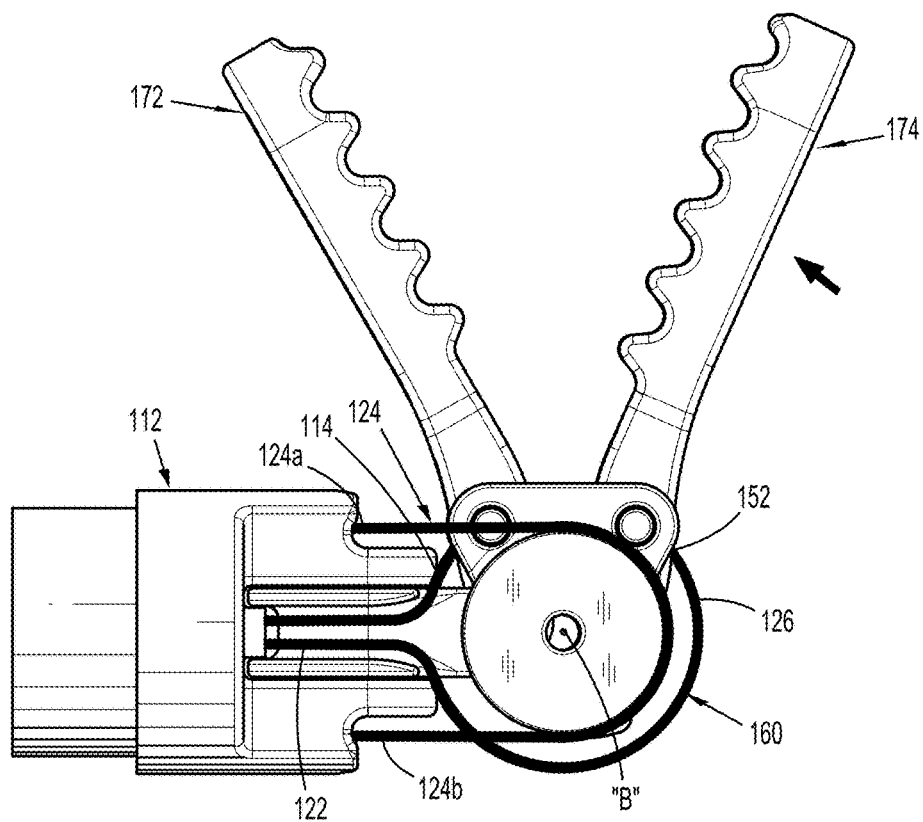
FIG. 14 is a plan view of the end effector of FIG. 2, illustrating the jaw assembly in an articulated and open condition.
Figure 17:
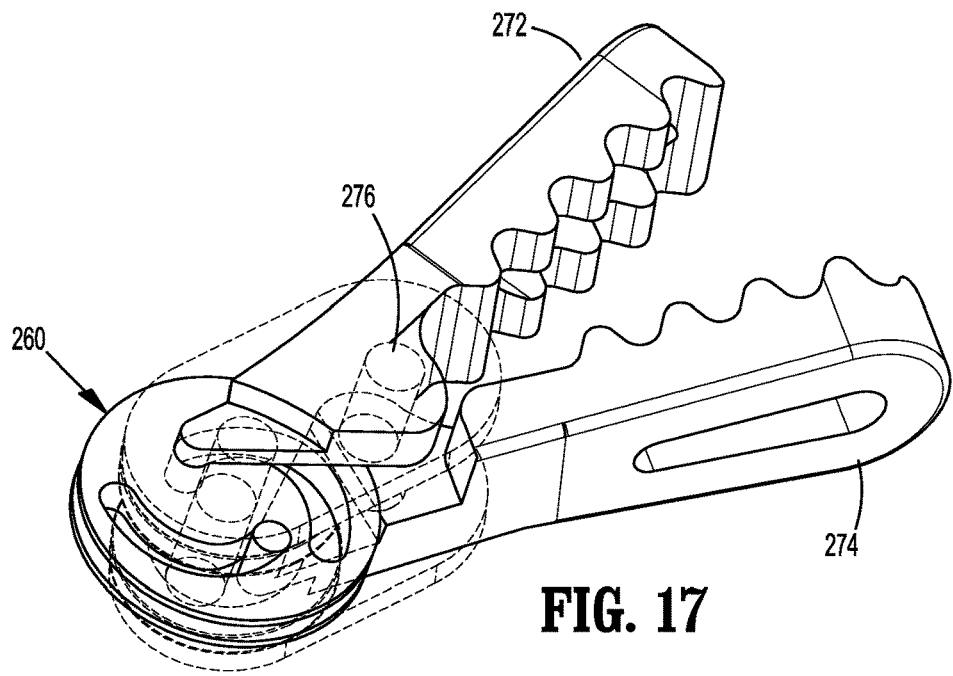
FIG. 17 is a perspective illustration of the jaw assembly of the end effector of FIG. 15.
Figure 15:
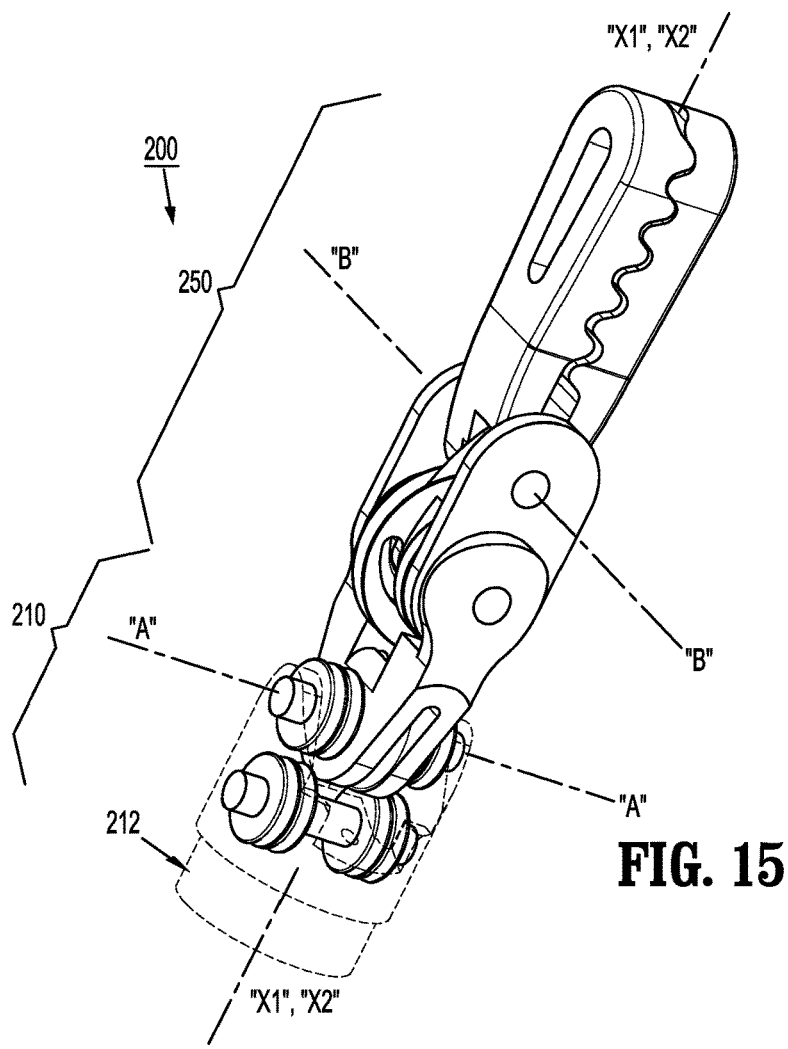
FIG. 15 is a perspective illustration of an end effector, according to another embodiment of the present disclosure, for use in the medical work station of FIG. 1A, illustrating a jaw assembly thereof in a closed condition.
Figure 16:
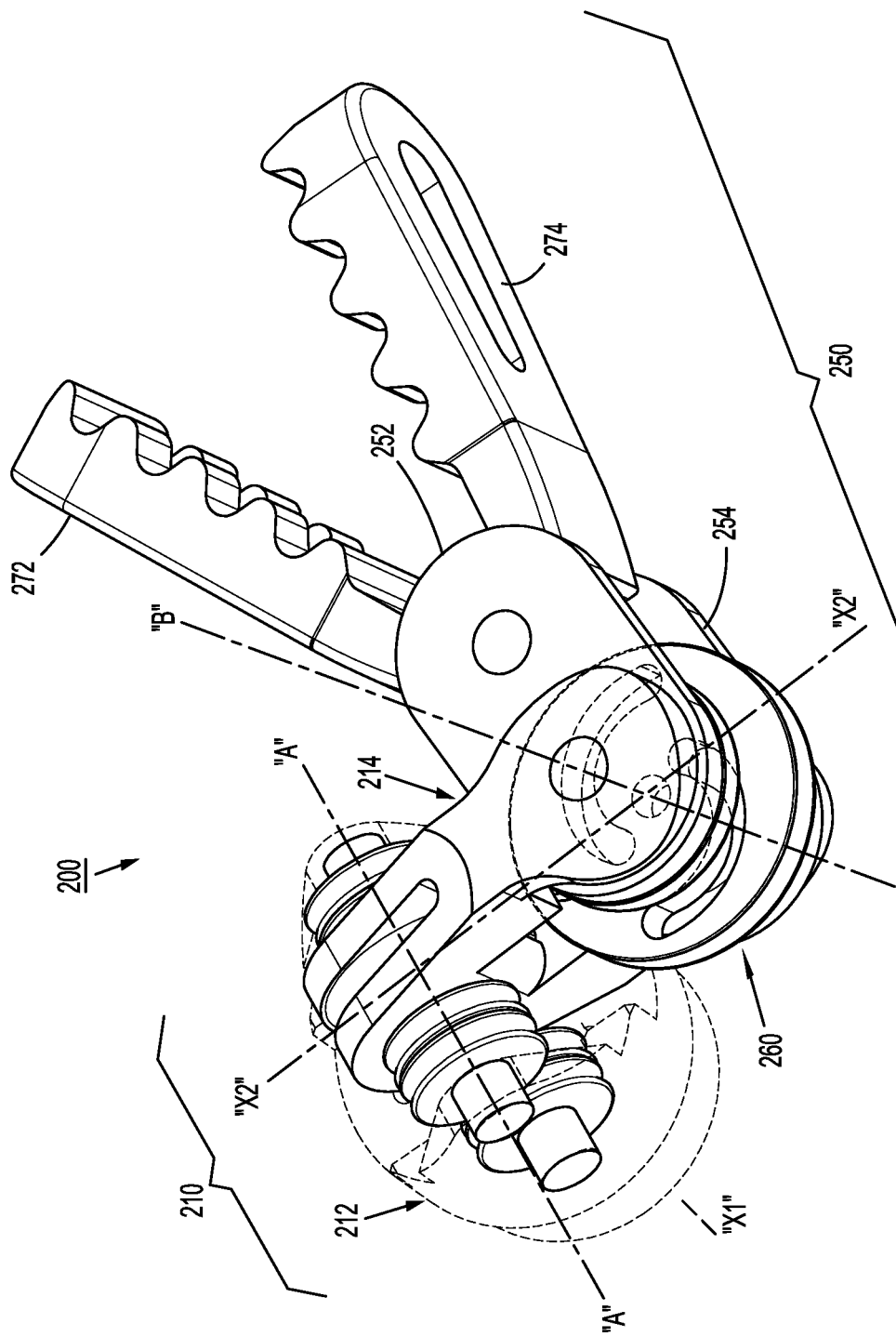
FIG. 16 is a perspective illustration of the end effector of FIG. 15 illustrating the jaw assembly thereof in an open and articulated condition, and illustrating a wrist assembly thereof in an articulated condition.

Additionally, in operation, as illustrated in FIGS. 13 and 14, in order to pivot jaws 172, 174 of end effector 100 about second pivot axis "B-B" of jaw assembly 150, it is contemplated that one of the proximal ends of first cable 122 and a corresponding one of the proximal ends of second cable 124 are drawn in a proximal direction as a result of an input from control device 4 to activate a third motor (not shown), and optionally activate a fourth motor (not shown) to let out the other of the proximal ends of first cable 122 and a corresponding other of the proximal ends of second cable 124, or vice versa. Depending on which one of the proximal ends of first cable 122 and second cable 124 are drawn in a proximal direction will determine which direction of pivot, about second pivot axis "B-B," is transmitted to support plates 152 and 154 to thus pivot jaws 172, 174.

Also in operation, in order to open or close jaws 172, 174 of end effector 100, about respective pivot points 172c, 174c of jaws 172, 174, it is contemplated that one proximal end 126a or 126b of third cable 126 (FIG. 6) is drawn in a proximal direction as a result of an input from control device 4 to activate a fifth motor (Motor 5), and optionally activate a sixth motor (Motor 6) to let out the other proximal end 126a or 126b of third cable 126. Depending on which one of the proximal ends 126a, 126b of third cable 126 is drawn in a proximal direction will determine which direction cam pulley 160 is rotated (about pivot/rotation axis "B-B") and thus whether jaws 172, 174 are opened or closed. Specifically, as cam pulley 160 is rotated in a first direction, the pins connecting jaws 172, 174 to cam pulley 160 are slid or cammed through respective cam slots 162, 164 and drawn radially inward to thereby open jaws 172, 174. Likewise, as cam pulley 160 is rotated in a second direction, the pins connecting jaws 172, 174 to cam pulley 160 are slid or cammed through respective cam slots 162, 164 and pushed radially outward to thereby close jaws 172, 174.

Turning now to FIGS. 15-22, an end effector for connection to robot arms 2, 3 and for manipulation by control device 4, in accordance with another embodiment of the present disclosure, is generally designated as 200. End effector 200 is substantially similar to end effector 100 and thus will only be described in detail herein to the extent necessary to describe differences in construction and/or operation from those of end effector 100.

End effector 200 includes a wrist assembly 210, and a jaw assembly 250 pivotally connected to wrist assembly 210. Wrist assembly 210 includes a proximal hub 212 defining a first longitudinal axis "X1-X1," and a first pivot axis "A-A" that is oriented orthogonal to the first longitudinal axis "X1-X1." Wrist assembly 210 further includes a distal hub 214 pivotally connected to proximal hub 212. Distal hub 214 defines a second longitudinal axis "X2-X2," and a second pivot axis "B-B" that is oriented orthogonal to the first pivot axis "A" and orthogonal to the first longitudinal axis "X1-X1." In an embodiment, when the first longitudinal axis "X1-X1" is parallel with the second longitudinal axis "X2-X2" (i.e., end effector 200 is in an axially aligned orientation), second pivot axis "B-B" may extend through first longitudinal axis "X1-X1."

A single first cable (not shown) may be at least partially wrapped around distal hub 214 and secured to at least one point thereof, or that the single first cable may be wrapped at least once around distal hub 214, in the manner of a capstan. The single first cable may include proximal ends that extend through robot arm 2 or 3 and operatively associated with a respective first motor and second motor (not shown) of control device 4. While a single first cable is described, it is contemplated that a first pair of cables (not shown) including respective distal ends may be secured to opposed sides of distal hub 214, or wrapped at least 180° around distal hub 214 and secured thereto, and including respective proximal ends extending through robot arm 2 or 3 and operatively associated with a respective first motor and second motor (not shown) of control device 4.

With continued reference to FIGS. 17-22, end effector 200 includes a jaw assembly 250 having a pair of spaced apart support or cam plates, or cam pulleys 252, 254 pivotally connected to distal hub 214 of wrist assembly 210, so as to be pivotable about second pivot axis "B-B."

Jaw assembly 250 further includes a cam pulley 260 also pivotally connected to upright supports of distal hub 214 of wrist assembly 210 so as to also be pivotable about second pivot axis "B-B." Cam pulley 260 is substantially disc-shaped and defines a pair of opposed arcuate cam slots 262, 264 formed therein. Each cam slot 262, 264 includes a respective first end 262a, 264a spaced a first radial distance away from second pivot axis "B-B," and a respective second end 262b, 264b spaced a second radial distance away from second pivot axis "B-B," wherein the second radial distance is greater than the first radial distance. A shape or configuration of each cam slot 262, 264 may be modified or selected so as to vary or alter a closing/opening characteristic of jaw assembly 250, such as for example, to increase a clamping force (i.e., act as a force multiplier) of the jaw assembly 250 as the jaw assembly 250 is brought to a fully closed condition.

Jaw assembly 250 also includes a pair of jaws 272, 274 pivotally connected to support plates 252, 254 at a common pivot point 276 about which each jaw 272, 274 pivots. Pivot point 276 is spaced an axial distance distally of second pivot axis "B-B" when end effector 200 is in a axially aligned orientation (i.e., when the first longitudinal axis "X1-X1" is parallel with the second longitudinal axis "X2-X2"). Pivot point 276 defines a pivot axis that is parallel to second pivot axis "B-B" of distal hub 214.

Each jaw 272, 274 includes a respective proximal end 272a, 274a, and a respective distal end 272b, 274b. Each proximal end 272a, 274a extends proximally of pivot point 276, and each distal end 272b, 274b extends distally of pivot point 276.

Figure 21:
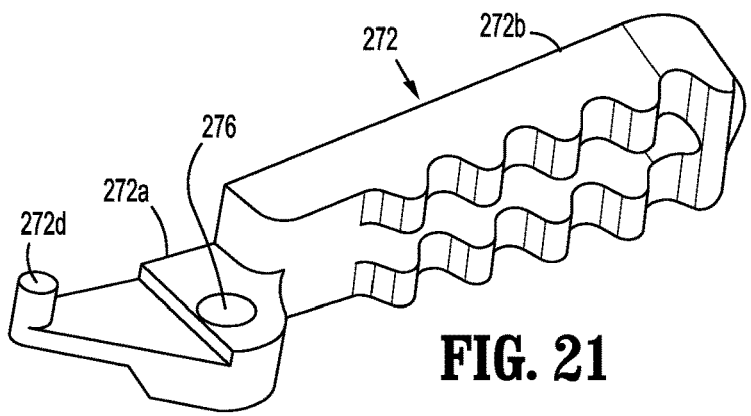
FIGS. 21 and 22 are perspective illustrations of a first jaw and a second jaw of the jaw assembly of the end effector of FIG. 15.
Figure 22:
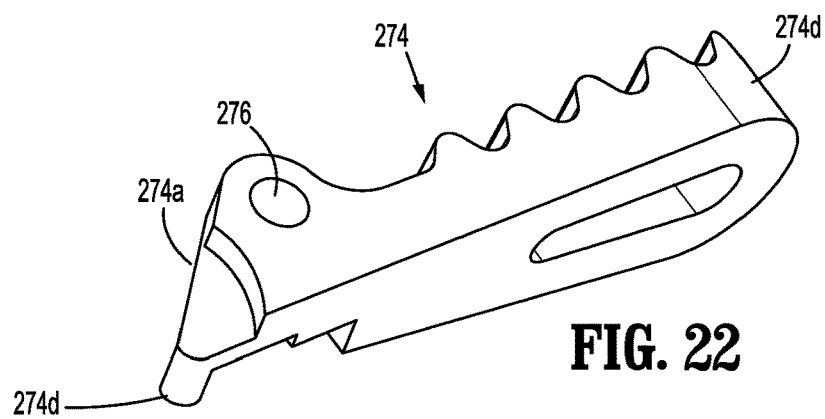
Figure 20:
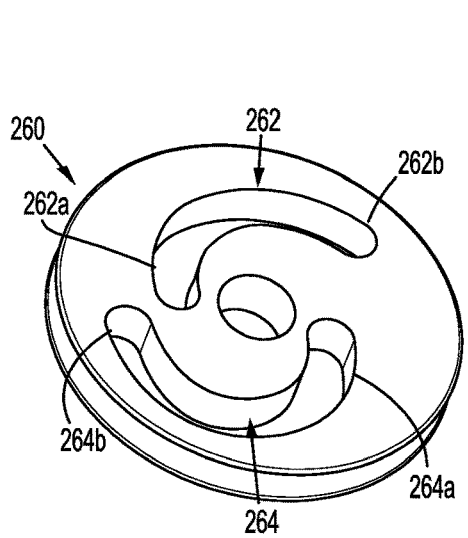
FIG. 20 is a perspective illustration of a cam pulley of the jaw assembly of the end effector of FIG. 15.
Figure 19:
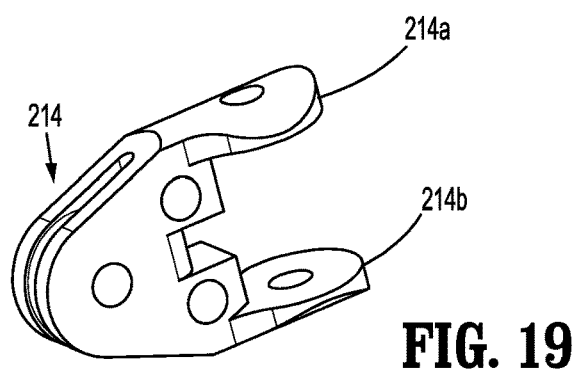
FIG. 19 is a perspective illustration of a distal hub of the wrist assembly of the end effector of FIG. 15.
Figure 18:
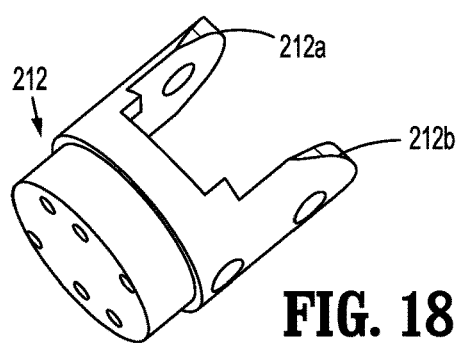
FIG. 18 is a perspective illustration of a proximal hub of a wrist assembly of the end effector of FIG. 15.
Figure 23:
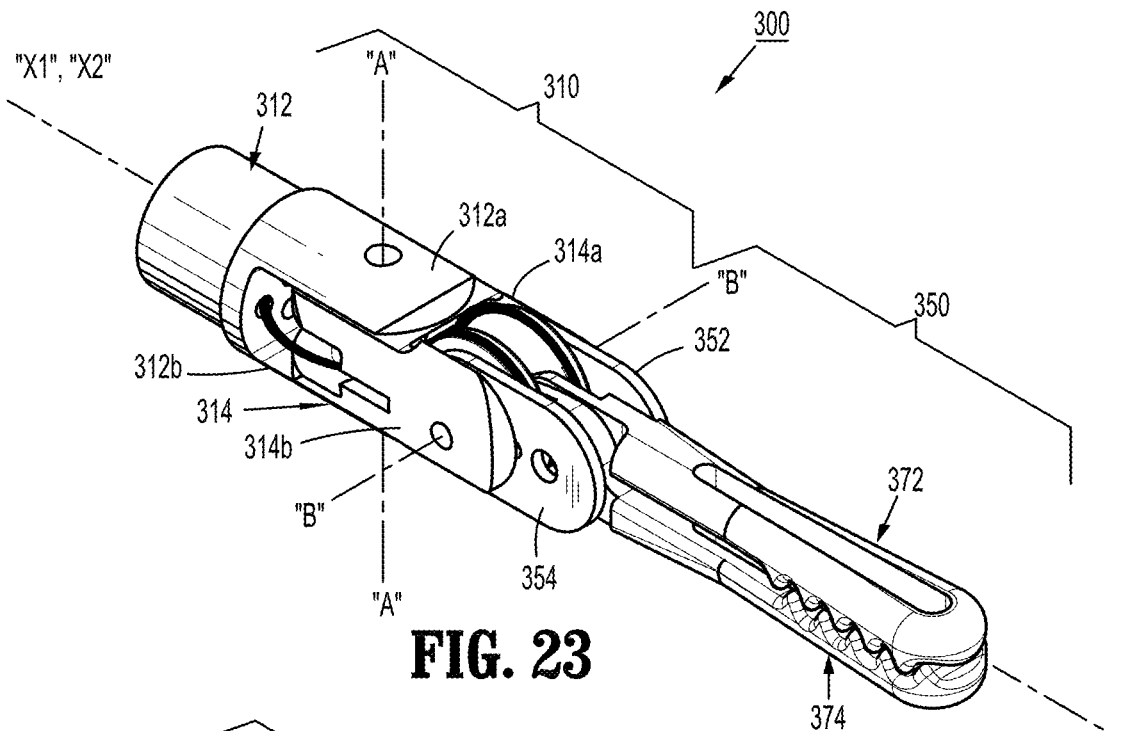
FIG. 23 is a perspective view of an end effector, according to yet another embodiment of the present disclosure, for use in the medical work station of FIG. 1A, illustrating a jaw assembly thereof in a closed condition.
Figure 24:
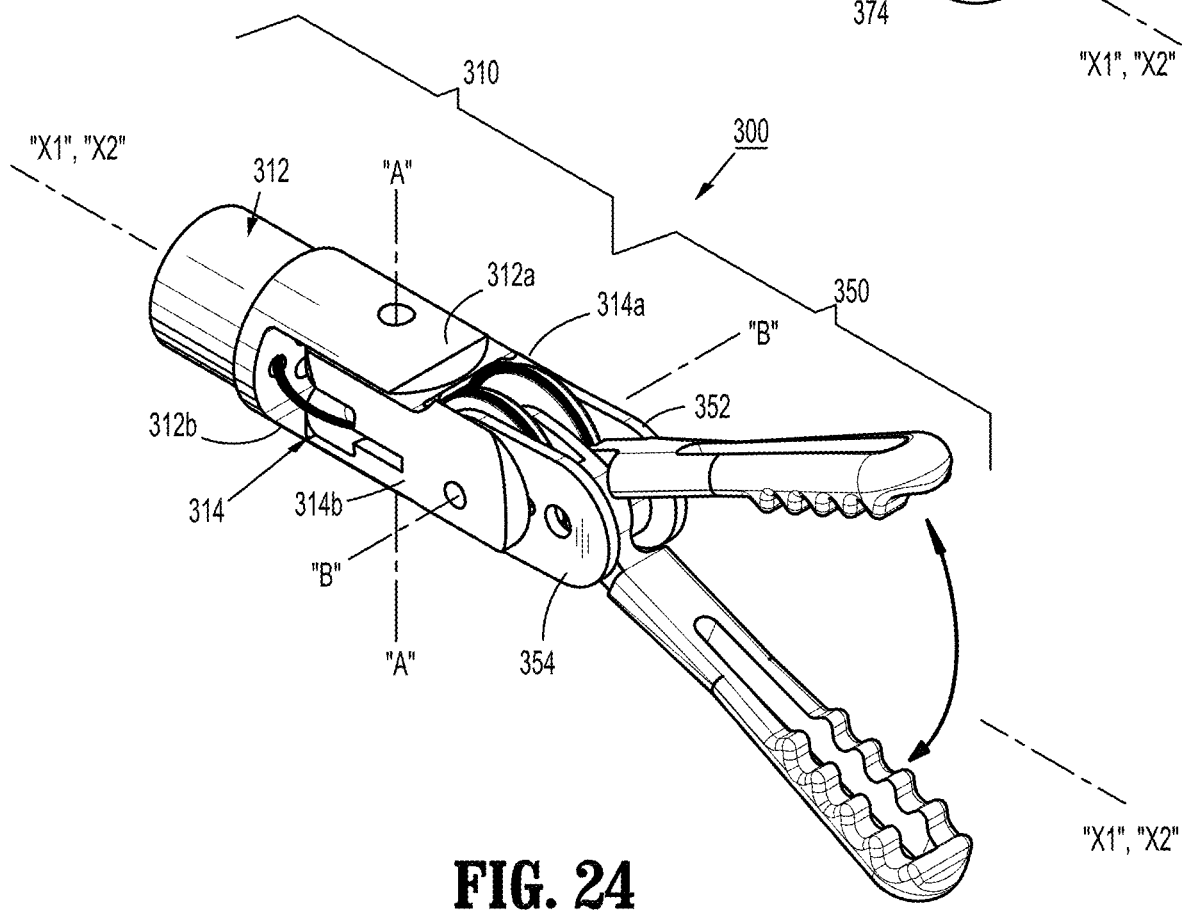
FIG. 24 is a perspective view of the end effector of FIG. 23 illustrating the jaw assembly thereof in an open condition.
Figure 25:
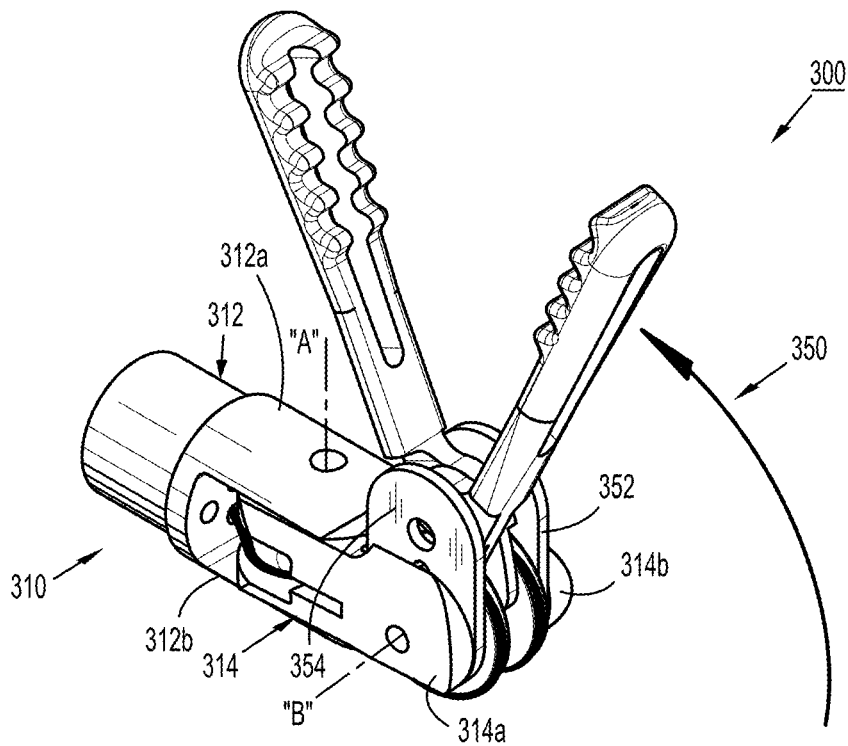
FIG. 25 is a perspective view of the end effector of FIG. 23 illustrating the jaw assembly thereof in an open and articulated condition.
Figure 26:
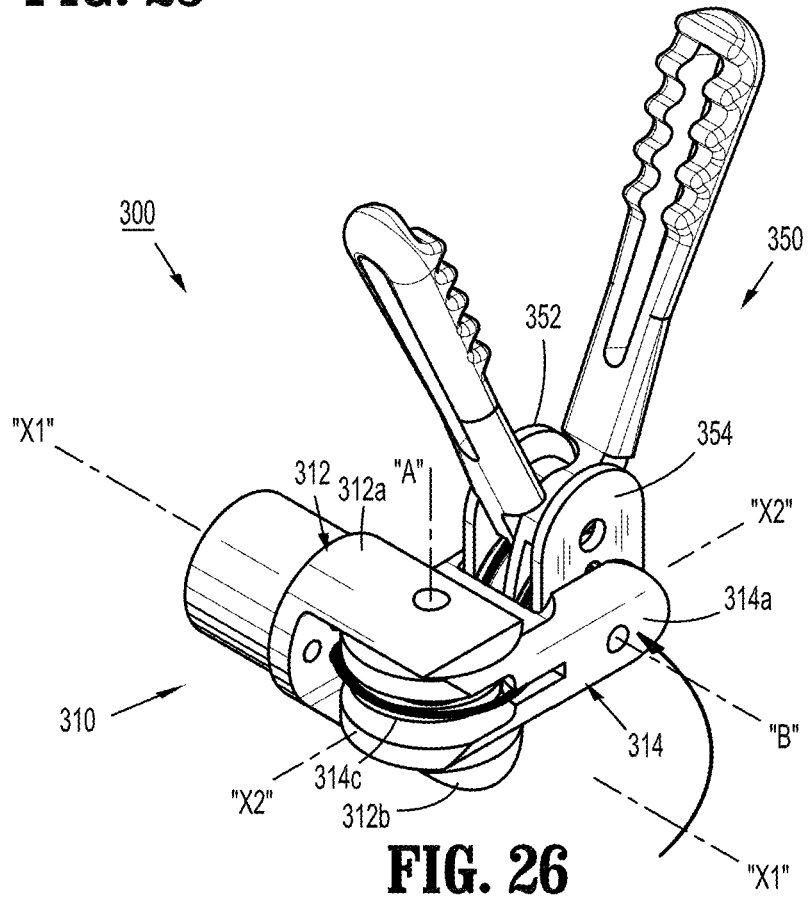
FIG. 26 is a perspective view of the end effector of FIG. 23 illustrating the jaw assembly thereof in an open and articulated condition, and illustrating a wrist assembly thereof in an articulated condition.
Figure 27:
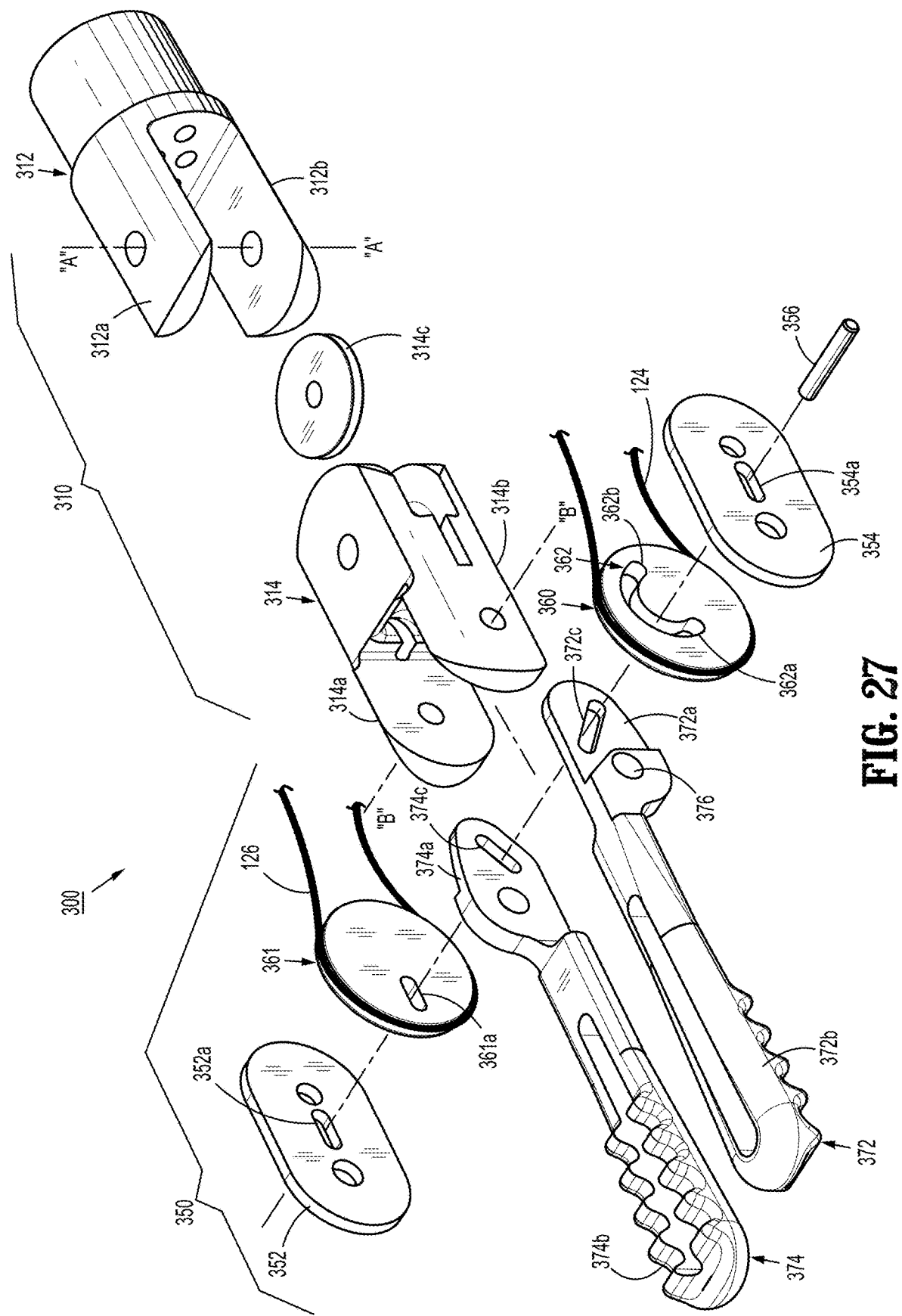
FIG. 27 is a perspective view, with parts separated, of the end effector of FIG. 23.

As shown in FIGS. 21 and 22, a pin or the like 272d, 274d pivotally and slidably connects each proximal end 272a, 274a of respective jaw 272, 274 to a respective cam slot 262, 264 formed in cam pulley 260. In use, as will be described in greater detail below, as cam pulley 260 is rotated in either a clockwise or counter clockwise direction, jaws 272, 274 will be caused to be opened or closed accordingly.

A single second cable (not shown) is at least partially wrapped around cam pulley 260 and secured to at least one point thereof, or that the single second cable may be wrapped at least once around cam pulley 260, in the manner of a capstan. The single second cable may include proximal ends that extend through robot arm 2 or 3 and operatively associated with a respective third motor and fourth motor (not shown) of control device 4. While a single second cable is described, it is contemplated that a second pair of cables (not shown) including respective distal ends may be secured to opposed sides of cam pulley 260, or wrapped at least 180° around cam pulley 260 and secured thereto, and including respective proximal ends extending through robot arm 2 or 3 and operatively associated with a respective third motor and fourth motor (not shown) of control device 4.

In operation, in order to pivot end effector 200 about first pivot axis "A-A" of wrist assembly 210, it is contemplated that one of the first pair of cables (not shown) is drawn in a proximal direction as a result of an input from control device 4. Depending on which one of the first pair of cables is drawn in a proximal direction will determine which direction of pivot, about first pivot axis "A-A," is achieved.

Additionally, in operation, in order to pivot jaws 272, 274 of end effector 200 about second pivot axis "B-B" of jaw assembly 250, it is contemplated that one of the second pair of cables (not shown) is drawn in a proximal direction as a result of an input from control device 4. Depending on which one of the second pair of cables is drawn in a proximal direction will determine which direction of pivot, about second pivot axis "B-B," is achieved.

Also in operation, in order to open or close jaws 272, 274 of end effector 200, about pivot point 276 of jaws 272, 274, it is contemplated that one of the second pair of cables is drawn in a proximal direction as a result of an input from control device 4. Depending on which one of the second pair of cables is drawn in a proximal direction will determine which direction cam pulley 260 is rotated (about pivot/rotation axis "B-B") and thus whether jaws 272, 274 are opened or closed. Specifically, as cam pulley 260 is rotated in a first direction, the pins 272d, 274d connecting jaws 272, 274 to cam pulley 260 are slid or cammed through respective cam slots 262, 264 and drawn radially inward to thereby open jaws 272, 274. Likewise, as cam pulley 260 is rotated in a second direction, the pins 272d, 274d connecting jaws 272, 274 to cam pulley 260 are slid or cammed through respective cam slots 262, 264 and pushed radially outward to thereby close jaws 272, 274.

Turning now to FIGS. 23-38, an end effector for connection to robot arms 2, 3 and for manipulation by control device 4, in accordance with yet another embodiment of the present disclosure, is generally designated as 300. End effector 300 is substantially similar to end effectors 100 and 200 and thus will only be described in detail herein to the extent necessary to describe differences in construction and/or operation from those of end effectors 100 and 200.

End effector 300 includes a wrist assembly 310, and a jaw assembly 350 pivotally connected to wrist assembly 310. Wrist assembly 310 includes a proximal hub 312 defining a first longitudinal axis "X1-X1," and a first pivot axis "A-A" that is oriented orthogonal to the first longitudinal axis "X1-X1." Wrist assembly 310 further includes a distal hub 314 pivotally connected to proximal hub 312. Distal hub 314 defines a second longitudinal axis "X2-X2," and a second pivot axis "B-B" that is oriented orthogonal to the first pivot axis "A-A" and orthogonal to the first longitudinal axis "X1-X1." In an embodiment, when the first longitudinal axis "X1-X1" is parallel with the second longitudinal axis "X2-X2" (i.e., end effector 300 is in an axially aligned orientation), second pivot axis "B-B" may extend through first longitudinal axis "X1-X1."

Figure 30:
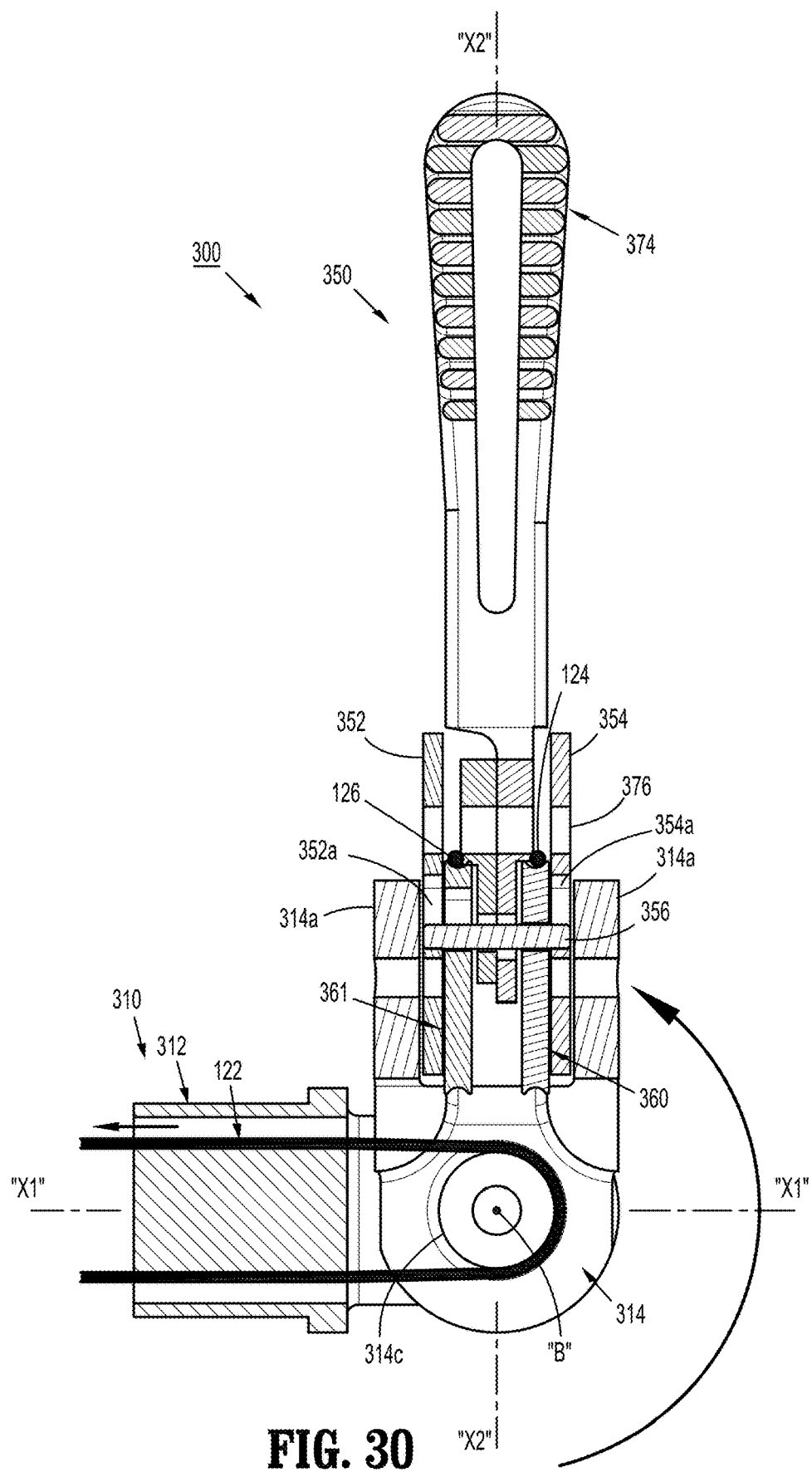
FIG. 30 is a cross-sectional view of the end effector of FIG. 28, as taken through section line 29-29 of FIG. 28, illustrating the jaw assembly in an articulated condition.
Figure 35:
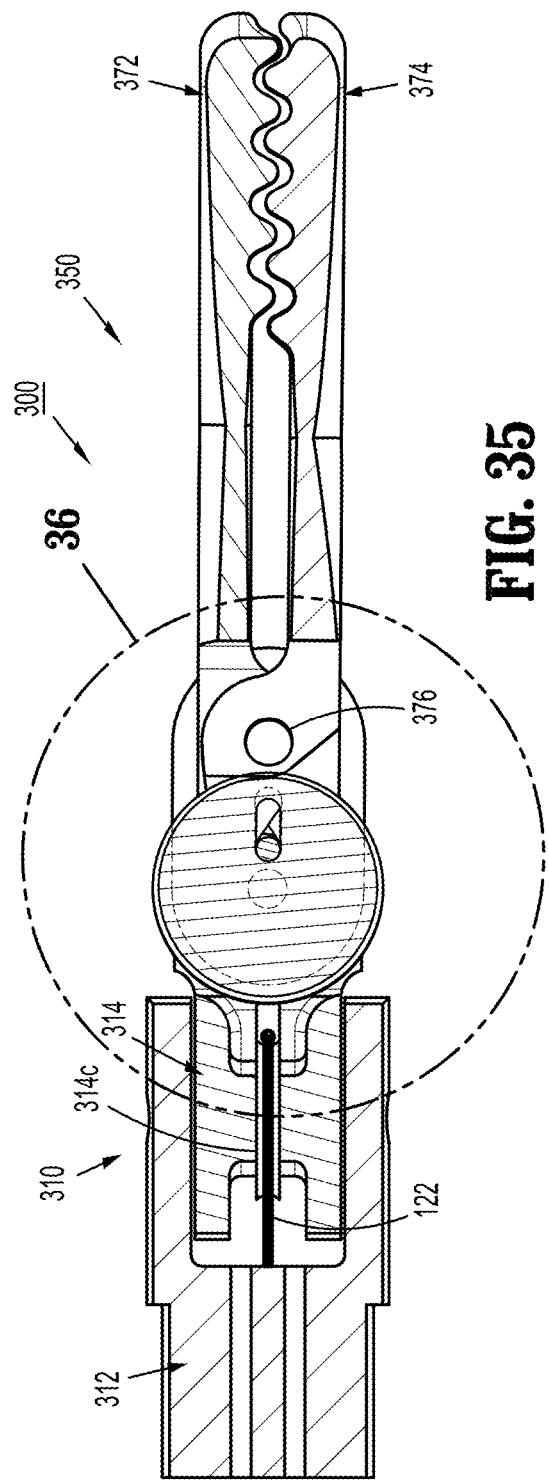
FIG. 35 is a cross-sectional view of the end effector of FIG. 23, as taken through section line 35-35 of FIG. 29, illustrating the jaw assembly in the closed and non-articulated condition.
Figure 36:
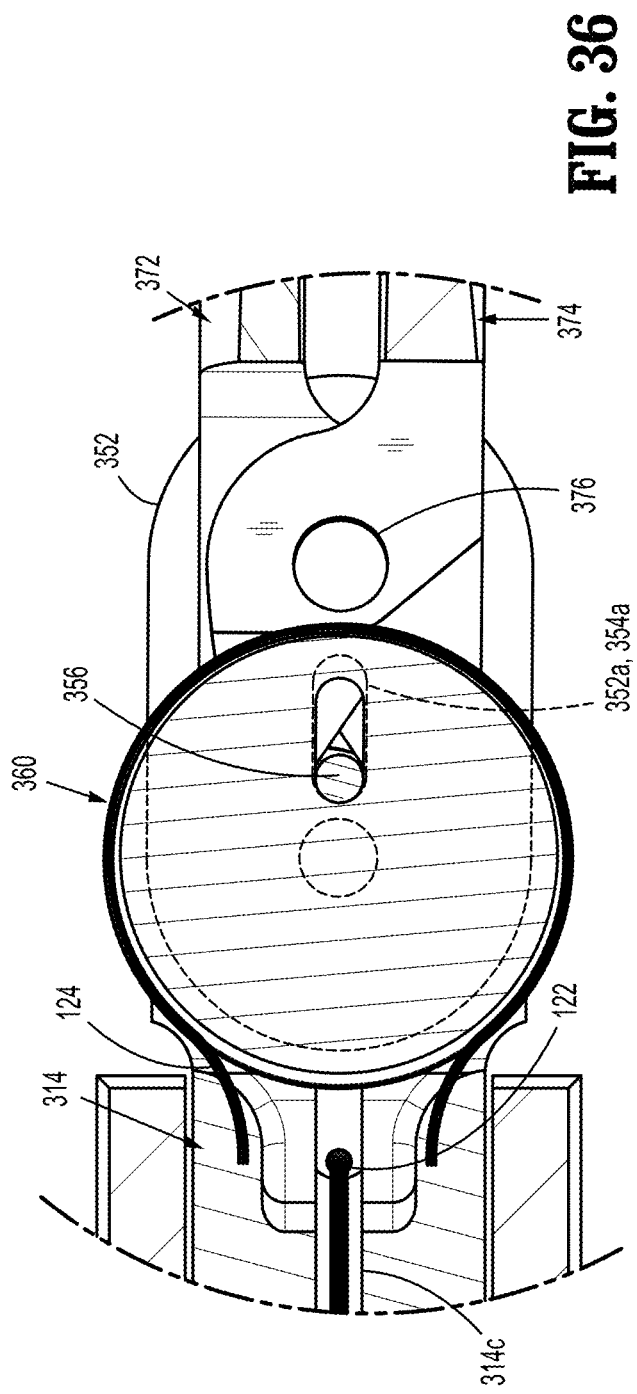
FIG. 36 is an enlarged view of the indicated area of detail of FIG. 35.
Figure 37:
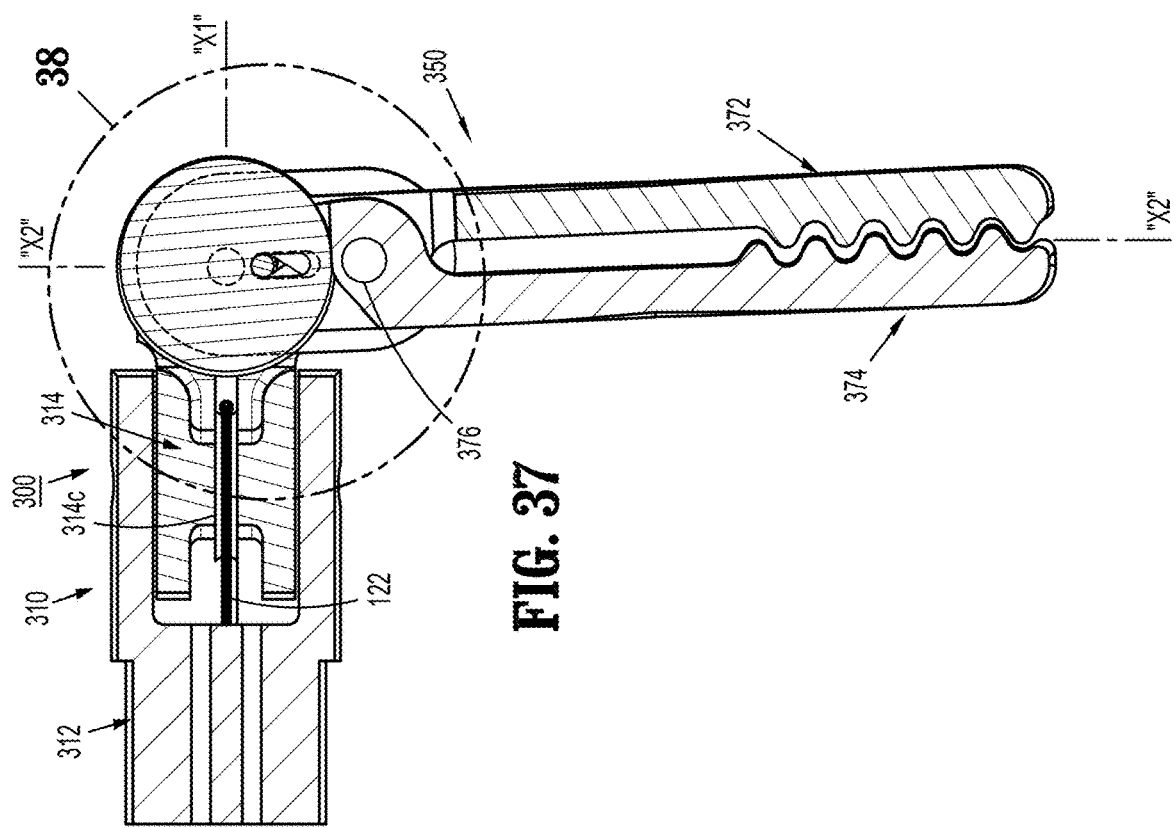
FIG. 37 is a cross-sectional view of the end effector of FIG. 23, as taken through section line 35-35 of FIG. 29, illustrating the jaw assembly in the closed and articulated condition.
Figure 38:
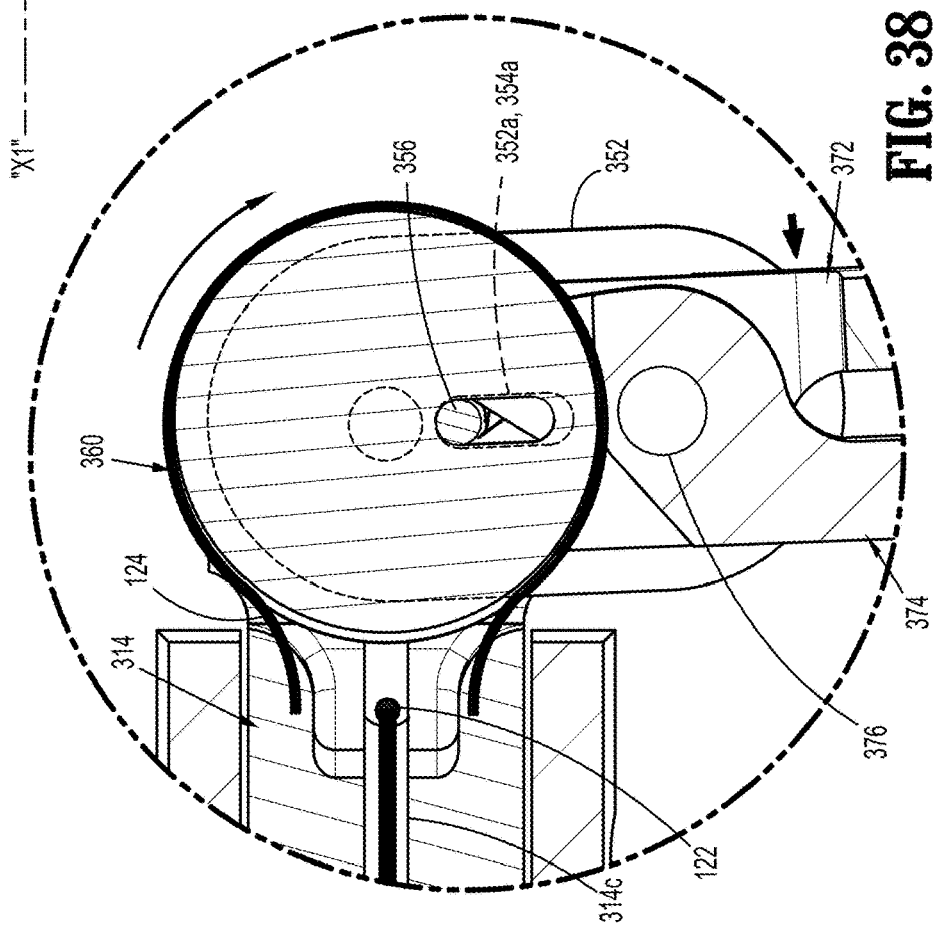
FIG. 38 is an enlarged view of the indicated area of detail of FIG. 37.
Figure 39:
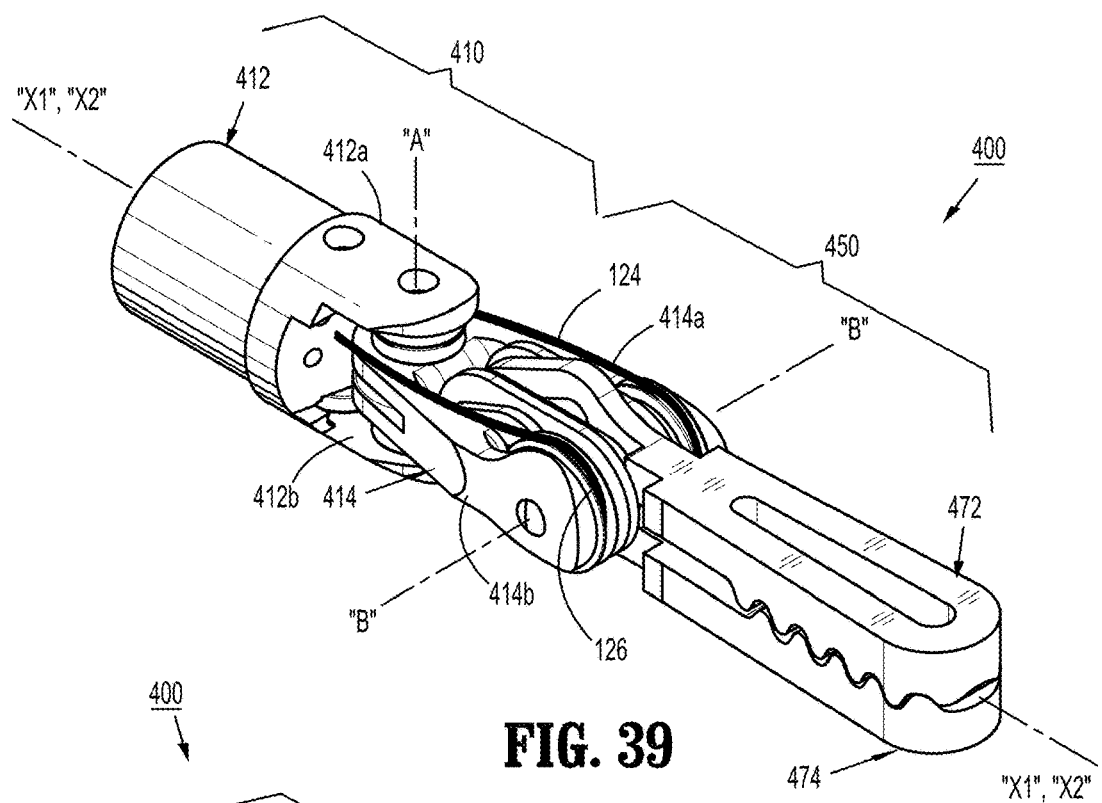
FIG. 39 is a perspective view of an end effector, according to still another embodiment of the present disclosure, for use in the medical work station of FIG. 1A, illustrating a jaw assembly thereof in a closed condition.
Figure 40:
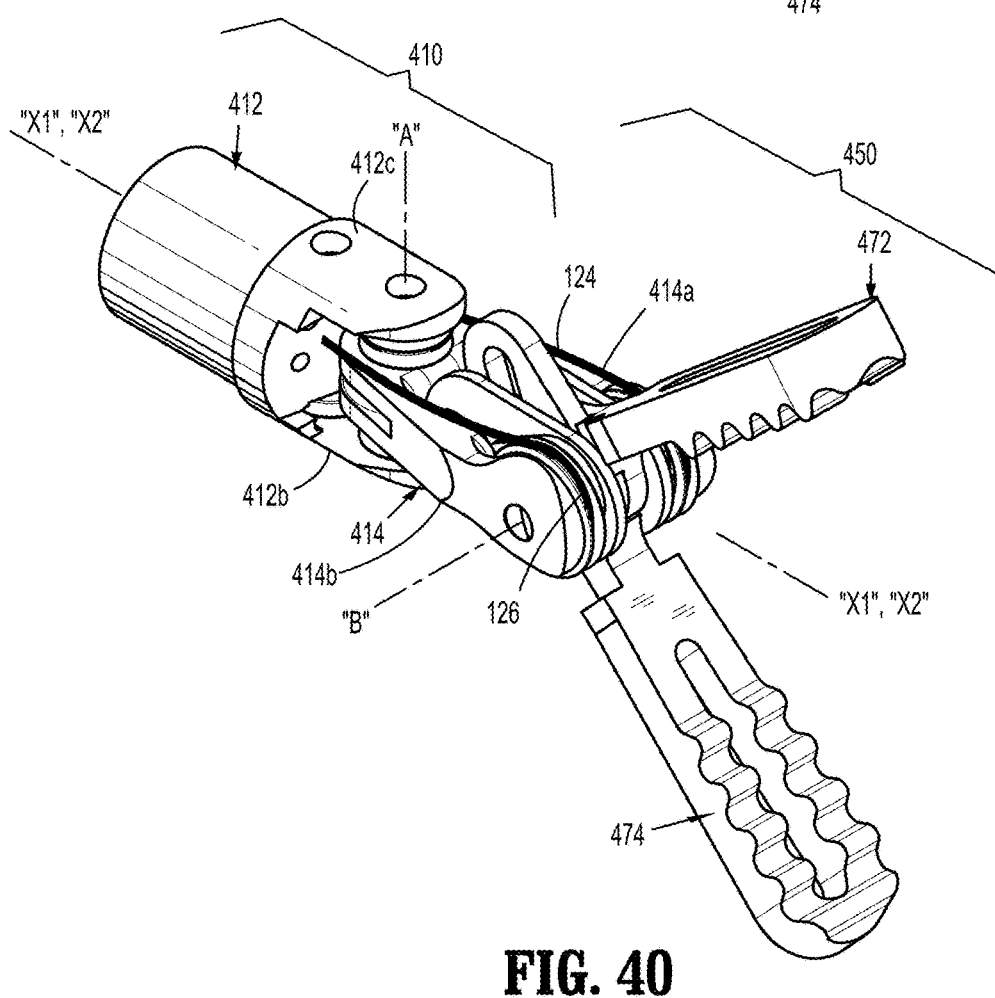
FIG. 40 is a perspective view of the end effector of FIG. 39 illustrating the jaw assembly thereof in an open condition.
Figure 41:
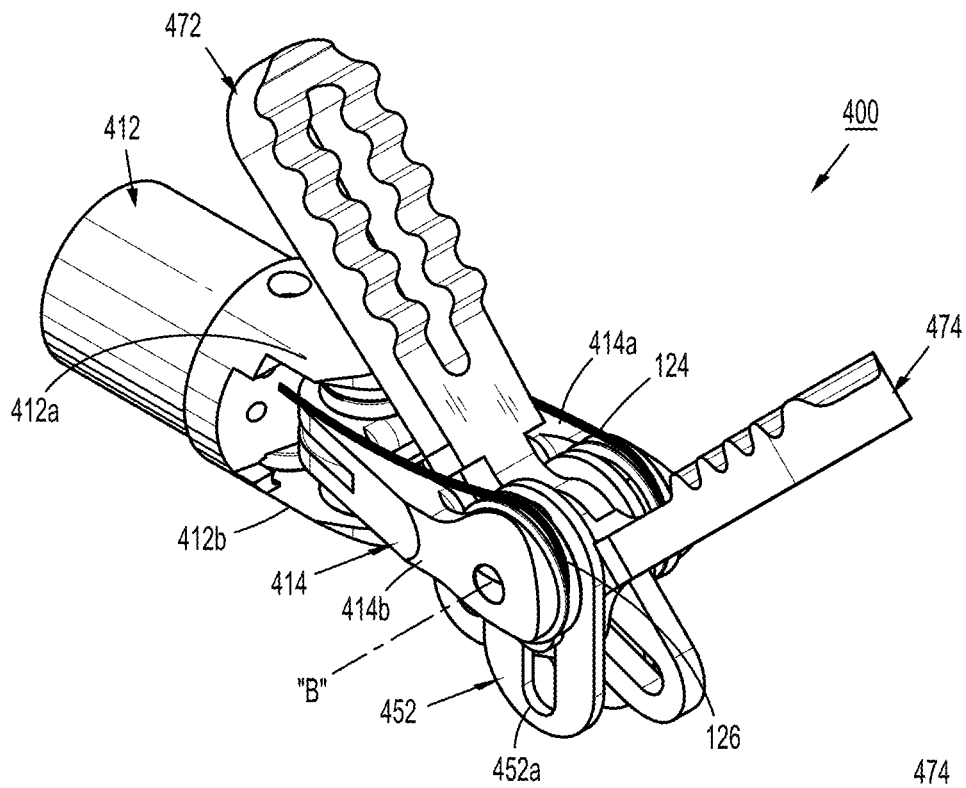
FIG. 41 is a perspective view of the end effector of FIG. 39 illustrating the jaw assembly thereof in an open and articulated condition.
Figure 42:
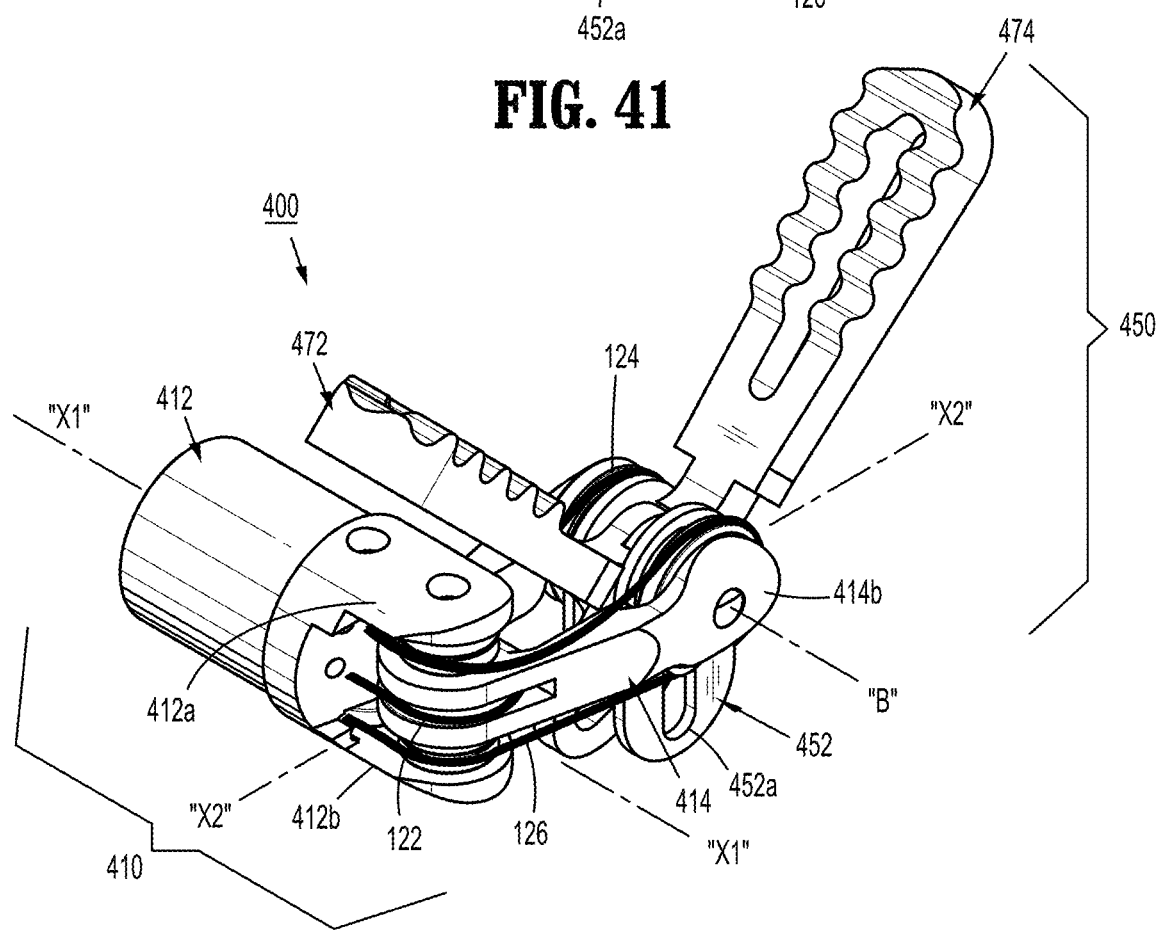
FIG. 42 is a perspective view of the end effector of FIG. 39 illustrating the jaw assembly thereof in an open and articulated condition, and illustrating a wrist assembly thereof in an articulated condition.
Figure 43:
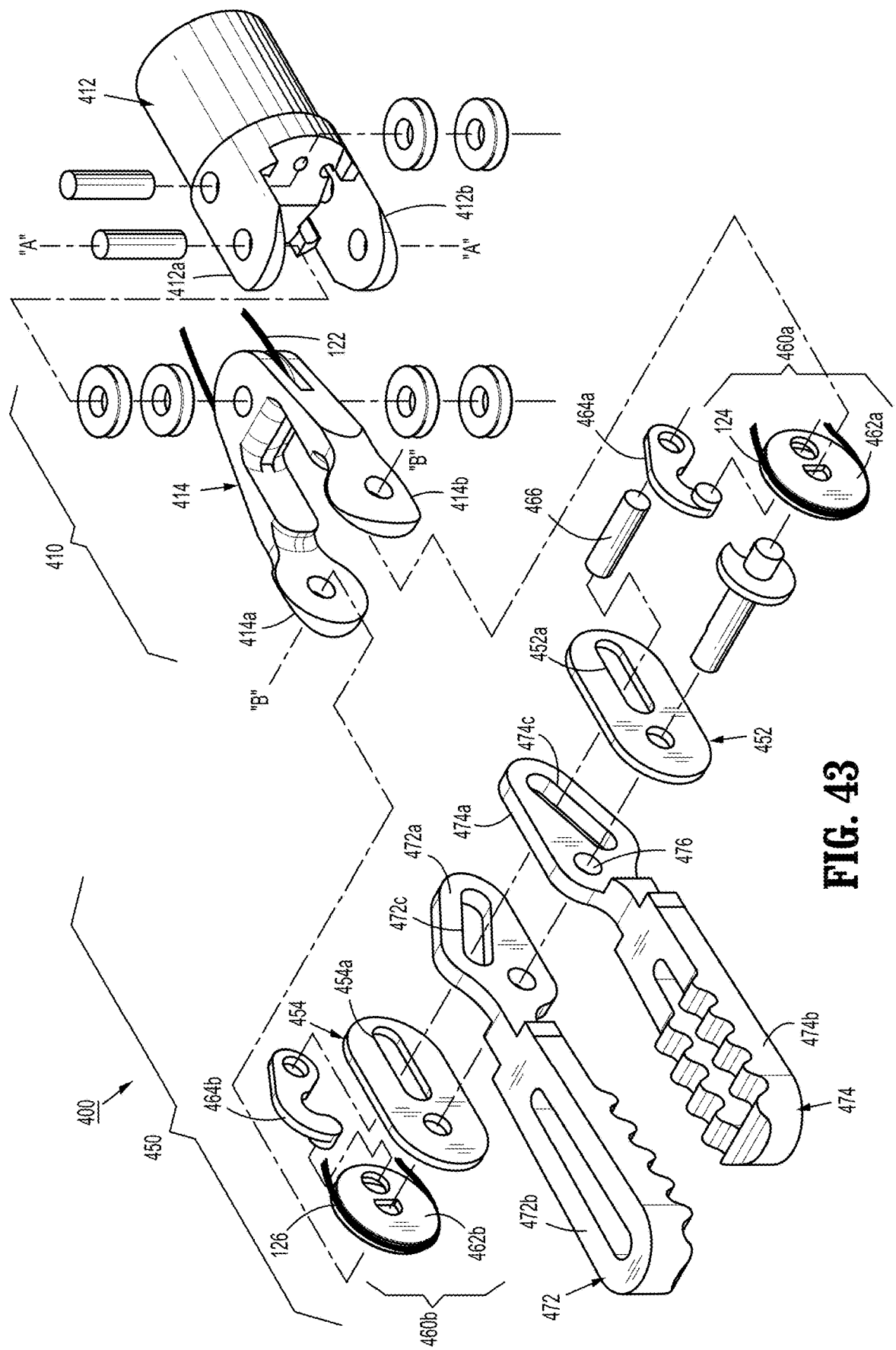
FIG. 43 is a perspective view, with parts separated, of the end effector of FIG. 39.

With reference to FIGS. 29 and 30, a single first cable 122 is at least partially wrapped around a cam plate 314c supported in distal hub 314 and secured to at least one point thereof, or that the single first cable 122 may be wrapped at least once around cam plate 314c, in the manner of a capstan. Single first cable 122 may include proximal ends that extend through robot arm 2 or 3 and operatively associated with a respective first motor and second motor (not shown) of control device 4. While a single first cable 122 is shown and described, it is contemplated that a first pair of cables (not shown) including respective distal ends may be secured to opposed sides of cam plate 314c, or wrapped at least 180° around cam plate 314c and secured thereto, and including respective proximal ends extending through robot arm 2 or 3 and operatively associated with a respective first motor and second motor (not shown) of control device 4.

With continued reference to FIGS. 23-38, end effector 300 includes a jaw assembly 350 having a pair of spaced apart support or cam plates, or cam pulleys 352, 354 pivotally connected to distal hub 314 of wrist assembly 310, so as to be pivotable about second pivot axis "B-B." Each support plate 352, 354 defines a respective axially extending slot 352a, 354a formed therein.

Jaw assembly 350 further includes a first cam pulley 360 also pivotally connected to upright supports of distal hub 314 of wrist assembly 310 so as to also be pivotable about second pivot axis "B-B." Cam pulley 360 is substantially disc-shaped and defines an arcuate cam slot 362 formed therein. Cam slot 362 includes a first end 362a spaced a first radial distance away from second pivot axis "B-B," and a second end 362b spaced a second radial distance away from second pivot axis "B," wherein the second radial distance is greater than the first radial distance. A shape or configuration of cam slot 362 may be modified or selected so as to vary or alter a closing/opening characteristic of jaw assembly 350, such as for example, to increase a clamping force (i.e., act as a force multiplier) of the jaw assembly 350 as the jaw assembly 350 is brought to a fully closed condition.

Jaw assembly 350 further includes a second cam pulley 361 also pivotally connected to upright supports of distal hub 314 of wrist assembly 310 so as to also be pivotable about second pivot axis "B-B." Cam pulley 361 is substantially disc-shaped and defines a radially extending slot 361a formed therein.

Jaw assembly 350 also includes a pair of jaws 372, 374 pivotally connected to support plates 352, 354 at a common pivot point 376 about which each jaw 372, 374 pivots. Pivot point 376 is spaced an axial distance distally of second pivot axis "B-B" when end effector 300 is in a axially aligned orientation (i.e., when the first longitudinal axis "X1-X1" is parallel with the second longitudinal axis "X2-X2").

Each jaw 372, 374 includes a respective proximal end 372a, 374a, and a respective distal end 372b, 374b. Pivot point 376 defines a pivot axis that is parallel to second pivot axis "B-B" of distal hub 314. Each proximal end 372a, 374a extends proximally of pivot point 376, and each distal end 372b, 374b extends distally of pivot point 376. Each proximal end 372a, 374a defines a respective angled cam slot 372c, 374c formed therein. Specifically, each angled cam slot 372c, 374c may include a distal end axially aligned or substantially axially aligned with pivot point 376, and a proximal end curving in opposite directions away from one another.

A pin or the like 356 pivotally and slidably connects each angled cam slot 372c, 374c of respective proximal end 372a, 374a of respective jaw 372, 374 to cam slot 362 formed in cam pulley 360, and to slot 361a of cam pulley 361. Pin 356 is also slidably disposed within axially extending slots 352a, 354a formed in support plates 352, 354. In use, as will be described in greater detail below, as cam pulleys 360, 361 are rotated in either a clockwise and/or counter clockwise direction, jaws 372, 374 will be caused to be opened, closed and/or pivoted accordingly.

A single second cable 124 is at least partially wrapped around cam pulley 360 and secured to at least one point thereof, or that the single second cable 124 may be wrapped at least once around cam pulley 360, in the manner of a capstan. Single second cable 124 may include proximal ends that extend through robot arm 2 or 3 and operatively associated with a respective third motor and fourth motor (not shown) of control device 4. While a single second cable 124 is shown and described, it is contemplated that a second pair of cables (not shown) including respective distal ends may be secured to opposed sides of cam pulley 360, or wrapped at least 180° around cam pulley 360 and secured thereto, and including respective proximal ends extending through robot arm 2 or 3 and operatively associated with a respective third motor and fourth motor (not shown) of control device 4.

Further, a single third cable 126 may be at least partially wrapped around cam pulley 361 and secured to at least one point thereof, or that the single third cable 126 may be wrapped at least once around cam pulley 361, in the manner of a capstan. The single third cable 126 may include proximal ends that extend through robot arm 2 or 3 and operatively associated with a respective fifth motor (not shown) and sixth motor (not shown) of control device 4. While a single third cable 126 is described, it is contemplated that a third pair of cables (not shown) including respective distal ends may be secured to opposed sides of cam pulley 361, or wrapped at least 180° around cam pulley 361 and secured thereto, and including respective proximal ends extending through robot arm 2 or 3 and operatively associated with a respective fifth motor (not shown) and sixth motor (not shown) of control device 4.

In operation, in order to pivot end effector 300 about first pivot axis "A-A" of wrist assembly 310, it is contemplated that one proximal end of first cable 122 is drawn in a proximal direction as a result of an input from control device 4 to activate a first motor (not shown), and optionally activate a second motor (not shown) to let out the other proximal end of first cable 122. Depending on which proximal end of first cable 122 is drawn in a proximal direction will determine which direction of pivot, about first pivot axis "A-A," is achieved.

Additionally, in operation, in order to pivot jaws 372, 374 of end effector 300 about second pivot axis "B-B" of jaw assembly 350, it is contemplated that one proximal end of the third cable 126 is drawn in a proximal direction as a result of an input from control device 4 to activate a third motor (not shown), and optionally activate a fourth motor (not shown) to let out the other proximal end of the third cable 126. Depending on which proximal end of third cable 126 is drawn in a proximal direction will determine which direction of pivot, about second pivot axis "B-B," is transmitted to cam pulley 361 to thus pivot jaws 272, 274.

Also in operation, in order to open or close jaws 372, 374 of end effector 300, about pivot point 376 of jaws 372, 374, it is contemplated that one proximal end the second cable 124 is drawn in a proximal direction as a result of an input from control device 4 to activate the third motor or a fifth motor (not shown), and optionally activate the fourth motor or a sixth motor (not shown) to let out the other proximal end of the second cable 124. Depending on which proximal end of the second cable 124 is drawn in a proximal direction will determine which direction cam pulley 360 is rotated (about pivot/rotation axis "B") and thus whether jaws 372, 374 are opened or closed. Specifically, with cam pulley 361 held stationary, as cam pulley 360 is rotated in a first direction, the pin 356 connecting angled cam slot 372c, 374c of jaws 372, 374 to cam slot 362 of cam pulley 360 is slid or cammed proximally through cam slots 372c, 374c of jaws 372, 374 and drawn radially inward through cam slot 362 of cam pulley 360, and pulled or cammed proximally through axial slots 352a, 354a of support plate 352, 354, to thereby open jaws 372, 374. Likewise, with cam pulley 361 held stationary, as cam pulley 360 is rotated in a second direction, the pin 356 connecting arcuate cam slot 372c, 374c of jaws 372, 374 to cam slot 362 of cam pulley 360 is slid or cammed distally through cam slots 372c, 374c of jaws 372, 374 and pushed radially outward through cam slot 362 of cam pulley 360, and pushed or cammed distally through axial slots 352a, 254a of support plate 352, 354, to thereby close jaws 372, 374.

Turning now to FIGS. 39-50, an end effector for connection to robot arms 2, 3 and for manipulation by control device 4, in accordance with yet another embodiment of the present disclosure, is generally designated as 400. End effector 400 is substantially similar to end effectors 100-300 and thus will only be described in detail herein to the extent necessary to describe differences in construction and/or operation over end effectors 100-300.

End effector 400 includes a wrist assembly 410, and a jaw assembly 450 pivotally connected to wrist assembly 410. Wrist assembly 410 includes a proximal hub 412 defining a first longitudinal axis "X1-X1," and a first pivot axis "A-A" that is oriented orthogonal to the first longitudinal axis "X1-X1." Wrist assembly 410 further includes a distal hub 414 pivotally connected to proximal hub 412. Distal hub 414 defines a second longitudinal axis "X2-X2," and a second pivot axis "B-B" that is oriented orthogonal to the first pivot axis "A-A" and orthogonal to the first longitudinal axis "X1-X1." In an embodiment, when the first longitudinal axis "X1-X1" is parallel with the second longitudinal axis "X2-X2" (i.e., end effector 400 is in an axially aligned orientation), second pivot axis "B-B" may extend through first longitudinal axis "X1-X1."

Figure 46:
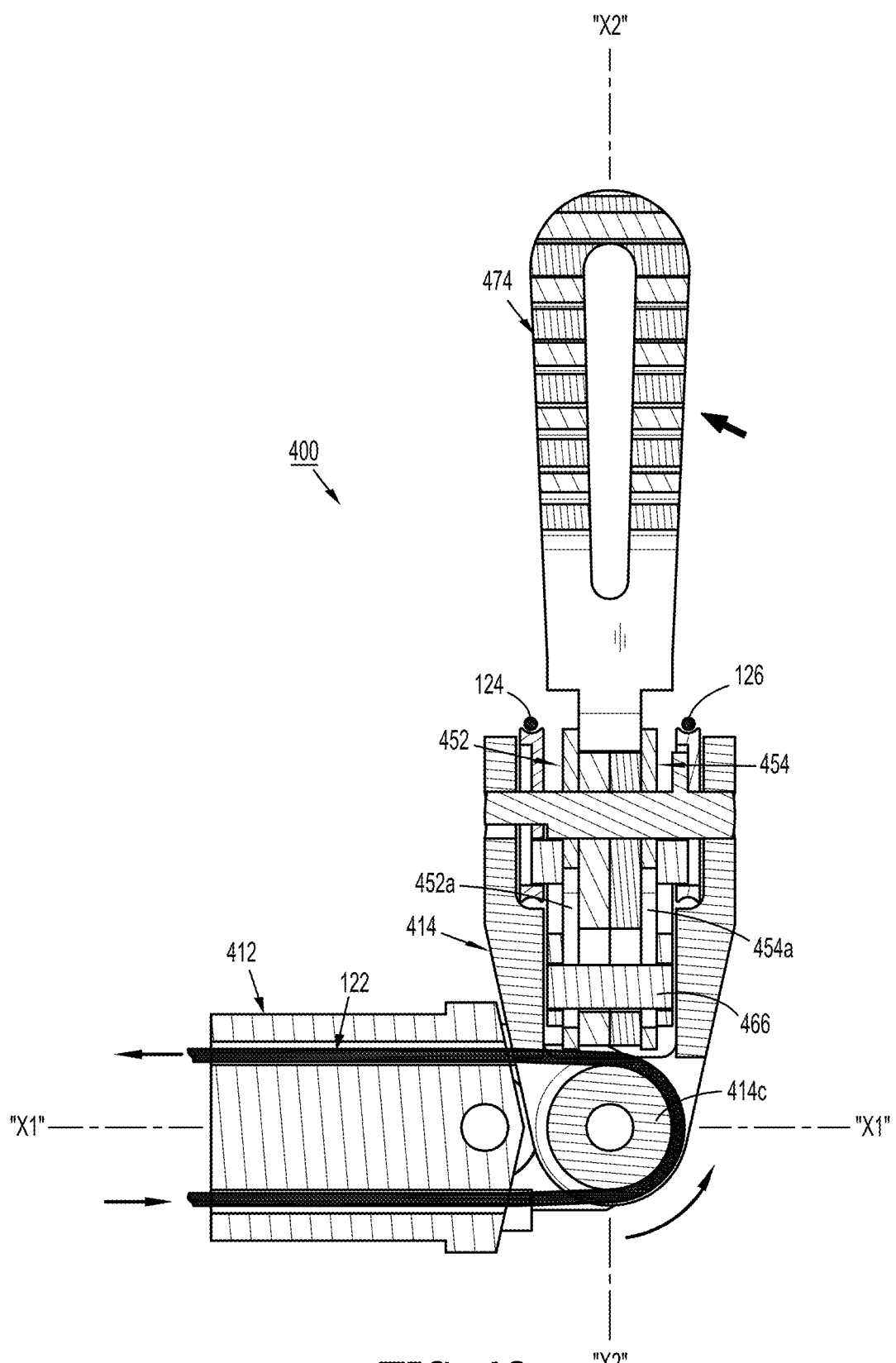
FIG. 46 is a cross-sectional view of the end effector of FIG. 44, as taken through section line 45-45 of FIG. 44, illustrating the jaw assembly in an articulated condition.
Figure 47:
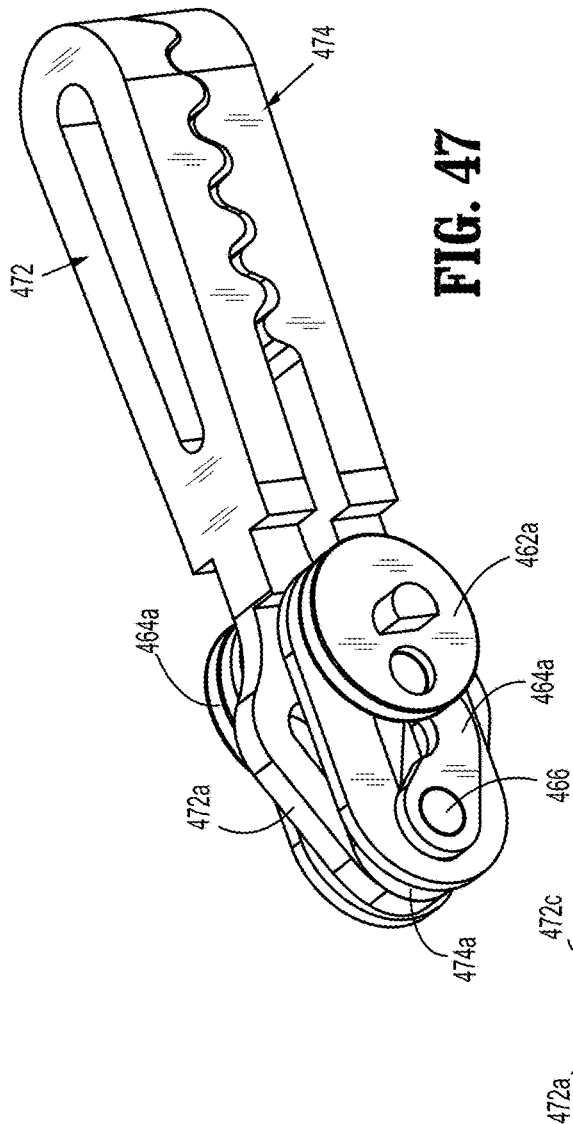
FIG. 47 is a rear, perspective view of the jaw assembly of the end effector of FIG. 39, illustrating the jaw assembly in the closed condition.
Figure 48:
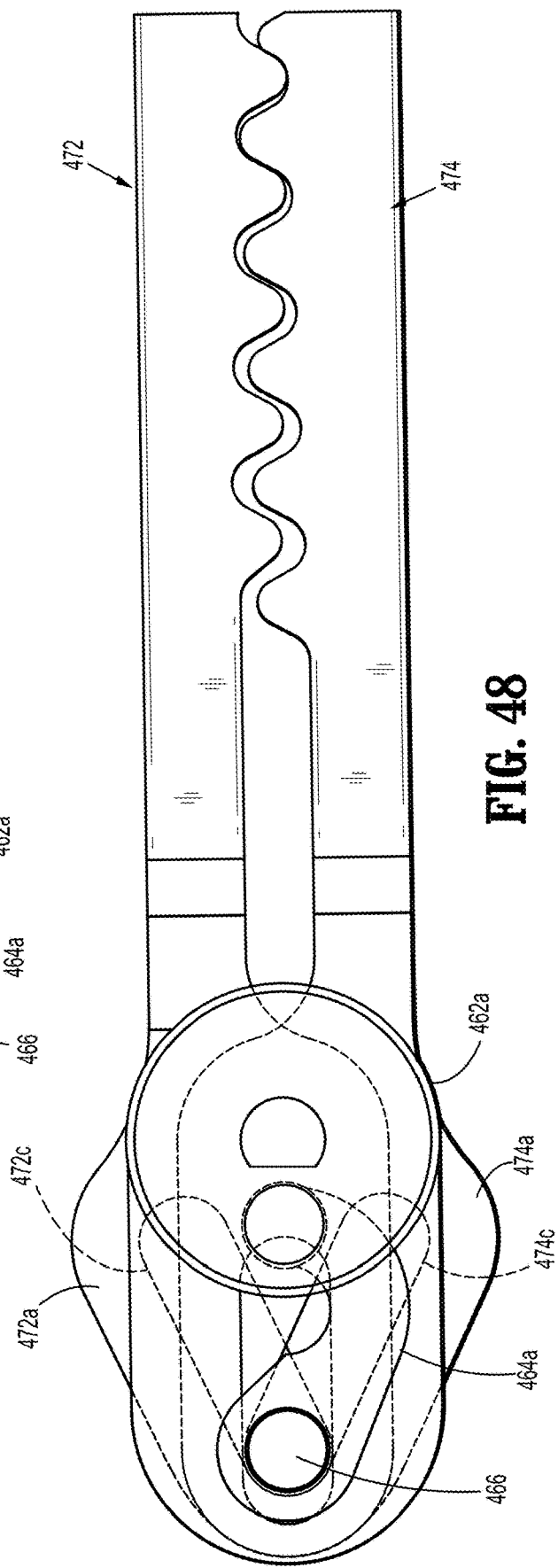
FIG. 48 is a side elevational view of the jaw assembly of FIG. 47.
Figure 51:
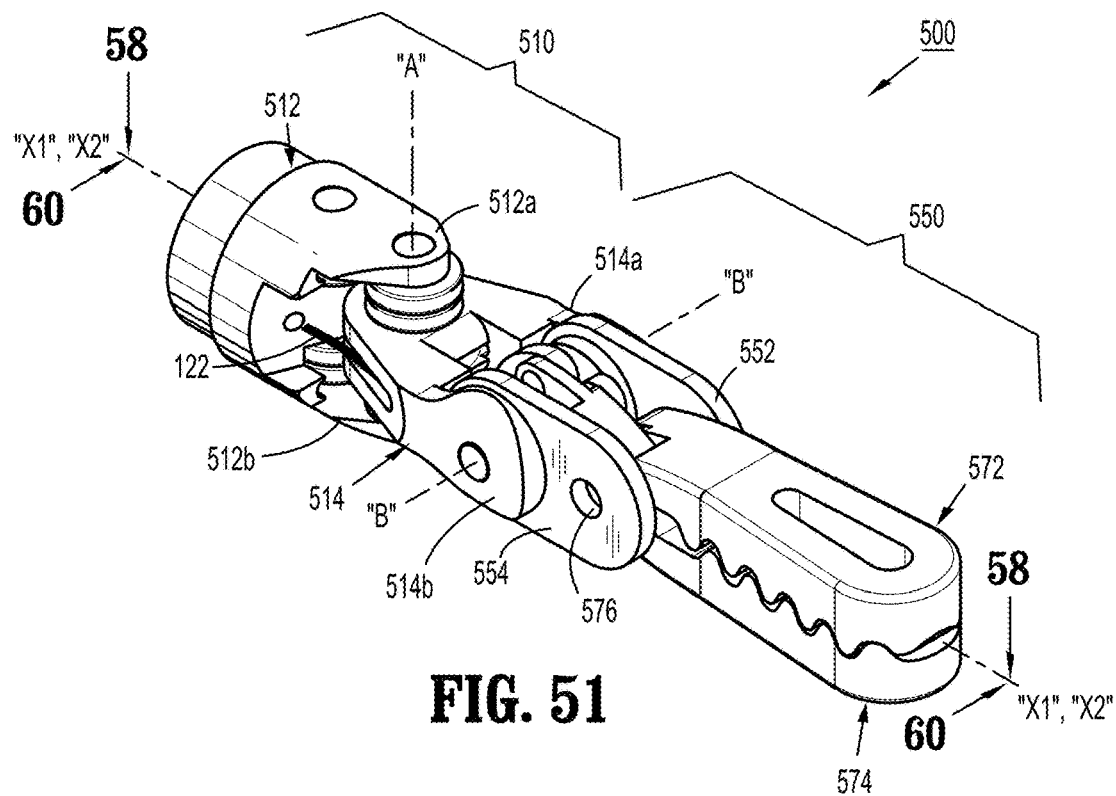
FIG. 51 is a perspective view of an end effector, according to a further embodiment of the present disclosure, for use in the medical work station of FIG. 1A, illustrating a jaw assembly thereof in a closed condition.
Figure 52:
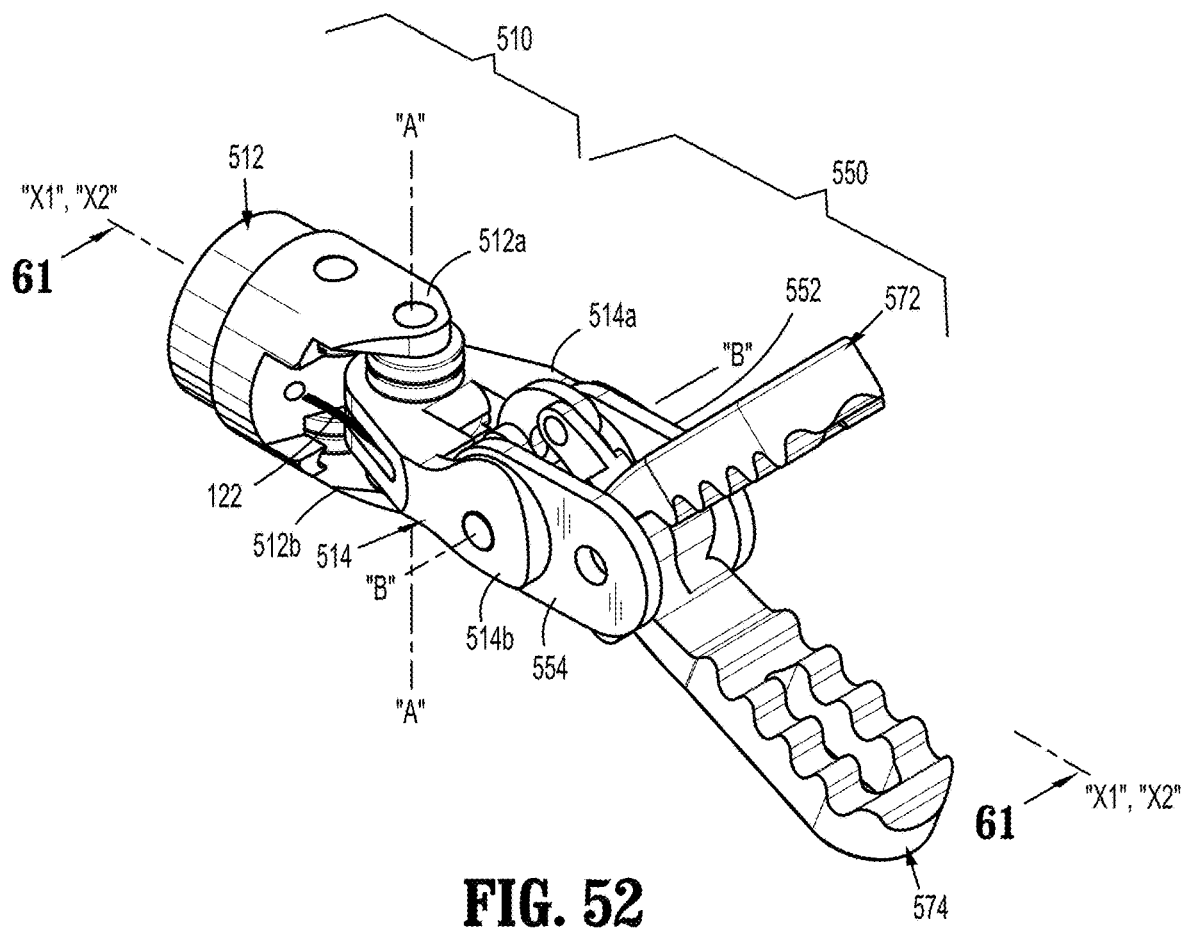
FIG. 52 is a perspective view of the end effector of FIG. 51 illustrating the jaw assembly thereof in an open condition.
Figure 53:
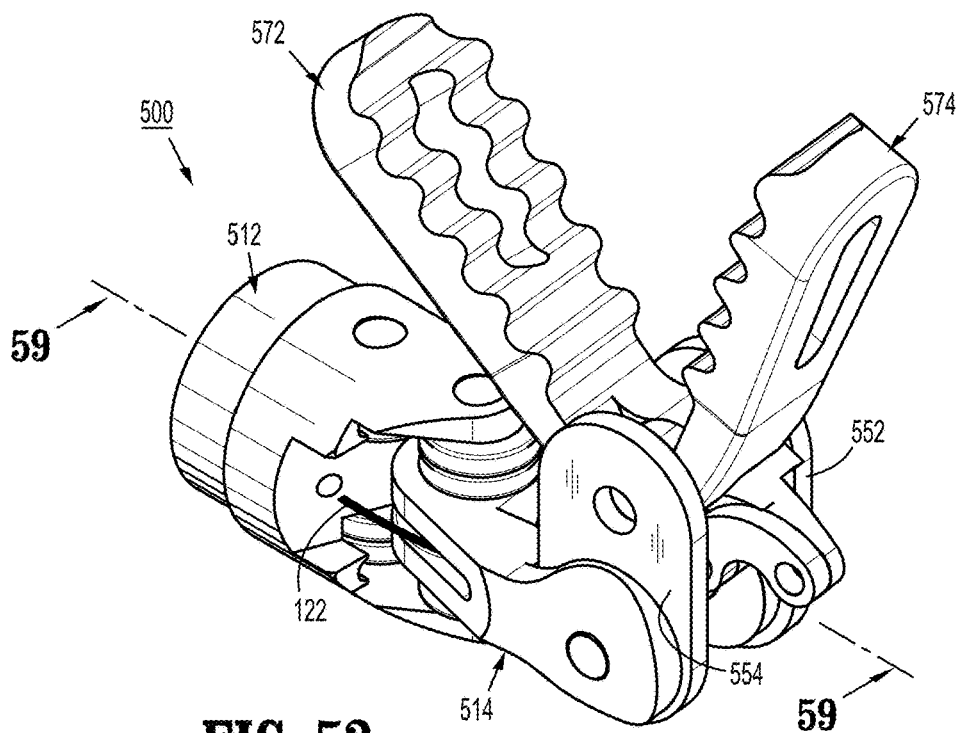
FIG. 53 is a perspective view of the end effector of FIG. 51 illustrating the jaw assembly thereof in an open and articulated condition.
Figure 54:
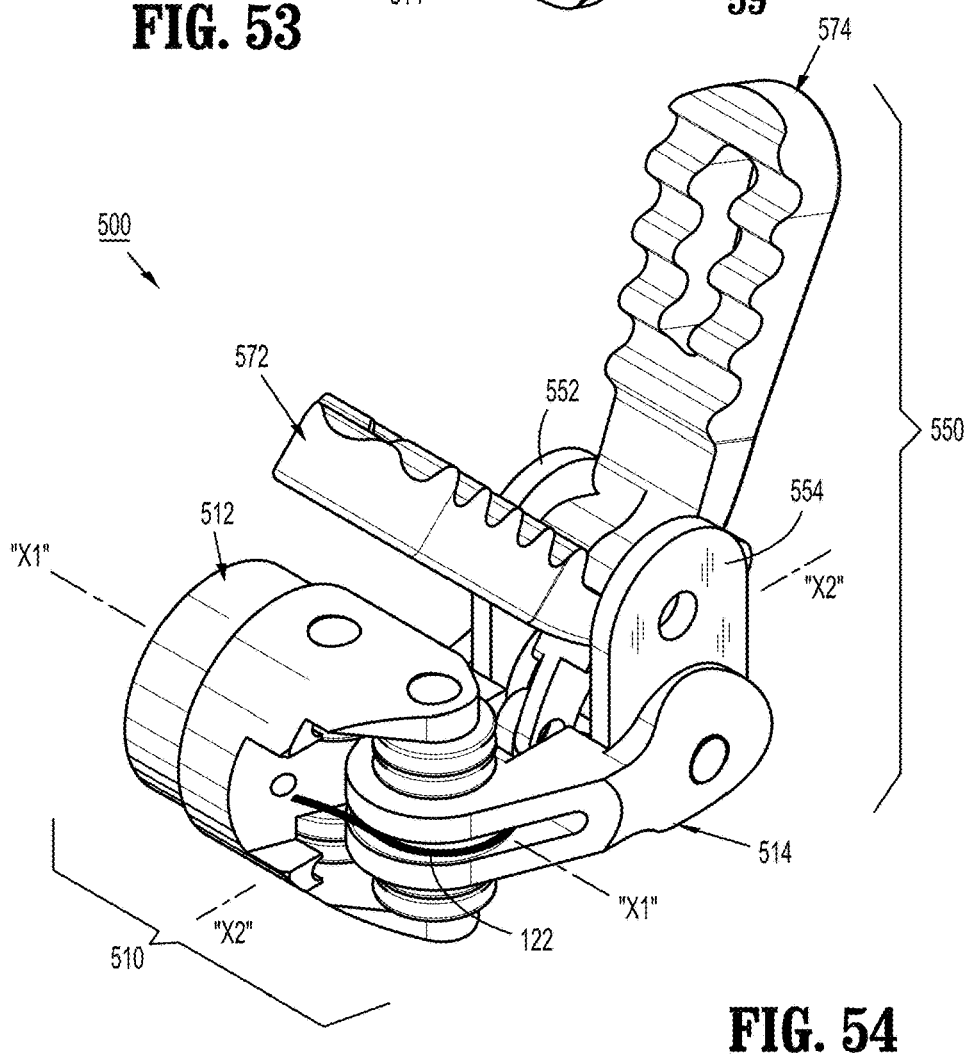
FIG. 54 is a perspective view of the end effector of FIG. 51 illustrating the jaw assembly thereof in an open and articulated condition, and illustrating a wrist assembly thereof in an articulated condition.

With reference to FIGS. 45 and 46, a single first cable 122 is at least partially wrapped around a cam pulley 414c of distal hub 414 and secured to at least one point thereof, or that the single first cable 122 may be wrapped at least once around cam pulley 414c, in the manner of a capstan. Single first cable 122 may include proximal ends that extend through robot arm 2 or 3 and operatively associated with a respective first motor and second motor (not shown) of control device 4. While a single first cable 122 is shown and described, it is contemplated that a first pair of cables (not shown) including respective distal ends may be secured to opposed sides of cam pulley 414c, or wrapped at least 180° around cam pulley 414c and secured thereto, and including respective proximal ends extending through robot arm 2 or 3 and operatively associated with a respective first motor and second motor (not shown) of control device 4.

With continued reference to FIGS. 39-50, end effector 400 includes a jaw assembly 450 having a pair of spaced apart support or cam plates, or cam pulleys 452, 454 pivotally connected to respective spaced apart upright supports 414a, 414b of distal hub 414 of wrist assembly 410, so as to be pivotable about second pivot axis "B-B." Each support plate 452, 454 defines a respective longitudinally extending slot 452a, 454a formed therein at a location proximal of second pivot axis "B-B."

Jaw assembly 450 further includes a pair of cam pulley assemblies 460a, 460b each having a cam plate 462a, 462b pivotally supported on spaced apart upright supports 414a, 414b of distal hub 414 along second pivot axis "B-B," and a respective cam link 464a, 464b pivotally interconnecting each cam plate 462a, 462b to a respective support plate 452, 454. Specifically, a distal end of each cam link 464a, 464b is pivotally connected to a respective cam plate 462a, 462b, and a proximal end of each cam link 464a, 464b is pivotally and slidably connected to slots 452a, 454a of support plates 452, 454 via a camming pin 466. A length of each cam link 464a, 464b may be modified or selected so as to vary or alter a closing/opening characteristic of jaw assembly 450, such as for example, to increase a clamping force (i.e., act as a force multiplier) of the jaw assembly 450 as the jaw assembly 450 is brought to a fully closed condition.

Jaw assembly 450 also includes a pair of jaws 472, 474 pivotally connected to support plates 452, 454, and to upright supports 414a, 414b of distal hub 414, at a common pivot point 476 about which each jaw 472, 474 pivots. Pivot point 476 is co-axial with second pivot "B-B".

Each jaw 472, 474 includes a respective proximal end 472a, 474a, and a respective distal end 472b, 474b. Each proximal end 472a, 474a extends proximally of pivot point 476, and each distal end 472b, 474b extends distally of pivot point 476. Each proximal end 472a, 474a defines a respective angled cam slot 472c, 474c formed therein. Specifically, each angled cam slot 472c, 474c may include a distal end axially aligned or substantially axially aligned with pivot point 476, and a proximal end curving in opposite directions away from one another.

As described above, a pin or the like 466 pivotally and slidably connects each angled cam slot 472c, 474c of respective proximal end 472a, 474a of respective jaw 472, 474 with slots 452a, 454a of support plates 452, 454. In use, as will be described in greater detail below, as cam plates 462a, 462b are rotated in either a clockwise or counter clockwise direction, jaws 472, 474 will be caused to be opened or closed accordingly.

As illustrated in FIGS. 39-46, a single second cable 124 may be at least partially wrapped around cam plate 462a and secured to at least one point thereof, or that the single second cable may be wrapped at least once around cam plate 462a, in the manner of a capstan. Single second cable 124 may include proximal ends that extend through robot arm 2 or 3 and operatively associated with a respective third motor and fourth motor (not shown) of control device 4. While a single second cable 124 is described, it is contemplated that a second pair of cables (not shown) including respective distal ends may be secured to opposed sides of cam plate 462a, or wrapped at least 180° around cam plate 462a and secured thereto, and including respective proximal ends extending through robot arm 2 or 3 and operatively associated with a respective third motor and fourth motor (not shown) of control device 4.

A single third cable 126 may be at least partially wrapped around cam plate 462b and secured to at least one point thereof, or that the single third cable 126 may be wrapped at least once around cam plate 462b, in the manner of a capstan. The single third cable 126 may include proximal ends that extend through robot arm 2 or 3 and operatively associated with a respective fifth motor (not shown) and sixth motor (not shown) of control device 4. While a single third cable 126 is described, it is contemplated that a third pair of cables (not shown) including respective distal ends may be secured to opposed sides of cam plate 462b, or wrapped at least 180° around cam plate 462b and secured thereto, and including respective proximal ends extending through robot arm 2 or 3 and operatively associated with a respective fifth motor (not shown) and sixth motor (not shown) of control device 4.

In operation, as seen in FIGS. 45 and 46, in order to pivot end effector 400 about first pivot axis "A-A" of wrist assembly 410, it is contemplated that one proximal end of first cable 122 is drawn in a proximal direction as a result of an input from control device 4 to activate a first motor (not shown), and optionally activate a second motor (not shown) to let out the other proximal end of first cable 122. Depending on which proximal end of first cable 122 is drawn in a proximal direction will determine which direction of pivot, about first pivot axis "A-A," is achieved.

Additionally, in operation, in order to pivot jaws 472, 474 of end effector 400 about second pivot axis "B-B" of jaw assembly 450, it is contemplated that one proximal end of the second cable 124, and one proximal end of the third cable 126, is drawn in a proximal direction as a result of an input from control device 4 to activate a third or a fifth motor (not shown), and optionally activate a fourth or a sixth motor (not shown) to let out the other proximal end of the second or third cable 124, 126. Depending on which proximal end of the second cable 124 and the third cable 126 is drawn in a proximal direction will determine which direction of pivot, about second pivot axis "B-B," is transmitted to support plate 452 or 454 to thus pivot jaws 472, 474.

Also in operation, in order to open or close jaws 472, 474 of end effector 400, about pivot point 476 of jaws 472, 474, it is contemplated that one proximal end of one of the second cable and third cable 124, 126 is drawn in a proximal direction as a result of an input from control device 4 to activate a third motor or a fifth motor (not shown), and optionally activate a fourth motor or a sixth motor (not shown) to let out the other proximal end of the second cable 124 or third cable 126. Depending on which proximal end of the second cable 124 or third cable 126 is drawn in a proximal direction will determine which direction cam plates 462a, 462b of cam pulley assemblies 460a, 460b is rotated relative to one another (about pivot/rotation axis "B-B") and thus whether jaws 472, 474 are opened or closed. Specifically, as cam plate 462a of cam plate 462b is rotated in a first direction, camming pin 466 (disposed within angled cam slot 472c, 474c of jaws 472, 474 and slots 452a, 454a of support plates 452, 454) interconnected to cam plates 462a, 462b by respective cam links 464a, 464b, is slid or cammed distally through angled cam slot 472c, 474c of jaws 472, 474 and drawn distally through slots 452a, 454a of support plates 452, 454, by cam links 464a, 464b, to thereby open jaws 472, 474.

Likewise, as cam plate 462a or cam plate 462b is rotated in a second direction, camming pin 466 is slid or cammed proximally through angled cam slot 472c, 474c of jaws 472, 474 and pushed proximally through slots 452a, 454a of support plates 452, 454, by cam links 464a, 464b, to thereby close jaws 472, 474.

Turning now to FIGS. 51-62, an end effector for connection to robot arms 2, 3 and for manipulation by control device 4, in accordance with yet another embodiment of the present disclosure, is generally designated as 500. End effector 500 is substantially similar to end effector 400 and thus will only be described in detail herein to the extent necessary to describe differences in construction and/or operation over end effector 400.

End effector 500 includes a wrist assembly 510, and a jaw assembly 550 pivotally connected to wrist assembly 510. Wrist assembly 510 includes a proximal hub 512 defining a first longitudinal axis "X1-X1," and a first pivot axis "A-A" that is oriented orthogonal to the first longitudinal axis "X1-X1." Wrist assembly 510 further includes a distal hub 514 pivotally connected to proximal hub 512. Distal hub 514 defines a second longitudinal axis "X2-X2," and a second pivot axis "B-B" that is oriented orthogonal to the first pivot axis "A-A" and orthogonal to the first longitudinal axis "X1-X1." In an embodiment, when the first longitudinal axis "X1-X1" is parallel with the second longitudinal axis "X2-X2" (i.e., end effector 500 is in an axially aligned orientation), second pivot axis "B-B" may extend through first longitudinal axis "X1-X1."

Figure 59:
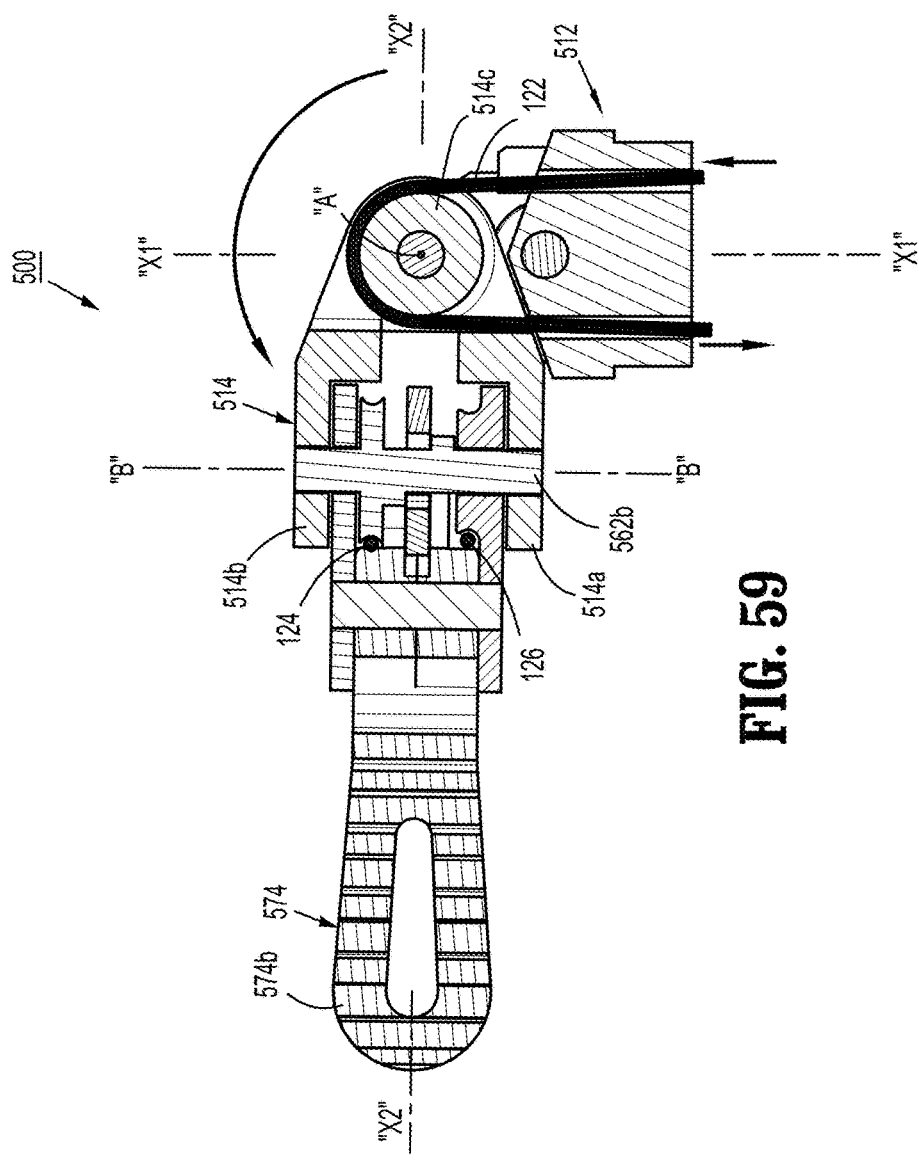
FIG. 59 is a cross-sectional view of the end effector of FIG. 51, as taken through section line 59-59 of FIG. 53, illustrating the end effector in an articulated condition.
Figure 58:
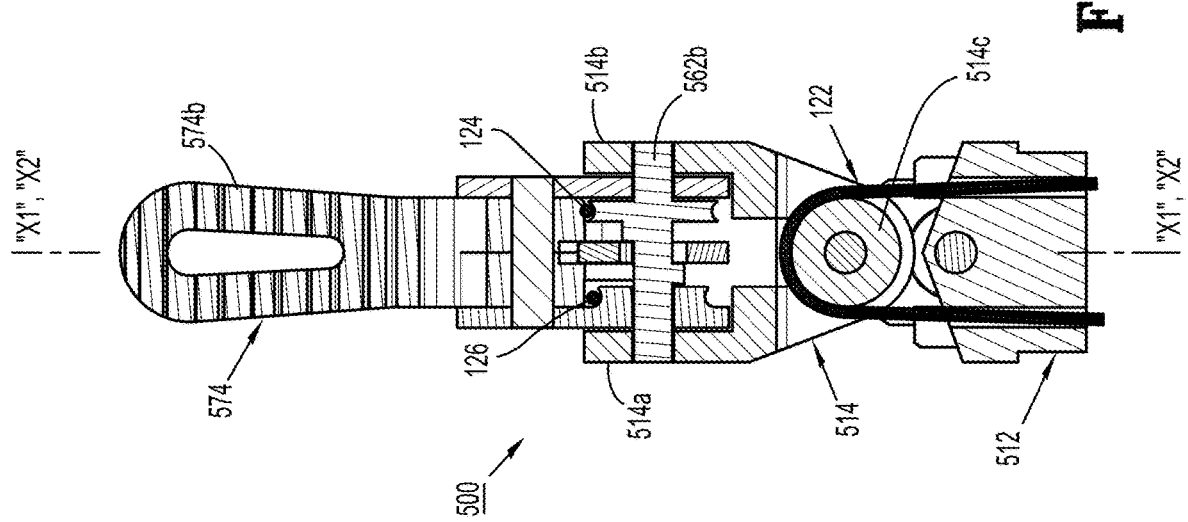
FIG. 58 is a cross-sectional view of the end effector of FIG. 51, as taken through section line 58-58 of FIG. 51, illustrating the end effector in a non-articulated condition.
Figure 60:
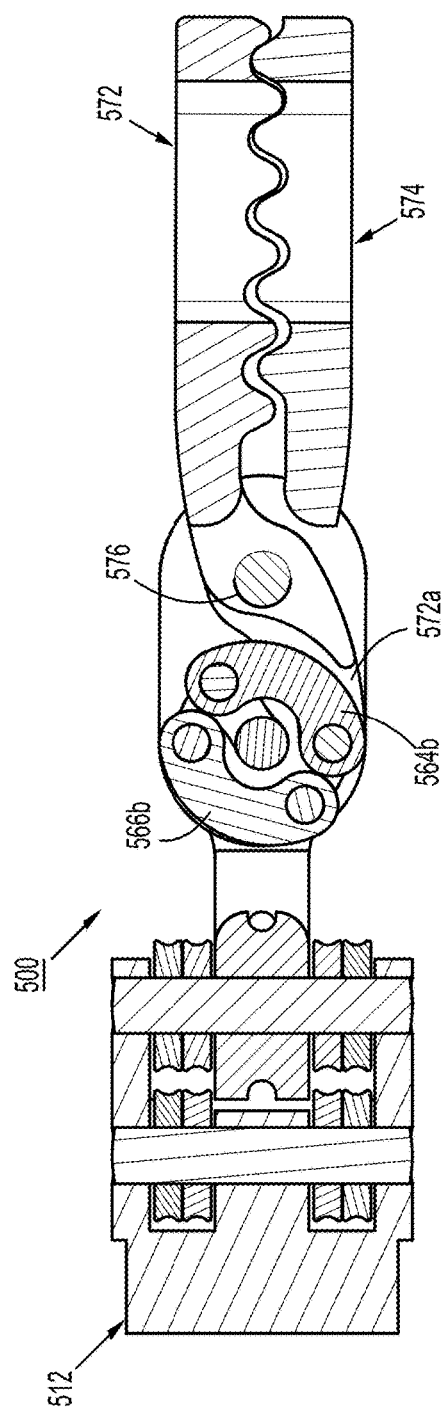
FIG. 60 is a cross-sectional view of the end effector of FIG. 51, as taken through section line 60-60 of FIG. 51, illustrating the jaw assembly in a closed condition.
Figure 61:
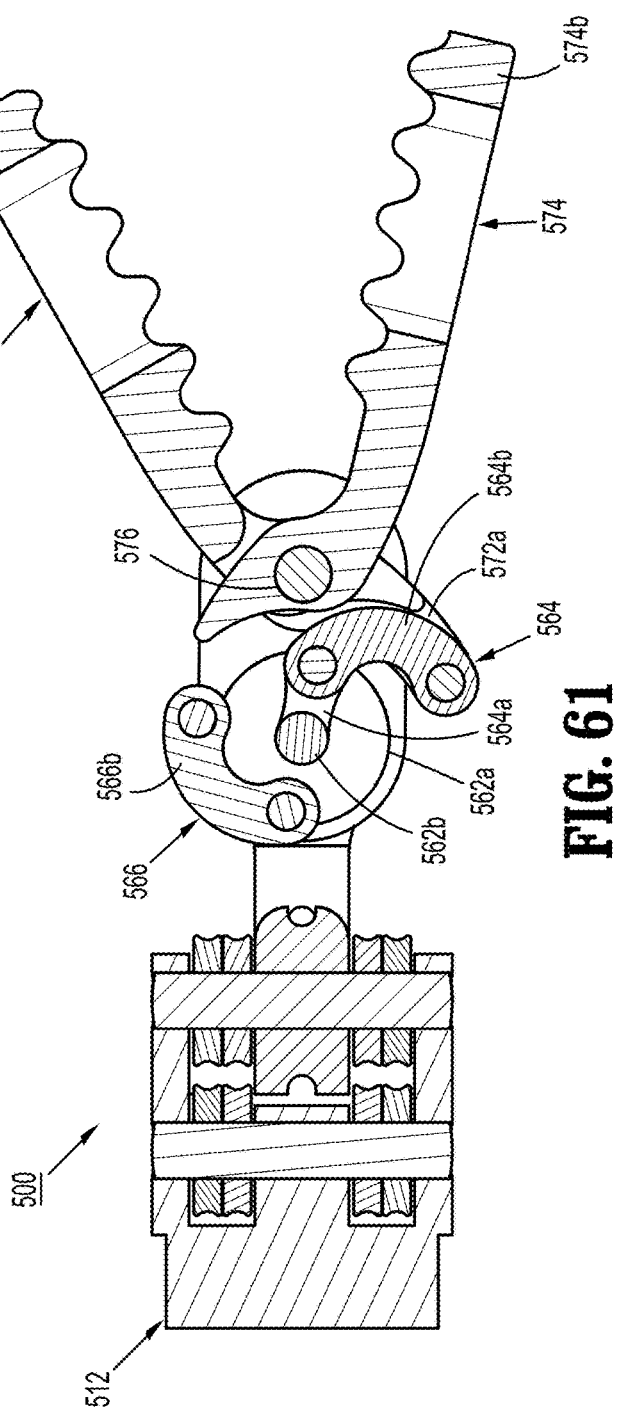
FIG. 61 is a cross-sectional view of the end effector of FIG. 52, as taken through section line 61-61 of FIG. 52, illustrating the jaw assembly in an open condition.
Figure 62:
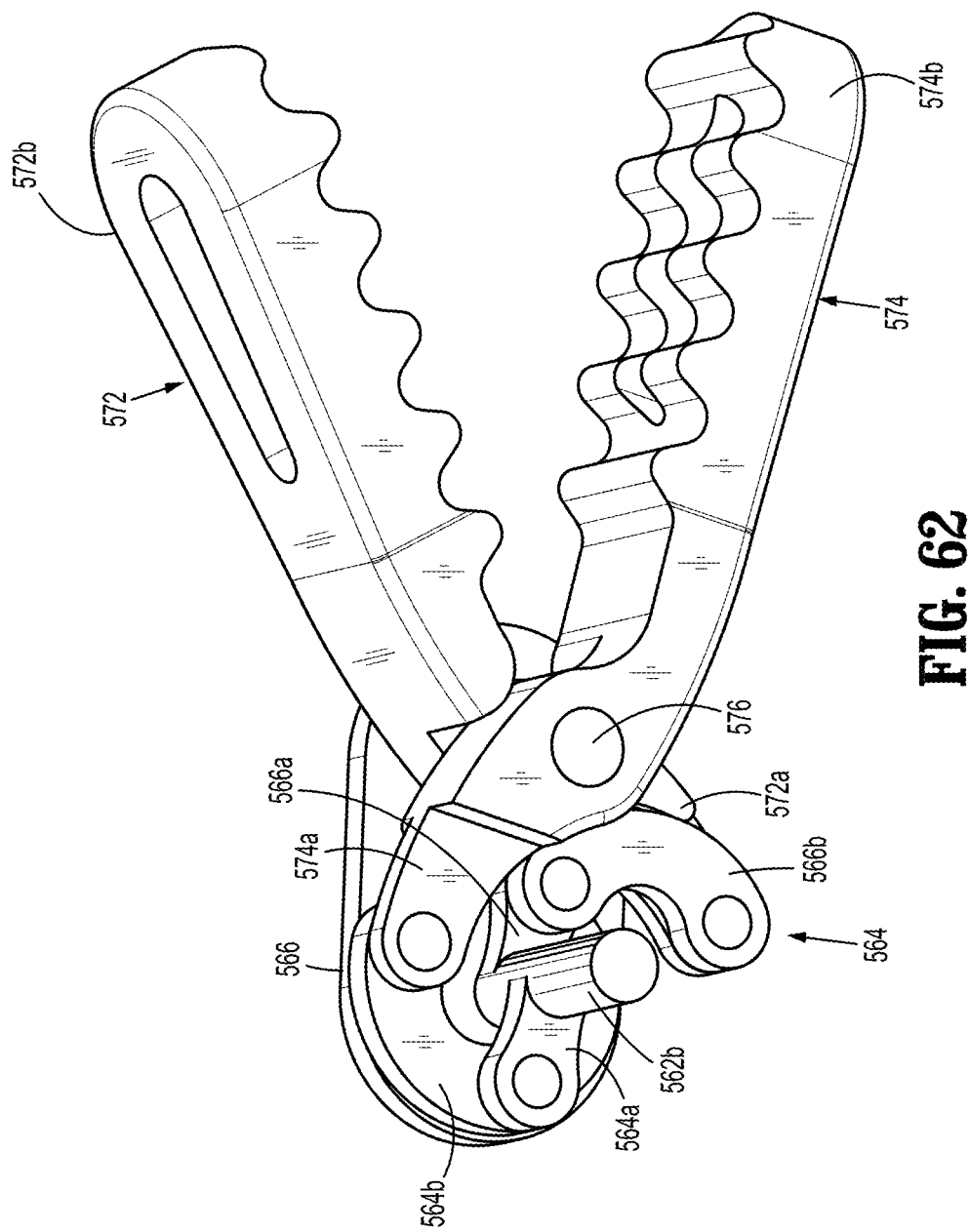
FIG. 62 is a perspective view of the jaw assembly of the end effector of FIG. 51 shown in an open condition.

With reference to FIGS. 58 and 59, a single first cable 122 is at least partially wrapped around a cam plate 514c of distal hub 514 and secured to at least one point thereof, or that the single first cable 122 may be wrapped at least once around cam plate 514c, in the manner of a capstan. Single first cable 122 may include proximal ends that extend through robot arm 2 or 3 and operatively associated with a respective first motor and second motor (not shown) of control device 4. While a single first cable 122 is shown and described, it is contemplated that a first pair of cables (not shown) including respective distal ends may be secured to opposed sides of cam plate 514c, or wrapped at least 180° around cam plate 514c and secured thereto, and including respective proximal ends extending through robot arm 2 or 3 and operatively associated with a respective first motor and second motor (not shown) of control device 4.

With continued reference to FIGS. 51-62, end effector 500 includes a jaw assembly 550 having a pair of spaced apart support or cam plates, or cam pulleys 552, 554 pivotally connected to respective spaced apart upright supports 514a, 514b of distal hub 514 of wrist assembly 510, so as to be pivotable about second pivot axis "B-B." Each support plate 552, 554 extends distally from a pivot pin 566 which defines second pivot axis "B-B."

Jaw assembly 550 also includes a pair of jaws 572, 574 pivotally connected to support plates 552, 554, and to upright supports 514a, 514b of distal hub 514, at a common pivot point 576 about which each jaw 572, 574 pivots. Pivot point 576 is located distally of second pivot "B-B". Each jaw 572, 574 includes a respective proximal end 572a, 574a, and a respective distal end 572b, 574b. Each proximal end 572a, 574a extends proximally of pivot point 576, and each distal end 572b, 574b extends distally of pivot point 576.

Jaw assembly 550 further includes at least one cam pulley assembly 560 having a cam plate 562a non-rotatably supported on a pivot pin 562b extending between spaced apart upright supports 514a, 514b of distal hub 514, wherein second pivot axis "B-B" extends along pivot pin 562b. Cam pulley assembly 560 further includes a pair of cam linkages 564, 566 interconnecting pivot pin 562b and the proximal end 572a, 574a of jaws 572, 574. Specifically, cam linkage 564 includes a proximal link 564a having a first end connected (e.g., fixedly, non-rotatably, keyed, etc.) to pivot pin 562b, and a distal link 564b pivotally interconnecting a second end of proximal link 564a and proximal end 574a of jaw 574. Likewise, cam linkage 566 includes a proximal link 566a having a first end connected (e.g., fixedly, non-rotatably, keyed, etc.) to pivot pin 562b, and a distal link 566b pivotally interconnecting a second end of proximal link 566a and proximal end 572a of jaw 572. In use, as will be described in greater detail below, as cam plate 562 is rotated in either a clockwise or counter clockwise direction, jaws 572, 574 will be caused to be opened or closed via first and second linkages 564, 566. The lengths of cam linkages 564, 566 may be modified or selected so as to vary or alter a closing/opening characteristic of jaw assembly 550, such as for example, to increase a clamping force (i.e., act as a force multiplier) of the jaw assembly 550 as the jaw assembly 550 is brought to a fully closed condition.

Figure 55:
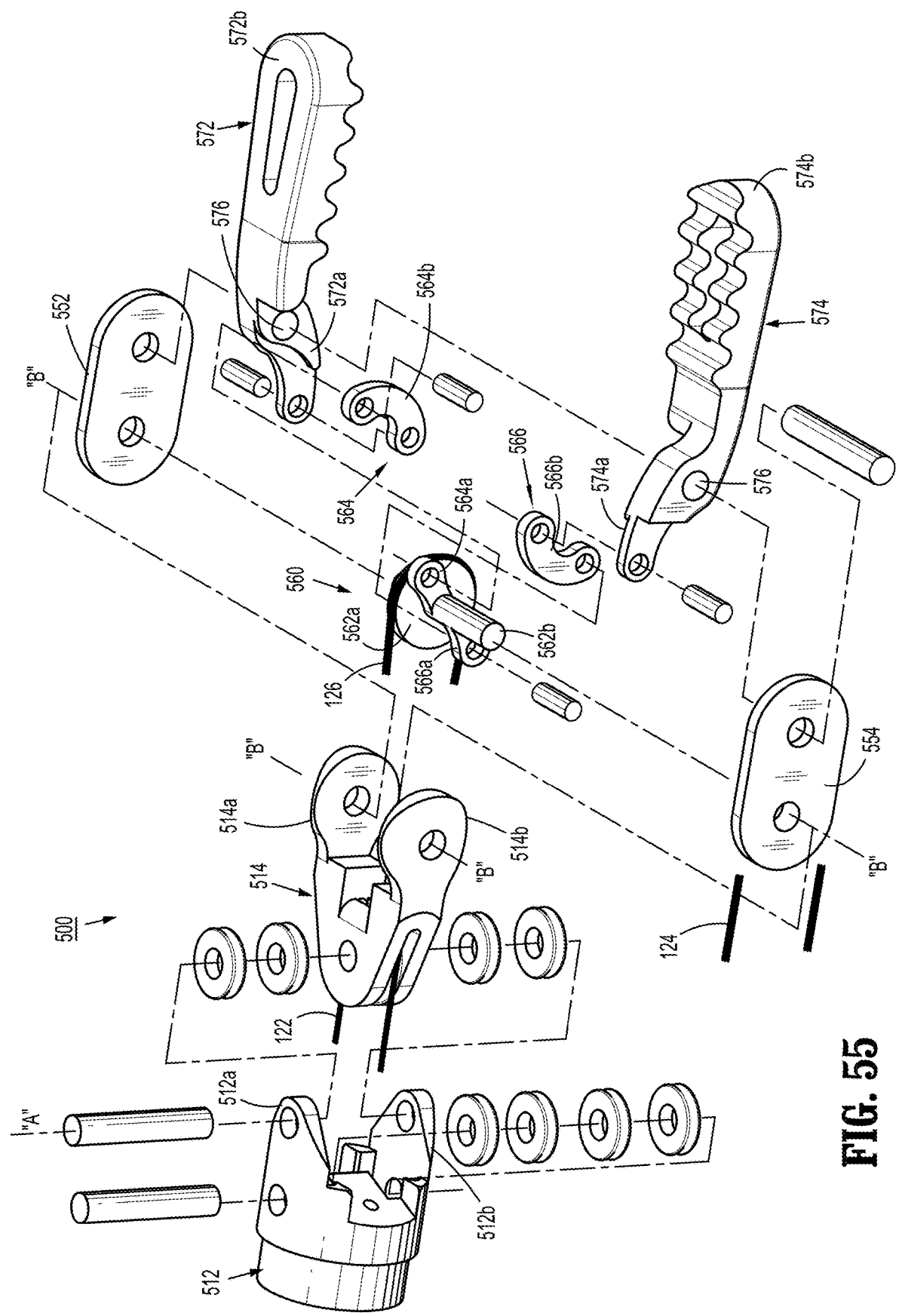
FIG. 55 is a perspective view, with parts separated, of the end effector of FIG. 51.
Figure 56:
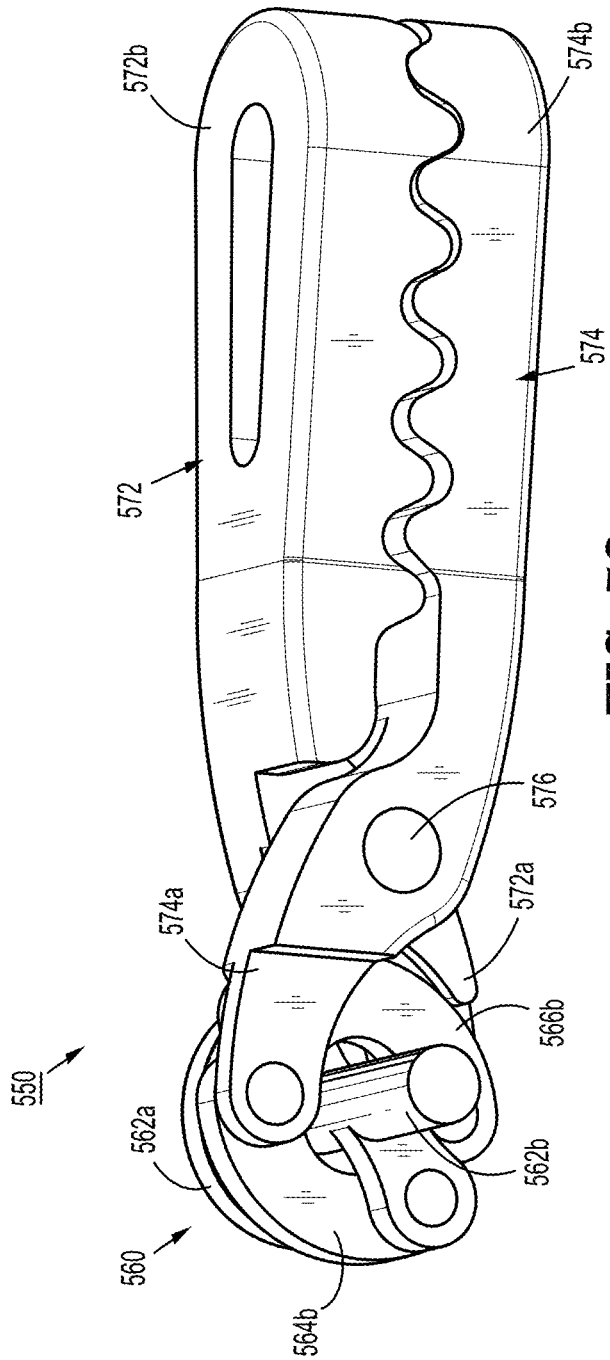
FIG. 56 is a rear, perspective view of the jaw assembly of the end effector of FIG. 51, illustrating the jaw assembly in the closed condition.
Figure 57:
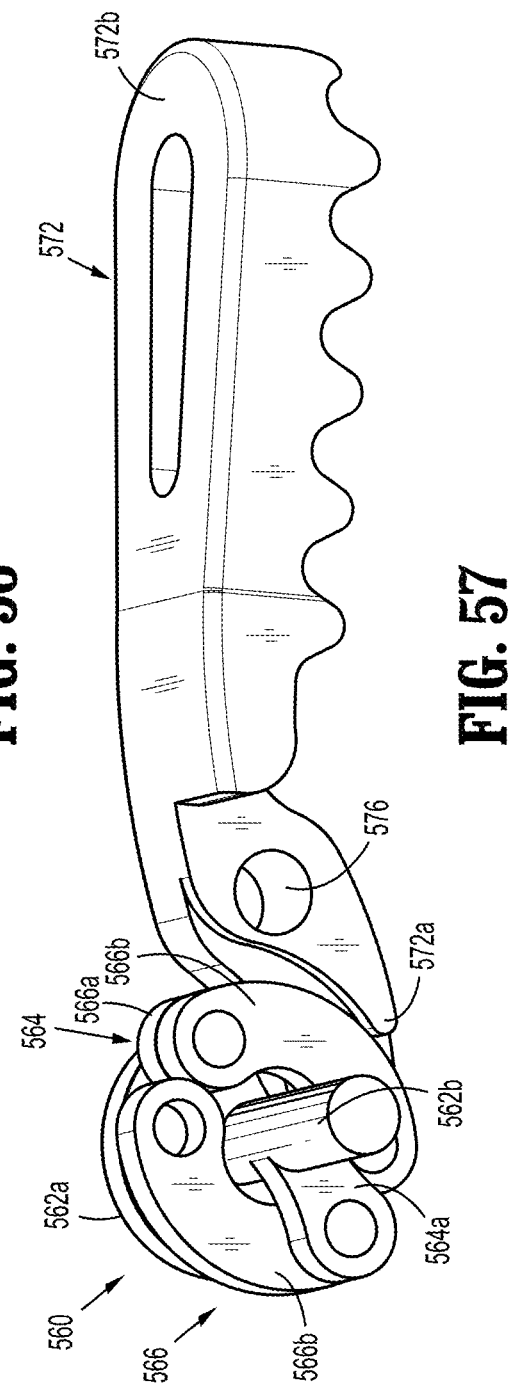
FIG. 57 is a perspective view of the jaw assembly of the end effector of FIG. 51 with a jaw removed therefrom.

As illustrated in FIG. 55, a single second cable 124 may be at least partially wrapped around one of support plates 552, 554 and secured to at least one point thereof, or that the single second cable 124 may be wrapped at least once around one of support plates 552, 554, in the manner of a capstan. The single second cable 124 may include proximal ends (not shown) that extend through robot arm 2 or 3 and operatively associated with a respective third motor and fourth motor (not shown) of control device 4. While a single second cable 124 is described, it is contemplated that a second pair of cables (not shown) including respective distal ends may be secured to opposed sides of support plates 552, 554, or wrapped at least 180° around support plates 552, 554 and secured thereto, and including respective proximal ends extending through robot arm 2 or 3 and operatively associated with a respective third motor and fourth motor (not shown) of control device 4.

Additionally, a single third cable 126 may be at least partially wrapped around cam plate 562a and secured to at least one point thereof, or that the single third cable 126 may be wrapped at least once around cam plate 562a, in the manner of a capstan. Single third cable 126 may include proximal ends (not shown) that extend through robot arm 2 or 3 and operatively associated with a respective fifth motor (not shown) and sixth motor (not shown) of control device 4. While a single third cable 126 is described, it is contemplated that a third pair of cables (not shown) including respective distal ends may be secured to opposed sides of cam plate 562a, or wrapped at least 180° around cam plate 562a and secured thereto, and including respective proximal ends extending through robot arm 2 or 3 and operatively associated with a respective fifth motor (not shown) and sixth motor (not shown) of control device 4

In operation, in order to pivot end effector 500 about first pivot axis "A-A" of wrist assembly 510, it is contemplated that one proximal end of the first cable 122 is drawn in a proximal direction as a result of an input from control device 4 to activate a first motor (not shown), and optionally activate a second motor (not shown) to let out the other proximal end of the first cable 122. Depending on which proximal end of the cable 122 is drawn in a proximal direction will determine which direction of pivot, about first pivot axis "A-A," is achieved.

Additionally, in operation, in order to pivot jaws 572, 574 of end effector 500 about second pivot axis "B-B" of jaw assembly 550, it is contemplated that one proximal end of the second cable 124 is drawn in a proximal direction as a result of an input from control device 4 to activate a third motor (not shown), and optionally activate a fourth motor (not shown) to let out the other proximal end of the second cable. Depending on which proximal end of the second cable is drawn in a proximal direction will determine which direction of pivot, about second pivot axis "B-B," is transmitted to support plate 552 or 554 to thus pivot jaws 572, 574.

Also in operation, in order to open or close jaws 572, 574 of end effector 500, about pivot point 576 of jaws 572, 574, it is contemplated that one proximal end of the third cable 126 is drawn in a proximal direction as a result of an input from control device 4 to activate a fifth motor (not shown), and optionally activate a sixth motor (not shown) to let out the other proximal end of the third cable. Depending on which proximal end of the third cable is drawn in a proximal direction will determine which direction plate 562a of linkage assembly 562 is rotated (about pivot/rotation axis "B-B") and thus whether jaws 572, 574 are opened or closed. Specifically, as plate 562a is rotated in a first direction, thus rotating pivot pin 562b in the first direction, proximal links 564a, 566a of linkages 564, 566 are caused to be rotated in the first direction about second pivot axis "B-B" to thereby draw distal links 564b, 566b of linkages 564, 566 radially inward and thus draw proximal ends 572a, 574a of jaws 572, 574 radially inward to thereby close jaws 572, 574.

Likewise, as plate 562a is rotated in a second direction, thus rotating pivot pin 562b in the second direction, proximal links 564a, 566a of linkages 564, 566 are caused to be rotated in the second direction about second pivot axis "B-B" to thereby push distal links 564b, 566b of linkages 564, 566 radially outward and thus push proximal ends 572a, 574a of jaws 572, 574 radially outward to thereby open jaws 572, 574.

It will be understood that various modifications may be made to the embodiments disclosed herein. For example, while the cam pulleys disclosed herein have been shown and described as being connected to the proximal ends of the jaws, it is contemplated and within the scope of the present disclosure, for the cam pulley to be operatively connected with the distal portion of the jaws. Therefore, the above description should not be construed as limiting, but merely as exemplifications of various embodiments. Those skilled in the art will envision other modifications within the scope and spirit of the claims appended thereto.

The invention claimed is:

1. A surgical tool comprising:
   a first jaw;
   a second jaw;

a first cam pulley positioned to open or close the first and second jaws about a first axis, wherein the first cam pulley defines at least one arcuate slot formed in a surface of the first cam pulley, wherein each jaw is in sliding and camming connection with a respective arcuate slot of the first cam pulley, each arcuate slot including:
  a first end portion spaced a first radial distance from a pivot axis of the first cam pulley; and
  a second end portion spaced a second radial distance from the pivot axis of the first cam pulley; and
a second cam pulley positioned to rotate the first and second jaws about a second axis that is different from the first axis, the first and second cam pulleys coupled to the first and second jaws.

2. The surgical tool according to claim 1, further comprising a cam follower that couples the first and the second cam pulleys to the first and second jaws.

3. The surgical tool according to claim 2, wherein the first cam pulley multiplies a closure force acting on the first and second jaws as the first cam pulley is rotated to close the first and second jaws.

4. The surgical tool according to claim 3, wherein the first cam pulley defines a single arcuate slot formed therein, and wherein a proximal end portion of each jaw defines an angled slot formed therein, wherein the angled slots diverge from one another in a proximal direction, and wherein a cam pin is slidably disposed within the arcuate slot of the first cam pulley and the angled slot of each jaw.

5. The surgical tool according to claim 4, wherein the second cam pulley defines an axially extending slot formed therein, and wherein the cam pin is slidably disposed within the axially extending slot formed in the second cam pulley.

6. The surgical tool according to claim 3, wherein the first cam pulley includes at least one cam plate, and wherein a cam link is pivotally connected to the at least one cam plate and the second cam pulley.

7. The surgical tool according to claim 6, wherein the second cam pulley defines a longitudinally extending slot formed therein, and wherein the cam link includes a first end portion pivotally connected to the at least one cam plate, and a second end portion pivotably and slidably connected to the longitudinally extending slot formed in the second cam pulley.

8. The surgical tool according to claim 7, wherein a proximal end portion of each jaw defines an angled slot formed therein, wherein the angled slots diverge from one another in a proximal direction, and wherein a cam pin is slidably disposed within the axial slot of the second cam pulley and the angled slot of each jaw.

9. The surgical tool according to claim 3, wherein the first cam pulley includes at least one cam plate, and wherein at least one cam linkage is pivotally connected to the at least one cam plate and a proximal portion of a jaw.

10. The surgical tool according to claim 9, wherein the first cam pulley includes a pivot pin disposed along the second axis, and wherein the pivot pin non-rotatably supports the cam plate, and wherein the at least one cam linkage includes:
  a first cam linkage having a proximal link non-rotatably extending from the pivot pin of the first cam pulley, and a distal link pivotably interconnecting the proximal link of the first cam linkage and the proximal portion of the first jaw; and
  a second cam linkage having a proximal link non-rotatably extending from the pivot pin of the first cam pulley, and a distal link pivotably interconnecting the proximal link of the second cam linkage and the proximal portion of the second jaw, wherein the proximal link of the second cam linkage is radially offset from the proximal link of the first cam linkage.

11. An end effector connectable to a robot arm of a robotic surgical system, the end effector comprising:
  at least one cam plate;
  a pair of jaws supported on the at least one cam plate, wherein each jaw includes a pivot point connected to the at least one cam plate; and
  a cam pulley supported on the at least one cam plate, the cam pulley connected to the pair of jaws and rotatable to open or close the pair of jaws; and
  a wrist assembly supporting the pair of jaws, the wrist assembly including:
    a proximal hub defining a longitudinal axis; and
    a distal hub pivotally connected to the proximal hub, wherein the distal hub defines a longitudinal axis, and wherein the proximal hub and the distal hub are pivotable about a first pivot axis that is oriented transverse to the longitudinal axis of the proximal hub; and
  wherein the pair of jaws are pivotally connected to the distal hub of the wrist assembly, the at least one cam plate is pivotable about a second pivot axis that is oriented transverse to the longitudinal axis of the distal hub of the wrist assembly, the cam pulley includes a pivot pin disposed along the second pivot axis, and the pivot pin non-rotatably supports the at least one cam plate.

12. The end effector according to claim 11, wherein the cam pulley is pivotally supported, on the at least one cam plate, at the second pivot axis, the cam pulley defining at least one arcuate slot formed in a surface thereof, each arcuate slot including:
  a first end portion spaced a first radial distance from a pivot axis of the cam pulley; and
  a second end portion spaced a second radial distance from the pivot axis of the cam pulley, and
  wherein the proximal portion of each jaw is in sliding and camming connection with a arcuate slot of the cam pulley.

13. The end effector according to claim 11, further comprising:
  a first cam linkage having a proximal link non-rotatably extending from the pivot pin of the cam pulley, and a distal link pivotably interconnecting the proximal link of the first cam linkage and a proximal portion of a first jaw of the pair of jaws; and
  a second cam linkage having a proximal link non-rotatably extending from the pivot pin of the cam pulley, and a distal link pivotably interconnecting the proximal link of the second cam linkage and a proximal portion of a second jaw of the pair of jaws, wherein the proximal link of the second cam linkage is radially offset from the proximal link of the first cam linkage.

14. A surgical tool comprising:
  a first jaw;
  a second jaw, wherein a proximal end portion of each jaw defines an angled slot formed therein, and wherein the angled slots diverge from one another in a proximal direction;
  a first cam pulley positioned to open or close the first and second jaws about a first axis, the first cam pulley defining a single arcuate slot formed in the first cam pulley;

a cam pin is slidably disposed within the single arcuate slot of the first cam pulley and the angled slot of each jaw; and a second cam pulley positioned to rotate the first and second jaws about a second axis that is different from the first axis, the first and second cam pulleys coupled to the first and second jaws.

15. The surgical tool of claim 14, wherein the second cam pulley defines an axially extending slot formed therein, and wherein the cam pin is slidably disposed within the axially extending slot formed in the second cam pulley.

16. A surgical tool comprising:

a first jaw;

a second jaw;

a first cam pulley positioned to open or close the first and second jaws about a first axis, the first cam pulley including a first cam plate;

a second cam pulley positioned to rotate the first and second jaws about a second axis that is different from the first axis, the first and second cam pulleys coupled to the first and second jaws, the second cam pulley defining a longitudinally extending slot formed therein; and a cam link pivotally connected to the first cam plate, the cam link including a first end portion pivotally connected to the first cam plate, and a second end portion pivotably and slidably connected to the longitudinally extending slot formed in the second cam pulley.

* * * * *